United States Patent
Rosenblum et al.

(10) Patent No.: US 10,246,712 B2
(45) Date of Patent: Apr. 2, 2019

(54) GENETIC OR PHARMACOLOGICAL REDUCTION OF PERK ENHANCES CORTICAL- AND HIPPOCAMPUS-DEPENDENT COGNITIVE FUNCTION

(71) Applicant: Carmel-Haifa University Economic Corp. Ltd, Haifa (IL)

(72) Inventors: Kobi Rosenblum, Zichron Yaacov (IL); Vijendra Sharma, Ujjain (IN); Hadile Ounallah Saad, Umm Alfahm (IL)

(73) Assignee: Carmel-Haifa University Economic Corp. Ltd., Haifa (IL)

( * ) Notice: Subject to any disclaimer, the term of this patent is extended or adjusted under 35 U.S.C. 154(b) by 0 days.

(21) Appl. No.: 15/335,466

(22) Filed: Oct. 27, 2016

(65) Prior Publication Data

US 2018/0265873 A1    Sep. 20, 2018

Related U.S. Application Data

(60) Provisional application No. 62/247,255, filed on Oct. 28, 2015.

(51) Int. Cl.

| | |
|---|---|
| *C07H 21/02* | (2006.01) |
| *C07H 21/04* | (2006.01) |
| *A61K 31/70* | (2006.01) |
| *A61K 31/519* | (2006.01) |
| *C12N 15/113* | (2010.01) |
| *A61P 25/00* | (2006.01) |
| *A61K 9/00* | (2006.01) |

(52) U.S. Cl.
CPC ........ *C12N 15/1137* (2013.01); *A61K 9/0085* (2013.01); *A61K 31/519* (2013.01); *A61P 25/00* (2018.01)

(58) Field of Classification Search
None
See application file for complete search history.

(56) References Cited

U.S. PATENT DOCUMENTS

2011/0052566 A1    3/2011    Rosenblum et al.

OTHER PUBLICATIONS

Axten et al; "Discovery of GSK2656157: An Optimized PERK Inhibitor Selected for Preclinical Development" American Chemical Society 4, pp. 964-968. (2013).
Costa-Mattioli et al; "eIF2α Phosphorylation Bidirectionally Regulates the Switch from Short- to Long-Term Synaptic Plasticity and Memory" Cell 129, pp. 195-206. Apr. 6, 2007.
Gal-Ben-Ari et al; "Consolidation and translation regulation" Learning & Memory 19 :pp. 410-422. (2012).
Ma et al; "Suppression of eIF2α kinases alleviates AD-related synaptic plasticity and spatial memory deficits" Nat Neurosci. 16(9): pp. 1299-1305. Sep. 2013.
Moreno et al; "Sustained translational repression by eIF2α-P mediates prion neurodegeneration" Nature 485(7399): pp. 507-511. Jun. 19, 2012, 14 pages.
Moreno et al; "Oral Treatment Targeting the Unfolded Protein Response Prevents Neurodegeneration and Clinical Disease in Prion-Infected Mice" Science Translational Medicinevol. 5 Issue 206 pp. 1-10. Oct. 9, 2013.
Hadile Ounallah-Saad et al; "Genetic or Pharmacological Reduction of PERK Enhances Cortical-Dependent Taste Learning" The Journal of Neuroscience 34(44):pp. 14624-14632, Oct. 29, 2014.
Radford et al; "PERK inhibition prevents tau-mediated neurodegeneration in a mouse model of frontotemporal dementia" Acta Neuropathol 130:pp. 633-642. (2015).
Stern et al; "Blocking the eIF2α Kinase (PKR) Enhances Positive and Negative Forms of Cortex-Dependent Taste Memory" The Journal of Neuroscience 33(6): pp. 2517-2525, Feb. 6, 2013.
Trinh et al: Brain-specific Disruption of the eIF2α Kinase PERK Decreases ATF4 Expression and Impairs Behavioral FlexibilityCell Rep. 1(6): pp. 676-688, Jun. 28, 2012, 27 pages.
Trinh et al: "The eIF2α kinase PERK limits the expression of hippocampal metabotropic glutamate receptor-dependent long-term depression" Learning & Memory 21:pp. 298-304. (2014).

*Primary Examiner* — Sean McGarry
(74) *Attorney, Agent, or Firm* — Knobbe, Martens, Olson & Bear, LLP

(57) ABSTRACT

A method for improving a cognitive function in a subject comprising administering to said subject an active agent reducing PKR-like endoplasmic reticulum kinase (PERK) activity is provided.

17 Claims, 30 Drawing Sheets
(30 of 30 Drawing Sheet(s) Filed in Color)
Specification includes a Sequence Listing.

A.

B.

D.

A.

Interneutral 10.20 mm　　　　　　　　　　　Bregma 1.20 mm

Interneutral 10.20 mm　　　　　　　　　　　Bregma 1.20 mm

A.

B.

A.

B.

a.

b.

c.

d.

e.

f.

g.

a.

b.

f.

g.

h.

i.

a.

b.

c.

e.

f.

a.

b.

a.

b.

a.

b.

c.

d.

a.

b.

c.

d.

SEQUENCE LISTING

```
<160> NUMBER OF SEQ ID NOS: 3

<210> SEQ ID NO 1
<211> LENGTH: 1115
<212> TYPE: PRT
<213> ORGANISM: Homo sapiens

<400> SEQUENCE: 1

Met Glu Arg Ala Ile Ser Pro Gly Leu Leu Val Arg Ala Leu Leu Leu
1               5                   10                  15

Leu Leu Leu Leu Gly Leu Ala Ala Arg Thr Val Ala Ala Gly Arg Ala
            20                  25                  30

Arg Gly Leu Pro Ala Pro Thr Ala Glu Ala Ala Phe Gly Leu Gly Ala
        35                  40                  45

Ala Ala Ala Pro Thr Ser Ala Thr Arg Val Pro Ala Ala Gly Ala Val
    50                  55                  60

Ala Ala Ala Glu Val Thr Val Glu Asp Ala Glu Ala Leu Pro Ala Ala
65                  70                  75                  80

Ala Gly Glu Gln Glu Pro Arg Gly Pro Glu Pro Asp Asp Glu Thr Glu
                85                  90                  95
```

```
Leu Arg Pro Arg Gly Arg Ser Leu Val Ile Ile Ser Thr Leu Asp Gly
            100                 105                 110

Arg Ile Ala Ala Leu Asp Pro Glu Asn His Gly Lys Lys Gln Trp Asp
        115                 120                 125

Leu Asp Val Gly Ser Gly Ser Leu Val Ser Ser Leu Ser Lys Pro
130                 135                 140

Glu Val Phe Gly Asn Lys Met Ile Ile Pro Ser Leu Asp Gly Ala Leu
145                 150                 155                 160

Phe Gln Trp Asp Arg Asp Arg Glu Ser Met Glu Thr Val Pro Phe Thr
                165                 170                 175

Val Glu Ser Leu Leu Glu Ser Ser Tyr Lys Phe Gly Asp Asp Val Val
        180                 185                 190

Leu Val Gly Gly Lys Ser Leu Thr Thr Tyr Gly Leu Ser Ala Tyr Ser
        195                 200                 205

Gly Lys Val Arg Tyr Ile Cys Ser Ala Leu Gly Cys Arg Gln Trp Asp
210                 215                 220

Ser Asp Glu Met Glu Gln Glu Asp Ile Leu Leu Leu Gln Arg Thr
225                 230                 235                 240

Gln Lys Thr Val Arg Ala Val Gly Pro Arg Ser Gly Asn Glu Lys Trp
            245                 250                 255

Asn Phe Ser Val Gly His Phe Glu Leu Arg Tyr Ile Pro Asp Met Glu
            260                 265                 270

Thr Arg Ala Gly Phe Ile Glu Ser Thr Phe Lys Pro Asn Glu Asn Thr
        275                 280                 285

Glu Glu Ser Lys Ile Ile Ser Asp Val Glu Glu Gln Glu Ala Ala Ile
        290                 295                 300

Met Asp Ile Val Ile Lys Val Ser Val Ala Asp Trp Lys Val Met Ala
305                 310                 315                 320

Phe Ser Lys Lys Gly Gly His Leu Glu Trp Glu Tyr Gln Phe Cys Thr
            325                 330                 335

Pro Ile Ala Ser Ala Trp Leu Leu Lys Asp Gly Lys Val Ile Pro Ile
            340                 345                 350

Ser Leu Phe Asp Asp Thr Ser Tyr Thr Ser Asn Asp Asp Val Leu Glu
            355                 360                 365

Asp Glu Glu Asp Ile Val Glu Ala Ala Arg Gly Ala Thr Glu Asn Ser
370                 375                 380

Val Tyr Leu Gly Met Tyr Arg Gly Gln Leu Tyr Leu Gln Ser Ser Val
385                 390                 395                 400

Arg Ile Ser Glu Lys Phe Pro Ser Ser Pro Lys Ala Leu Glu Ser Val
            405                 410                 415

Thr Asn Glu Asn Ala Ile Ile Pro Leu Pro Thr Ile Lys Trp Lys Pro
            420                 425                 430

Leu Ile His Ser Pro Ser Arg Thr Pro Val Leu Val Gly Ser Asp Glu
            435                 440                 445

Phe Asp Lys Cys Leu Ser Asn Asp Lys Phe Ser His Glu Glu Tyr Ser
    450                 455                 460

Asn Gly Ala Leu Ser Ile Leu Gln Tyr Pro Tyr Asp Asn Gly Tyr Tyr
465                 470                 475                 480

Leu Pro Tyr Tyr Lys Arg Glu Arg His Lys Arg Ser Thr Gln Ile Thr
            485                 490                 495

Val Arg Phe Leu Asp Asn Pro His Tyr Asn Lys Asn Ile Arg Lys Lys
            500                 505                 510
```

-continued

Asp Pro Val Leu Leu His Trp Lys Glu Ile Ala Thr Ile
         515                 520                 525

Leu Phe Cys Ile Ile Ala Thr Thr Phe Ile Val Arg Arg Leu Phe His
530                         535                 540

Pro His Pro His Arg Gln Arg Lys Glu Ser Glu Thr Gln Cys Gln Thr
545                 550                 555                 560

Glu Asn Lys Tyr Asp Ser Val Ser Gly Glu Ala Asn Asp Ser Ser Trp
                565                 570                 575

Asn Asp Ile Lys Asn Ser Gly Tyr Ile Ser Arg Tyr Leu Thr Asp Phe
                580                 585                 590

Glu Pro Ile Gln Cys Leu Gly Arg Gly Gly Phe Gly Val Val Phe Glu
            595                 600                 605

Ala Lys Asn Lys Val Asp Asp Cys Asn Tyr Ala Ile Lys Arg Ile Arg
        610                 615                 620

Leu Pro Asn Arg Glu Leu Ala Arg Glu Lys Val Met Arg Glu Val Lys
625                 630                 635                 640

Ala Leu Ala Lys Leu Glu His Pro Gly Ile Val Arg Tyr Phe Asn Ala
                645                 650                 655

Trp Leu Glu Ala Pro Pro Glu Lys Trp Gln Glu Lys Met Asp Glu Ile
                660                 665                 670

Trp Leu Lys Asp Glu Ser Thr Asp Trp Pro Leu Ser Ser Pro Ser Pro
            675                 680                 685

Met Asp Ala Pro Ser Val Lys Ile Arg Arg Met Asp Pro Phe Ser Thr
        690                 695                 700

Lys Glu His Ile Glu Ile Ile Ala Pro Ser Pro Gln Arg Ser Arg Ser
705                 710                 715                 720

Phe Ser Val Gly Ile Ser Cys Asp Gln Thr Ser Ser Ser Glu Ser Gln
                725                 730                 735

Phe Ser Pro Leu Glu Phe Ser Gly Met Asp His Glu Asp Ile Ser Glu
            740                 745                 750

Ser Val Asp Ala Ala Tyr Asn Leu Gln Asp Ser Cys Leu Thr Asp Cys
        755                 760                 765

Asp Val Glu Asp Gly Thr Met Asp Gly Asn Asp Glu Gly His Ser Phe
770                 775                 780

Glu Leu Cys Pro Ser Glu Ala Ser Pro Tyr Val Arg Ser Arg Glu Arg
785                 790                 795                 800

Thr Ser Ser Ser Ile Val Phe Glu Asp Ser Gly Cys Asp Asn Ala Ser
                805                 810                 815

Ser Lys Glu Glu Pro Lys Thr Asn Arg Leu His Ile Gly Asn His Cys
            820                 825                 830

Ala Asn Lys Leu Thr Ala Phe Lys Pro Thr Ser Ser Lys Ser Ser Ser
        835                 840                 845

Glu Ala Thr Leu Ser Ile Ser Pro Pro Arg Pro Thr Thr Leu Ser Leu
        850                 855                 860

Asp Leu Thr Lys Asn Thr Thr Glu Lys Leu Gln Pro Ser Ser Pro Lys
865                 870                 875                 880

Val Tyr Leu Tyr Ile Gln Met Gln Leu Cys Arg Lys Glu Asn Leu Lys
                885                 890                 895

Asp Trp Met Asn Gly Arg Cys Thr Ile Glu Glu Arg Glu Arg Ser Val
                900                 905                 910

Cys Leu His Ile Phe Leu Gln Ile Ala Glu Ala Val Glu Phe Leu His
                915                 920                 925

```
Ser Lys Gly Leu Met His Arg Asp Leu Lys Pro Ser Asn Ile Phe Phe
    930                 935                 940

Thr Met Asp Asp Val Val Lys Val Gly Asp Phe Gly Leu Val Thr Ala
945                 950                 955                 960

Met Asp Gln Asp Glu Glu Glu Gln Thr Val Leu Thr Pro Met Pro Ala
                965                 970                 975

Tyr Ala Arg His Thr Gly Gln Val Gly Thr Lys Leu Tyr Met Ser Pro
                980                 985                 990

Glu Gln Ile His Gly Asn Ser Tyr  Ser His Lys Val Asp  Ile Phe Ser
            995                 1000                 1005

Leu Gly Leu Ile Leu Phe Glu  Leu Leu Tyr Pro Phe  Ser Thr Gln
        1010                1015                1020

Met Glu Arg Val Arg Thr Leu  Thr Asp Val Arg Asn  Leu Lys Phe
        1025                1030                1035

Pro Pro Leu Phe Thr Gln Lys  Tyr Pro Cys Glu Tyr  Val Met Val
        1040                1045                1050

Gln Asp Met Leu Ser Pro Ser  Pro Met Glu Arg Pro  Glu Ala Ile
        1055                1060                1065

Asn Ile Ile Glu Asn Ala Val  Phe Glu Asp Leu Asp  Phe Pro Gly
        1070                1075                1080

Lys Thr Val Leu Arg Gln Arg  Ser Arg Ser Leu Ser  Ser Ser Gly
        1085                1090                1095

Thr Lys His Ser Arg Gln Ser  Asn Asn Ser His Ser  Pro Leu Pro
        1100                1105                1110

Ser Asn
    1115

<210> SEQ ID NO 2
<211> LENGTH: 4662
<212> TYPE: DNA
<213> ORGANISM: Homo sapiens

<400> SEQUENCE: 2
ggaaagtcca ccttcccat caaggccagc ctgggaacat ggagtggcag cggccgcagc        60
aaatgagaga gccaacgcgc ggaaagtttg ctcaatgggc gatgtccgag ataggctgtc      120
actcaggtgg cagcggcaga ggccgggctg agacgtggcc aggggaacac ggctggctgt      180
ccaggccgtc ggggcggcag tagggtccct agcacgtcct tgccttcttg ggagctccaa      240
gcggcgggag aggcaggcgt cagtggctgc gcctccatgc ctgcgcgcgg ggcgggacgc      300
tgatggagcg cgccatcagc ccggggctgc tggtacgggc gctgctgctg ctgctgctgc      360
tggggctcgc ggcaaggacg gtggccgcgg ggcgcgcccg tggcctccca gcgccgacgg      420
cggaggcggc gttcggcctc ggggcggccg ctgctccac ctcagcgacg cgagtaccgg       480
cggcgggcgc cgtggctgcg gccgaggtga ctgtggagga cgctgaggcg ctgccggcag      540
ccgcgggaga gcaggagcct cggggtccgg aaccagacga tgagacagag ttgcgaccgc      600
gcggcaggtc attagtaatt atcagcactt tagatgggag aattgctgcc ttggatcctg      660
aaaatcatgg taaaaagcag tgggatttgg atgtgggatc cggttccttg gtgtcatcca      720
gccttagcaa accagaggta tttgggaata agatgatcat tccttccctg gatggagccc      780
tcttccagtg ggaccgagac cgtgaaagca tggaaacagt tcctttcaca gttgaatcac      840
ttcttgaatc ttcttataaa tttgagatg atgttgtttt ggttgaagga aaatctctga      900
ctacatatgg actcagtgca tatagtggaa aggtgaggta tatctgttca gctctggatt      960
```

```
gtcgccaatg ggatagtgac gaaatggaac aagaggaaga catcctgctt ctacagcgta      1020
cccaaaaaac tgttagagct gtcggacctc gcagtggcaa tgagaagtgg aatttcagtg      1080
ttggccactt tgaacttcgg tatattccag acatggaaac gagagccgga tttattgaaa      1140
gcacctttaa gcccaatgag aacacagaag agtctaaaat tatttcagat gtggaagaac      1200
aggaagctgc cataatggac atagtgataa aggtttcggt tgctgactgg aaagttatgg      1260
cattcagtaa gaagggagga catctggaat gggagtacca gttttgtact ccaattgcat      1320
ctgcctggtt acttaaggat gggaaagtca ttcccatcag tcttttttgat gatacaagtt      1380 atacatctaa tgatgatgtt ttagaagatg aagaagacat tgtagaagct gccagaggag      1440
ccacagaaaa cagtgtttac ttgggaatgt atagaggcca gctgtatctg cagtcatcag      1500
tcagaatttc agaaaagttt ccttcaagtc ccaaggcttt ggaatctgtc actaatgaaa      1560
acgcaattat tcctttacca acaatcaaat ggaaacccct taattcattct ccttccagaa      1620 ctcctgtctt ggtaggatct gatgaatttg acaaatgtct cagtaatgat aagttttctc      1680
atgaagaata tagtaatggt gcactttcaa tcttgcagta tccatatgat aatggttatt      1740
atctaccata ctacaagagg gagaggcaca aacgaagcac acagattaca gtcagattcc      1800
tcgacaaccc acattacaac aagaatatcc gcaaaaagga tcctgttctt cttttacact      1860
ggtggaaaga aatagttgca acgatttttgt tttgtatcat agcaacaacg tttattgtgc      1920
gcaggctttt ccatcctcat cctcacaggc aaaggaagga gtctgaaact cagtgtcaaa      1980
ctgaaaataa atatgattct gtaagtggtg aagccaatga cagtagctgg aatgacataa      2040
aaaactctgg atatatatca cgatatctaa ctgattttga gccaattcaa tgcctgggac      2100
gtggtggctt tggagttgtt tttgaagcta aaacaaagt agatgactgc aattatgcta      2160
tcaagaggat ccgtctcccc aatagggaat tggctcggga aaaggtaatg cgagaagtta      2220
aagccttagc caagcttgaa cacccgggca ttgttagata tttcaatgcc tggctcgaag      2280
caccaccaga gaagtggcaa gaaaagatgg atgaaatttg gctgaaagat gaaagcacag      2340
actggccact cagctctcct agcccaatgg atgcaccatc agttaaaata cgcagaatgg      2400 atccttttctc tacaaaagaa catattgaaa tcatagctcc ttcaccacaa gaagcaggt       2460 cttttttcagt agggatttcc tgtgaccaga caagttcatc tgagagccag ttctcaccac      2520
tggaattctc aggaatggac catgaggaca tcagtgagtc agtggatgca gcatacaacc      2580
tccaggacag ttgccttaca gactgtgatg tggaagatgg gactatggat ggcaatgatg      2640
aggggcactc ctttgaactt tgtccttctg aagcttctcc ttatgtaagg tcaagggaga      2700
gaacctcctc ttcaatagta tttgaagatt ctggctgtga taatgcttcc agtaaagaag      2760
agccgaaaac taatcgattg catattggca accattgtgc taataaacta actgctttca      2820
agcccaccag tagcaaatct tcttctgaag ctacattgtc tatttctcct ccaagaccaa      2880
ccactttaag tttagatctc actaaaaaca ccacagaaaa actccagccc agttcaccaa      2940
aggtgtatct ttacattcaa atgcagctgt gcagaaaaga aaacctcaaa gactggatga      3000
atggacgatg taccatagag gagagagaga ggagcgtgtg tctgcacatc ttcctgcaga      3060
tcgcagaggc agtggagttt cttcacagta aaggactgat gcacagggac ctcaagccat      3120
ccaacatatt ctttacaatg gatgatgtgg tcaaggttgg agactttggg ttagtgactg      3180
caatggacca ggatgaggaa gagcagacgg ttctgacccc aatgccagct tatgccagac      3240
acacaggaca agtagggacc aaaactgtata tgagcccaga gcagattcat ggaaacagct      3300
attctcataa agtggacatc ttttctttag gcctgattct atttgaattg ctgtatccat      3360
```

| | |
|---|---|
| tcagcactca gatggagaga gtcaggacct taactgatgt aagaaatctc aaatttccac | 3420 |
| cattatttac tcagaaatat ccttgtgagt acgtgatggt tcaagacatg ctctctccat | 3480 |
| cccccatgga acgacctgaa gctataaaca tcattgaaaa tgctgtattt gaggacttgg | 3540 |
| actttccagg aaaaacagtg ctcagacaga ggtctcgctc cttgagttca tcgggaacaa | 3600 |
| aacattcaag acagtccaac aactcccata gcccttgcc aagcaattag ccttaagttg | 3660 |
| tgctagcaac cctaataggt gatgcagata atagcctact tcttagaata tgcctgtcca | 3720 |
| aaattgcaga cttgaaaagt ttgttcttcg ctcaattttt ttgtggacta cttttttat | 3780 |
| atcaaattta agctggatt gggggcataa cctaatttga gccaactcct gagttttgct | 3840 |
| atacttaagg aaagggctat ctttgttctt tgttagtctc ttgaaactgg ctgctggcca | 3900 |
| agctttatag ccctcaccat ttgcctaagg aggtagcagc aatccctaat atatatat | 3960 |
| agtgagaact aaaatggata tatttttata atgcagaaga aggaaagtcc ccctgtgtgg | 4020 |
| taactgtatt gttctagaaa tatgctttct agagatatga tgattttgaa actgatttct | 4080 |
| agaaaagct gactccattt ttgtcccctgg cgggtaaatt aggaatctgc actattttgg | 4140 |
| aggacaagta gcacaaactg tataacggtt tatgtccgta gttttatagt cctatttgta | 4200 |
| gcattcaata gctttattcc ttagatggtt ctagggtggg tttacagctt tttgtacttt | 4260 |
| tacctccaat aaagggaaaa tgaagctttt tatgtaaatt ggttgaaagg tctagtttg | 4320 |
| ggaggaaaaa agccgtagta agaaatggat catatatat acaactaact tcttcaacta | 4380 |
| tggactttt aagcctaatg aaatcttaag tgtcttatat gtaatcctgt aggttggtac | 4440 |
| ttcccccaaa ctgattatag gtaacagttt aatcatctca cttgctaaca tgtttttatt | 4500 |
| tttcactgta aatatgttta tgttttattt ataaaaattc tgaaatcaat ccatttgggt | 4560 |
| tggtggtgta cagaacacac ttaagtgtgt taacttgtga cttctttcaa gtctaaatca | 4620 |
| tttaataaaa cttttttaa attaaaaaaa aaaaaaaaaa aa | 4662 |

<210> SEQ ID NO 3
<211> LENGTH: 8404
<212> TYPE: DNA
<213> ORGANISM: Artificial Sequence
<220> FEATURE:
<223> OTHER INFORMATION: Synthetic

<400> SEQUENCE: 3

| | |
|---|---|
| ttggggttgc gccttttcca aggcagccct gggtttgcgc agggacgcgg ctgctctggg | 60 |
| cgtggttccg ggaaacgcag cggcgccgac cctgggtctc gcacattctt cacgtccgtt | 120 |
| cgcagcgtca cccggatctt cgccgctacc cttgtgggcc ccccggcgac gcttcctgct | 180 |
| ccgcccctaa gtcgggaagg ttccttgcgg ttcgcggcgt gccggacgtg acaaacggaa | 240 |
| gccgcacgtc tcactagtac cctcgcagac ggacagcgca agggagcaat ggcagcgcgc | 300 |
| cgaccgcgat gggctgtggc caatagcggc tgctcagcag ggcgcgccga gagcagcggc | 360 |
| cgggaagggg cggtgcggga ggcggggtgt ggggcggtag tgtgggccct gttcctgccc | 420 |
| gcgcggtgtt ccgcattctg caagcctccg gagcgcacgt cggcagtcgg ctccctcgtt | 480 |
| gaccgaatca ccgacctctc tccccagggg gatccaccgg agcttaccat gaccgagtac | 540 |
| aagcccacgg tgcgcctcgc caccgcgac gacgtcccca gggccgtacg caccctcgcc | 600 |
| gccgcgttcg ccgactaccc cgccacgcgc cacaccgtcg atccggaccg ccacatcgag | 660 |
| cgggtcaccg agctgcaaga actcttcctc acgcgcgtcg ggctcgacat cggcaaggtg | 720 |
| tgggtcgcgg acgacggcgc cgcggtggcg gtctggacca cgccggagag cgtcgaagcg | 780 |

```
ggggcggtgt tcgccgagat cggcccgcgc atggccgagt tgagcggttc ccggctggcc      840
gcgcagcaac agatggaagg cctcctggcg ccgcaccggc ccaaggagcc cgcgtggttc      900
ctggccaccg tcggcgtctc gcccgaccac cagggcaagg gtctgggcag cgccgtcgtg      960
ctccccggag tggaggcggc cgagcgcgcc ggggtgcccg ccttcctgga gacctccgcg     1020
ccccgcaacc tccccttcta cgagcggctc ggcttcaccg tcaccgccga cgtcgaggtg     1080
cccgaaggac cgcgcacctg gtgcatgacc cgcaagcccg gtgcctgacg cccgccccac     1140
gacccgcagc gcccgaccga aggagcgca cgaccccatg catcggtacc tttaagacca      1200
atgacttaca aggcagctgt agatcttagc cacttttta aagaaaaggg gggactggaa      1260
gggctaattc actcccaacg aagacaagat ctgcttttg cttgtactgg gtctctctgg      1320
ttagaccaga tctgagcctg ggagctctct ggctaactag ggaacccact gcttaagcct     1380
caataaagct tgccttgagt gcttcaagta gtgtgtgccc gtctgttgtg tgactctggt     1440
aactagagat ccctcagacc cttttagtca gtgtggaaaa tctctagcag tagtagttca     1500
tgtcatctta ttattcagta tttataactt gcaaagaaat gaatatcaga gagtgagagg     1560
aacttgttta ttgcagctta taatggttac aaataaagca atagcatcac aaatttcaca     1620
aataaagcat tttttcact gcattctagt tgtggtttgt ccaaactcat caatgtatct      1680
tatcatgtct ggctctagct atcccgcccc taactccgcc catcccgccc ctaactccgc     1740
ccagttccgc ccattctccg ccccatggct gactaatttt ttttatttat gcagaggccg     1800
aggccgcctc ggcctctgag ctattccaga agtagtgagg aggcttttt ggaggcctag     1860 ggacgtaccc aattcgccct atagtgagtc gtattacgcg cgctcactgg ccgtcgtttt    1920
acaacgtcgt gactgggaaa accctggcgt tacccaactt aatcgccttg cagcacatcc     1980 cccttcgcc agctggcgta atagcgaaga ggcccgcacc gatcgccctt cccaacagtt     2040
gcgcagcctg aatggcgaat gggacgcgcc ctgtagcggc gcattaagcg cggcgggtgt     2100
ggtggttacg cgcagcgtga ccgctacact tgccagcgcc ctagcgcccg ctccttcgc     2160 tttcttccct tcctttctcg ccacgttcgc cggctttccc cgtcaagctc taaatcgggg     2220
gctcccttta gggttccgat ttagtgcttt acggcacctc gaccccaaaa aacttgatta     2280
gggtgatggt tcacgtagtg gccatcgcc ctgatagacg gttttttcgcc ctttgacgtt    2340 ggagtccacg ttctttaata gtggactctt gttccaaact ggaacaacac tcaaccctat     2400
ctcggtctat tcttttgatt tataagggat tttgccgatt tcggcctatt ggttaaaaaa     2460
tgagctgatt taacaaaaat ttaacgcgaa ttttaacaaa atattaacgc ttacaattta     2520
ggtggcactt ttcggggaaa tgtgcgcgga acccctattt gtttattttt ctaaatacat     2580
tcaaatatgt atccgctcat gagacaataa ccctgataaa tgcttcaata atattgaaaa     2640
aggaagagta tgagtattca acatttccgt gtcgccctta ttcccttttt tgcggcattt     2700
tgccttcctg ttttgctca cccagaaacg ctggtgaaag taaaagatgc tgaagatcag     2760
ttgggtgcac gagtgggtta catcgaactg gatctcaaca gcggtaagat ccttgagagt     2820
tttcgccccg aagaacgttt tccaatgatg agcacttta aagttctgct atgtggcgcg     2880
gtattatccc gtattgacgc cgggcaagag caactcggtc gccgcataca ctattctcag     2940
aatgacttgg ttgagtactc accagtcaca gaaaagcatc ttacggatgg catgacagta     3000
agagaattat gcagtgctgc cataaccatg agtgataaca ctgcggccaa cttacttctg     3060
acaacgatcg gaggaccgaa ggagctaacc gcttttttgc acaacatggg ggatcatgta     3120
actcgccttg atcgttggga accggagctg aatgaagcca taccaaacga cgagcgtgac     3180
```

```
accacgatgc ctgtagcaat ggcaacaacg ttgcgcaaac tattaactgg cgaactactt    3240
actctagctt cccggcaaca attaatagac tggatggagg cggataaagt tgcaggacca    3300
cttctgcgct cggcccttcc ggctggctgg tttattgctg ataaatctgg agccggtgag    3360
cgtgggtctc gcggtatcat tgcagcactg gggccagatg gtaagccctc ccgtatcgta    3420
gttatctaca cgacggggag tcaggcaact atggatgaac gaaatagaca gatcgctgag    3480
ataggtgcct cactgattaa gcattggtaa ctgtcagacc aagtttactc atatatactt    3540
tagattgatt taaaacttca ttttttaattt aaaaggatct aggtgaagat cctttttgat    3600
aatctcatga ccaaaatccc ttaacgtgag ttttcgttcc actgagcgtc agaccccgta    3660
gaaaagatca aggatcttc ttgagatcct ttttttctgc gcgtaatctg ctgcttgcaa    3720
acaaaaaaac caccgctacc agcggtggtt tgtttgccgg atcaagagct accaactctt    3780
tttccgaagg taactggctt cagcagagcg cagataccaa atactgttct tctagtgtag    3840
ccgtagttag gccaccactt caagaactct gtagcaccgc ctacatacct cgctctgcta    3900
atcctgttac cagtggctgc tgccagtggc gataagtcgt gtcttaccgg gttggactca    3960
agacgatagt taccggataa ggcgcagcgg tcgggctgaa cggggggttc gtgcacacag    4020
cccagcttgg agcgaacgac ctacaccgaa ctgagatacc tacagcgtga gctatgagaa    4080
agcgccacgc ttcccgaagg gagaaaggcg gacaggtatc cggtaagcgg cagggtcgga    4140
acaggagagc gcacgaggga gcttccaggg ggaaacgcct ggtatcttta tagtcctgtc    4200
gggtttcgcc acctctgact tgagcgtcga ttttttgtgat gctcgtcagg ggggcggagc    4260
ctatggaaaa acgccagcaa cgcggccttt ttacggttcc tggccttttg ctggcctttt    4320
gctcacatgt tctttcctgc gttatcccct gattctgtgg ataaccgtat taccgccttt    4380
gagtgagctg ataccgctcg ccgcagccga acgaccgagc gcagcgagtc agtgagcgag    4440
gaagcggaag agcgcccaat acgcaaaccg cctctccccg cgcgttggcc gattcattaa    4500
tgcagctggc acgacaggtt cccgactgg aaagcgggca gtgagcgcaa cgcaattaat    4560
gtgagttagc tcactcatta ggcaccccag gctttacact ttatgcttcc ggctcgtatg    4620
ttgtgtggaa ttgtgagcgg ataacaattt cacacaggaa acagctatga ccatgattac    4680
gccaagcgcg caattaaccc tcactaaagg gaacaaaagc tggagctgca agcttaatgt    4740
agtcttatgc aatactcttg tagtcttgca acatggtaac gatgagttag caacatgcct    4800
tacaaggaga gaaaaagcac cgtgcatgcc gattggtgga agtaaggtgg tacgatcgtg    4860
ccttattagg aaggcaacag acgggtctga catggattgg acgaaccact gaattgccgc    4920
attgcagaga tattgtattt aagtgcctag ctcgatacat aaacgggtct ctctggttag    4980
accagatctg agcctgggag ctctctggct aactagggaa cccactgctt aagcctcaat    5040
aaagcttgcc ttgagtgctt caagtagtgt gtgcccgtct gttgtgtgac tctggtaact    5100
agagatccct cagacccttt tagtcagtgt ggaaaatctc tagcagtggc gcccgaacag    5160
ggacttgaaa gcgaaaggga accagagga gctctctcga cgcaggactc ggcttgctga    5220
agcgcgcacg gcaagaggcg aggggcggcg actggtgagt acgccaaaaa ttttgactag    5280
cggaggctag aaggagagag atgggtgcga gagcgtcagt attaagcggg ggagaattag    5340
atcgcgatgg gaaaaaattc ggttaaggcc agggggaaag aaaaaatata aattaaaaca    5400
tatagtatgg gcaagcaggg agctagaacg attcgcagtt aatcctggcc tgttagaaac    5460
atcacgaagg ctgtagacaa atactgggac agctacaacc atcccttcag acaggatcag    5520
aagaacttac atcattatat aatacagtag caaccctcta ttgtgtgcat caaaggatag    5580
```

-continued

```
agataaaaga caccaaggaa gctttagaca agatagagga agagcaaaac aaaagtaaga    5640
ccaccgcaca gcaagcggcc gctgatcttc agacctggag gaggagatat gagggacaat    5700
tggagaagtg aattatataa atataaagta gtaaaaattg aaccattagg agtagcaccc    5760
accaaggcaa agagaagagt ggtgcagaga gaaaaaagag cagtgggaat aggagctttg    5820
ttccttgggt tcttgggagc agcaggaagc actatgggcg cagcgtcaat gacgctgacg    5880
gtacaggcca gacaattatt gtctggtata gtgcagcagc agaacaattt gctgagggct    5940
attgaggcgc aacagcatct gttgcaactc acagtctggg gcatcaagca gctccaggca    6000
agaatcctgg ctgtggaaag atacctaaag gatcaacagc tcctggggat ttggggttgc    6060
tctgaaaaac tcatttgcac cactgctgtg ccttggaatg ctagttggag taataaatct    6120
ctggaacaga tttggaatca cacgacctgg atggagtggg acagagaaat taacaattac    6180
acaagcttaa tacactcctt aattgaagaa tcgcaaaacc agcaagaaaa gaatgaacaa    6240
gaattattgg aattagataa atgggcaagt ttgtggaatt ggtttaacat aacaaattgg    6300
ctgtggtata taaaaattat tcataatgat agtaggaggc ttggtaggtt taagaatagt    6360
ttttgctgta ctttctatag tgaatagagt taggcaggga tattcaccat tatcgtttca    6420
gacccacctc ccaaccccga ggggacccga caggcccgaa ggaatagaag aagaaggtgg    6480
agagagagac agagacagat ccattcgatt agtgaacgga tctcgacggt atcgatcacg    6540
agactagcct cgagcggccg ccccttcac cgagggccta tttcccatga ttccttcata    6600
tttgcatata cgatacaagg ctgttagaga gataattgga attaatttga ctgtaaacac    6660
aaagatatta gtacaaaata cgtgacgtag aaagtaataa tttcttgggt agtttgcagt    6720
tttaaaatta tgtttttaaaa tggactatca tatgcttacc gtaacttgaa agtatttcga    6780
tttcttggct ttatatatct tgtggaaagg acgaaacacc ggccactttg aacttcggta    6840
tactcgagta taccgaagtt caaagtggct ttttgaattc agttattaat agtaatcaat    6900 tacgggggtca ttagttcata gcccatatat ggagttccgc gttacataac ttacggtaaa    6960
tggcccgcct ggctgaccgc ccaacgaccc ccgcccattg acgtcaataa tgacgtatgt    7020
tcccatagta acgccaatag ggactttcca ttgacgtcaa tgggtggagt atttacggta    7080
aactgcccac ttggcagtac atcaagtgta tcatatgcca agtacgcccc ctattgacgt    7140
caatgacggt aaatggcccg cctggcatta tgcccagtac atgaccttat gggactttcc    7200
tacttggcag tacatctacg tattagtcat cgctattacc atggtgatgc ggttttggca    7260
gtacatcaat gggcgtggat agcggtttga ctcacgggga tttccaagtc tccaccccat    7320
tgacgtcaat gggagtttgt tttggcacca aaatcaacgg gactttccaa aatgtcgtaa    7380
caactccgcc ccattgacgc aaatgggcgg taggcgtgta cggtgggagg tctatataag    7440
cagagctggt ttagtgaacc gtcagatccg ctagcgctcc cggtcgccac catggagagc    7500
gacgagagcg gcctgcccgc catggagatc gagtgccgca tcaccggcac cctgaacggc    7560
gtggagttcg agctggtggg cggcggagag ggcacccccg agcagggccg catgaccaac    7620
aagatgaaga gcaccaaagg cgccctgacc ttcagcccct acctgctgag ccacgtgatg    7680
ggctacggct tctaccactt cggcacctac cccagcggct acgagaaccc cttcctgcac    7740
gccatcaaca cggcggcta caccaacacc cgcatcgaga agtacgagga cggcggcgtg    7800
ctgcacgtga gcttcagcta ccgctacgag gccggccgcg tgatcggcga cttcaaggtg    7860
atgggcaccg gcttccccga ggacagcgtg atcttcaccg acaagatcat ccgcagcaac    7920
gccaccgtgg agcacctgca ccccatgggc gataacgatc tggatggcag cttcacccgc    7980
```

| | | | | | | |
|---|---|---|---|---|---|---|
| accttcagcc | tgcgcgacgg | cggctactac | agctccgtgg | tggacagcca | catgcacttc | 8040 |
| aagagcgcca | tccacccag | catcctgcag | aacgggggcc | ccatgttcgc | cttccgccgc | 8100 |
| gtggaggagg | atcacagcaa | caccgagctg | ggcatcgtgg | agtaccagca | cgccttcaag | 8160 |
| accccggatg | cagatgccgg | tgaagaataa | aattaattct | cgacctcgag | acaaatggca | 8220 |
| gtattcatcc | acaattttaa | aagaaaaggg | gggattgggg | ggtacagtgc | aggggaaaga | 8280 |
| atagtagaca | taatagcaac | agacatacaa | actaaagaat | tacaaaaaca | aattacaaaa | 8340 |
| attcaaaatt | ttcgggttta | ttacagggac | agcagagatc | cactttggcc | gcggctcgag | 8400 |
| gggg | | | | | | 8404 |

GENETIC OR PHARMACOLOGICAL REDUCTION OF PERK ENHANCES CORTICAL- AND HIPPOCAMPUS-DEPENDENT COGNITIVE FUNCTION

CROSS-REFERENCE TO RELATED PATENT APPLICATIONS

This application claims priority under 35 U.S.C. § 119(e) from U.S. provisional patent application No. 62/247,255, filed on Oct. 28, 2015, which is incorporated herein by reference in its entirety.

FIELD OF THE INVENTION

The present invention relates in general to methods for improvement of cognitive function.

BACKGROUND OF THE INVENTION

With the growing population of senior citizens, one of the major health and social problems of modern times is the decline in cognitive function in ageing and neurodegenerative disease. Currently, the approach for improving cognitive function involves pharmacological intervention targeting neurotransmitter pathways believed to be involved in the process of memory formation with the aim of increasing neurotransmitter level and thus improve signal transmission. However, these therapies are at best symptomatic or supportive. A different and promising approach is described in US 2011/0052566, teaching methods for improving cognitive function by inhibition of the kinase activity of protein kinase R (PKR).

However, there still remains an unmet need for therapies and methods for treating cognitive impairment. The need for improving cognition is not a prerogative only of cognitively impaired patients but may also be desired by normally functioning individuals desiring to improve learning and memory.

SUMMARY OF INVENTION

In one aspect, the present invention provides a method for improving a cognitive function in a subject comprising administering to said subject an active agent reducing PKR-like endoplasmic reticulum kinase (PERK) activity.

In a further aspect, the present invention provides a pharmaceutical composition comprising an active agent or a vector as defined herein, and a pharmaceutically acceptable carrier.

In an additional aspect, the present invention provides a method for improving cognition in a subject comprising administering compound 1 or compound 6 to the subject.

In yet another aspect, the present invention is directed to a method for improving cognition in a subject comprising administering to the subject a modified lentivirus vector comprising a nucleic acid molecule encoding an shRNA molecule comprising a sequence being complementary to a sequence within a nucleic acid sequence encoding the PERK.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
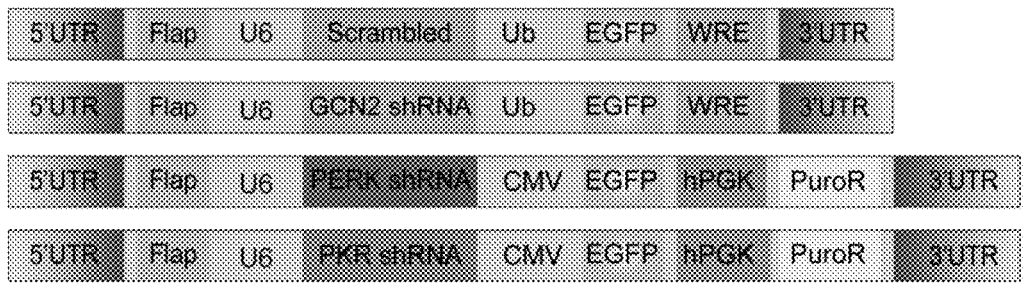
FIG. 1 shows that PERK is the major kinase to determine basal levels of phosphorylated eIF2α (p-eIF2α). A. schematic description of the plasmids used to generate lentiviruses. B. Immunoblot quantification of the specific target is expressed as the ratio of target specific antibody/actin. n=4, *p=0.02 for PERK, p=0.01 for GCN2, and p=0.04 for PKR, t-test. C. eIF2α phosphorylation is expressed as the ratio between anti-phospho eIF2α antibody (Ser51) and anti-eIF2α antibody; results were normalized to scrambled sequence control vector (SCR)-infected 3T3 cells, (n=4, p=0.007 Student's t-test), data are mean±SEM). D. eIF2α phosphorylation is expressed as the ratio between antiphospho eIF2α antibody (Ser51) and anti-eIF2α antibody; results were normalized to SCR-infected primary neuronal cells (n=5-10, *p=0.03, Students t-test), data are mean±SEM.
Figure 1:
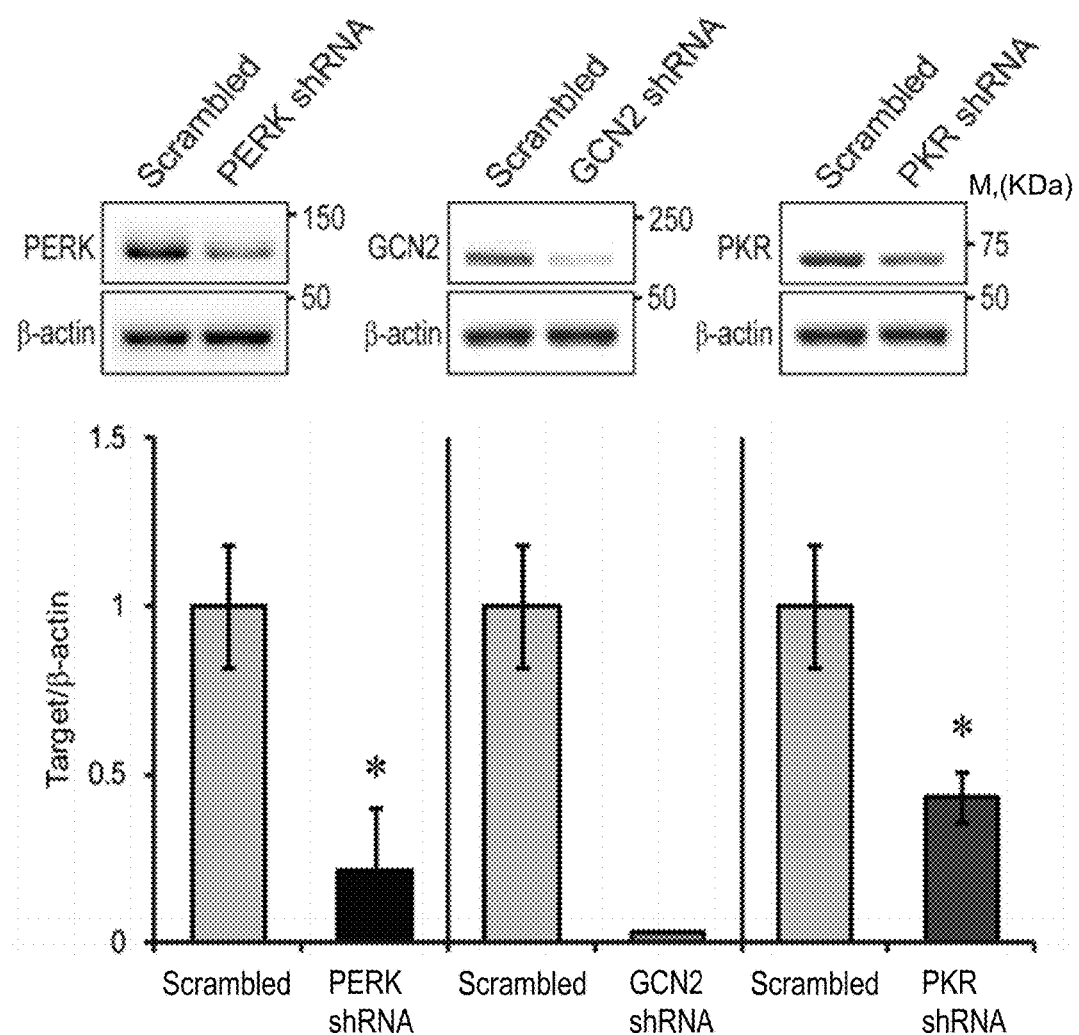
Figure 1:
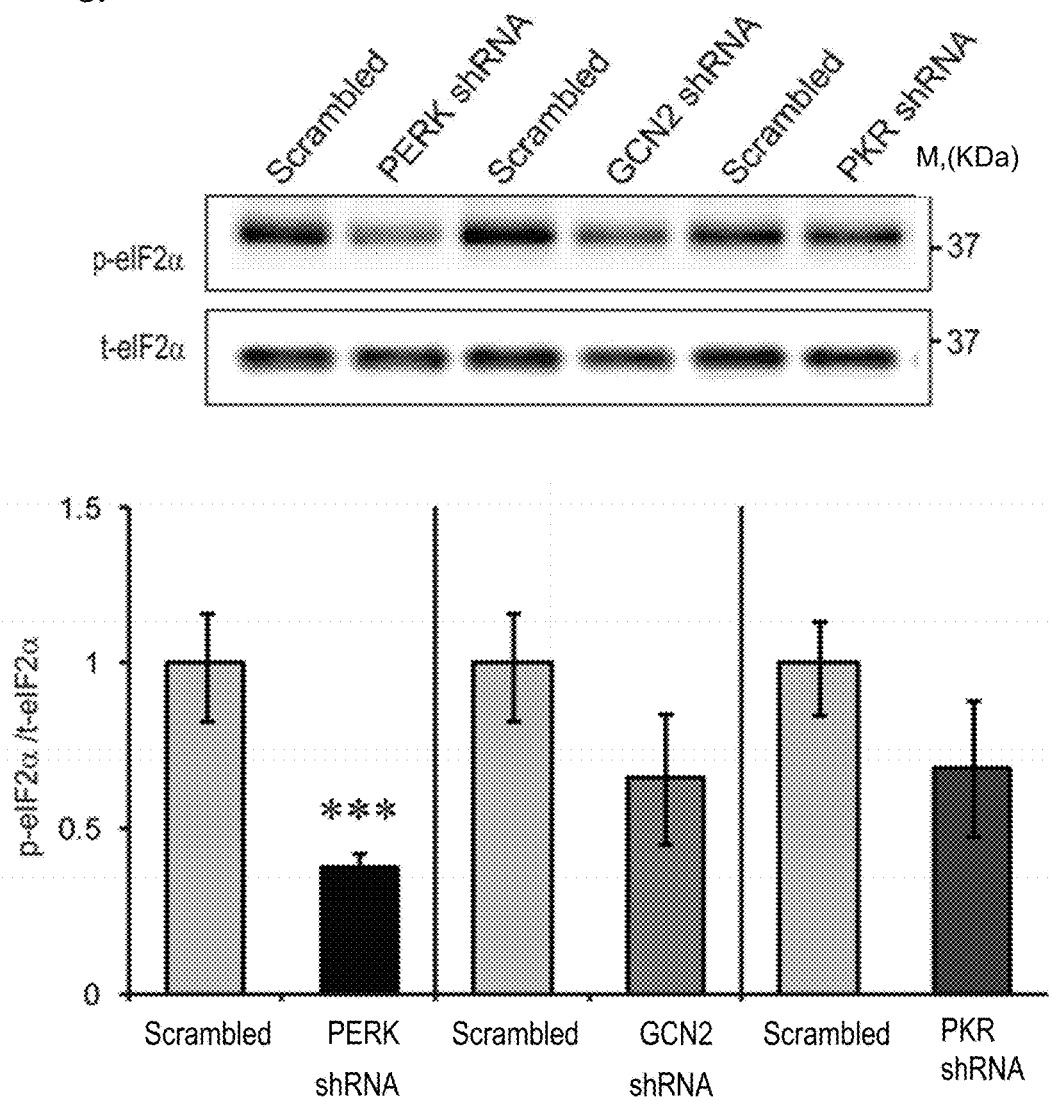
Figure 1:
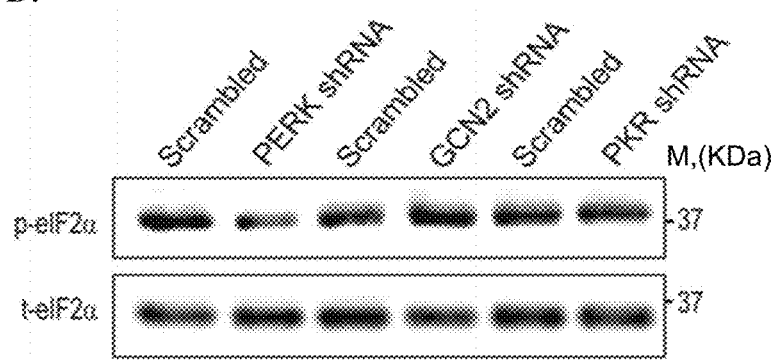
Figure 1:
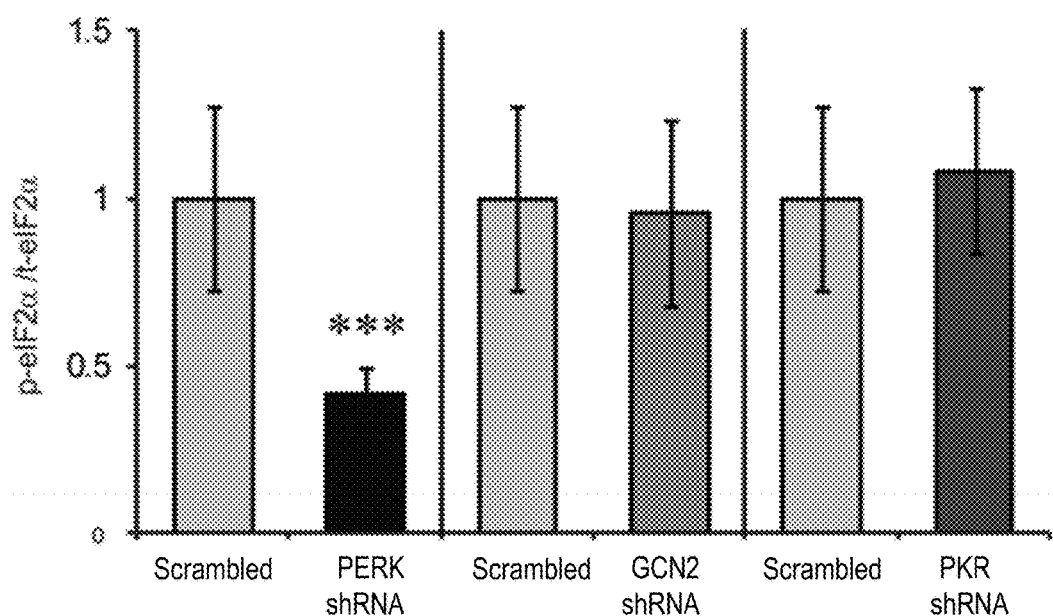

Translation of mRNA into protein can be divided to three phases: initiation, elongation, and termination, where both the initiation and elongation phases are vital for memory consolidation (Gal-Ben-Ari et al., 2012). The transition from short- to long-term memory and synaptic plasticity is regulated by phosphorylation of eukaryotic initiation factor 2 (eIF2) at Serine 51 of its α subunit (p-eIF2α). Specifically, reduction in p-eIF2α levels results in facilitation of long-term memory formation, while an increase results in memory impairment (Costa-Mattioli et al., 2007). From a biochemical perspective, eIF2α phosphorylation reduces translation of most mRNAs, but paradoxically stimulates translation of mRNAs harboring upstream open reading frames (uORFs) in their 5'UTR, such as activating transcription factor 4 (ATF4) and beta-secretase 1 (BACE1).

In the brain, eIF2α can be phosphorylated by three well-described kinases: 1—protein kinase RNA-activated (PKR, a double-stranded RNA-dependent protein kinase); 2—PKR-like endoplasmic reticulum kinase (PERK); and 3—general control nonderepressible 2 (GCN2) (Gal-Ben-Ari et al., 2012). Of these three kinases, PERK is the major one to determine basal p-eIF2α levels (Moreno et al., 2012; Ounallah-Saad et al., 2014; Trinh et al., 2012).

The role of PERK in synaptic plasticity and hippocampal-dependent memory has been studied using a PERK conditional KO (cKO) mouse model, where PERK is deleted specifically in excitatory neurons. In these mice, overall memory strength is not affected. However, behavioral flexibility is impaired, a finding attributed to facilitated mGluR-long term depression (mGluR-LTD) (Trinh et al., 2012; Trinh et al., 2014). Paradoxically, as has been found in accordance with the present invention, knock down of PERK in the cortex of adult rats resulted in enhanced memory and enhanced behavioral flexibility (Ounallah-Saad et al., 2014).

In addition to the function of PERK in learning and memory processes, it has also been implicated in age-dependent brain diseases. For example, decreasing p-eIF2α by decreasing PERK activity or expression levels has been shown to rescue neurodegeneration in prion disease as well as memory deficits in the APP/PS1 Alzheimer's disease (AD) mouse models that overproduce Aβ (Ma et al., 2013; Moreno et al., 2013; Radford et al., 2015).

Brain aging also alters calcium homeostasis, which can negatively affect neuronal function. For example, aging is correlated with reduced neuronal excitability that can be measured via modulation in afterhyperpolarization (AHP) and accommodation of hippocampal neurons (Disterhoft and Oh, 2006; 2007). Moreover, with age, mAHP in CA1 neurons is significantly larger, thus causing lower neural excitability in aged rats (Oh et al., 2010). However, the role of PERK in synaptic plasticity in aging remains unexplored.

In line with the dual functions of PERK in normal learning processes and aging-dependent brain diseases, we tested two hypotheses: first, we tested the hypothesis that locally reduced PERK activity or expression in the CA1 region of the hippocampus results in better long-term memory. Second, we tested the hypothesis that reducing PERK in the CA1 region of aged mice would have an ameliorating effect on both the declined cognitive performance and intrinsic neuronal excitability.

Figure 2:
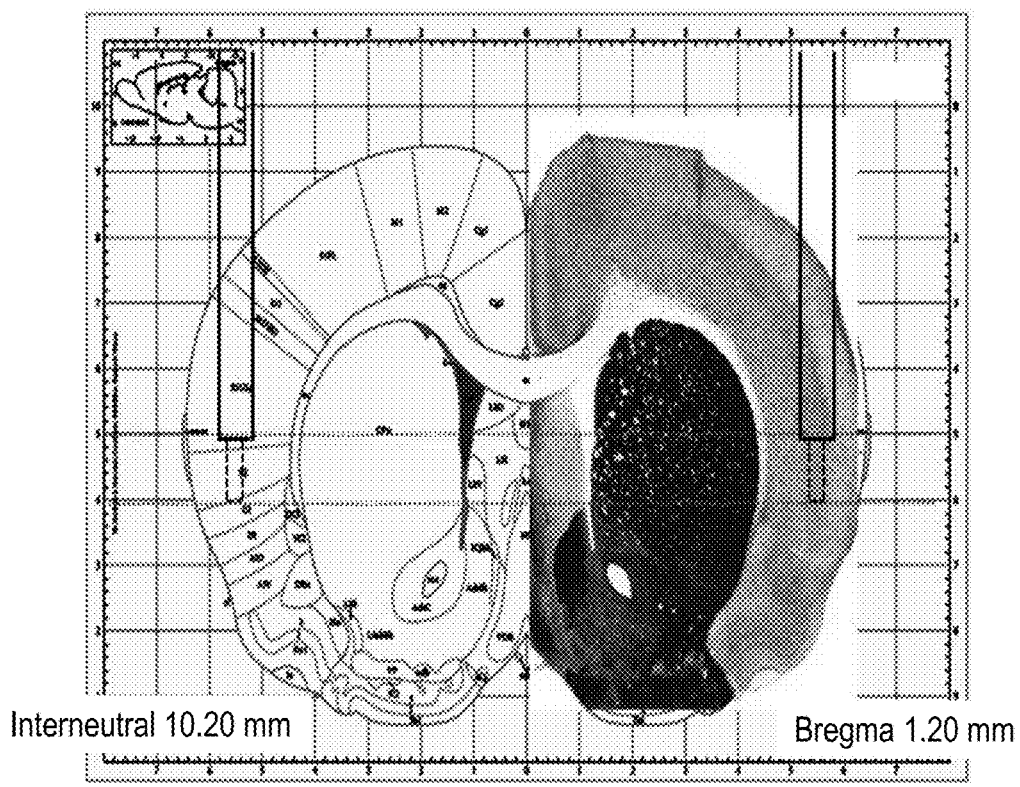
FIG. 2 shows that local PERK inhibition (GSK2606414) in the insular cortex (IC) enhances memory. A. A representative slice with Nissl staining shows the position of the cannula and the injection site. B. Taste memory is enhanced following PERK inhibition. PERK inhibitor (GSK2606414, 100 nM) was injected sterotaxically into the rat IC 20 min prior to novel taste drinking (saccharin, 0.1%). PERK inhibition enhances memory of the novel taste compared with vehicle group (n=8 per group, *p=0.04, t-test). C. PERK inhibitor (GSK2606414) was injected 20 min prior to NaCl (0.3%) drinking. CTA was carried out as usual. PERK inhibition enhances CTA memory vs. vehicle group, and extinction was not influenced (n=8 per group, *p=0.04 t-test). Data are mean±SEM. Top diagrams are schematic description of the behavioral procedures, blue pipettes indicate water, red pipettes indicate saccharin, and yellow pipettes indicate 0.3% NaCl.
Figure 2:
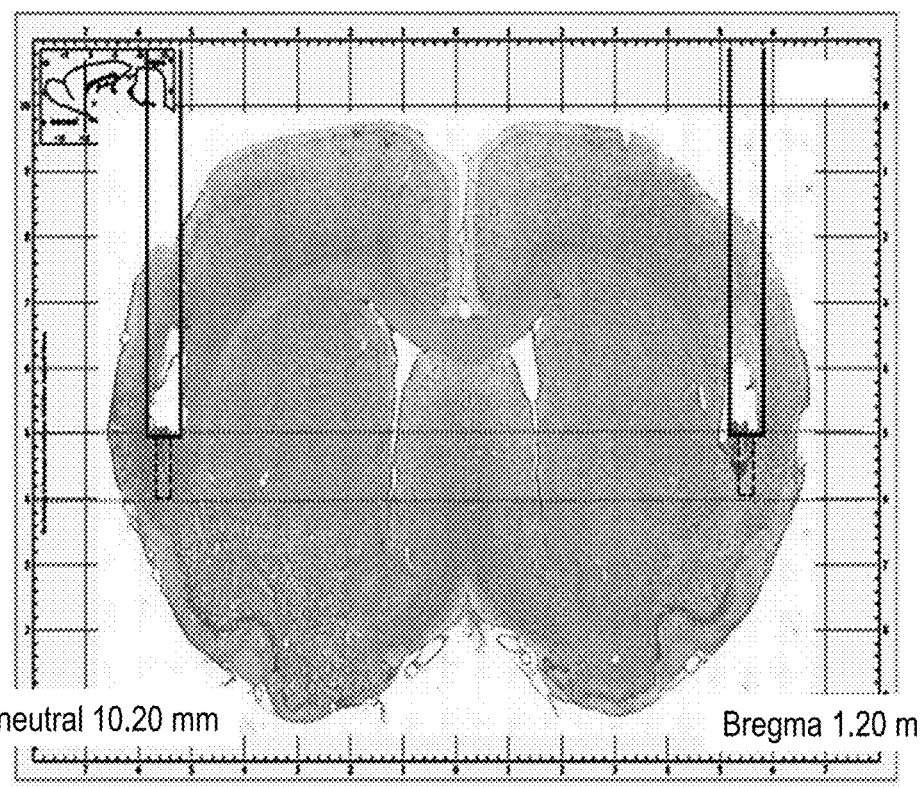
Figure 2:
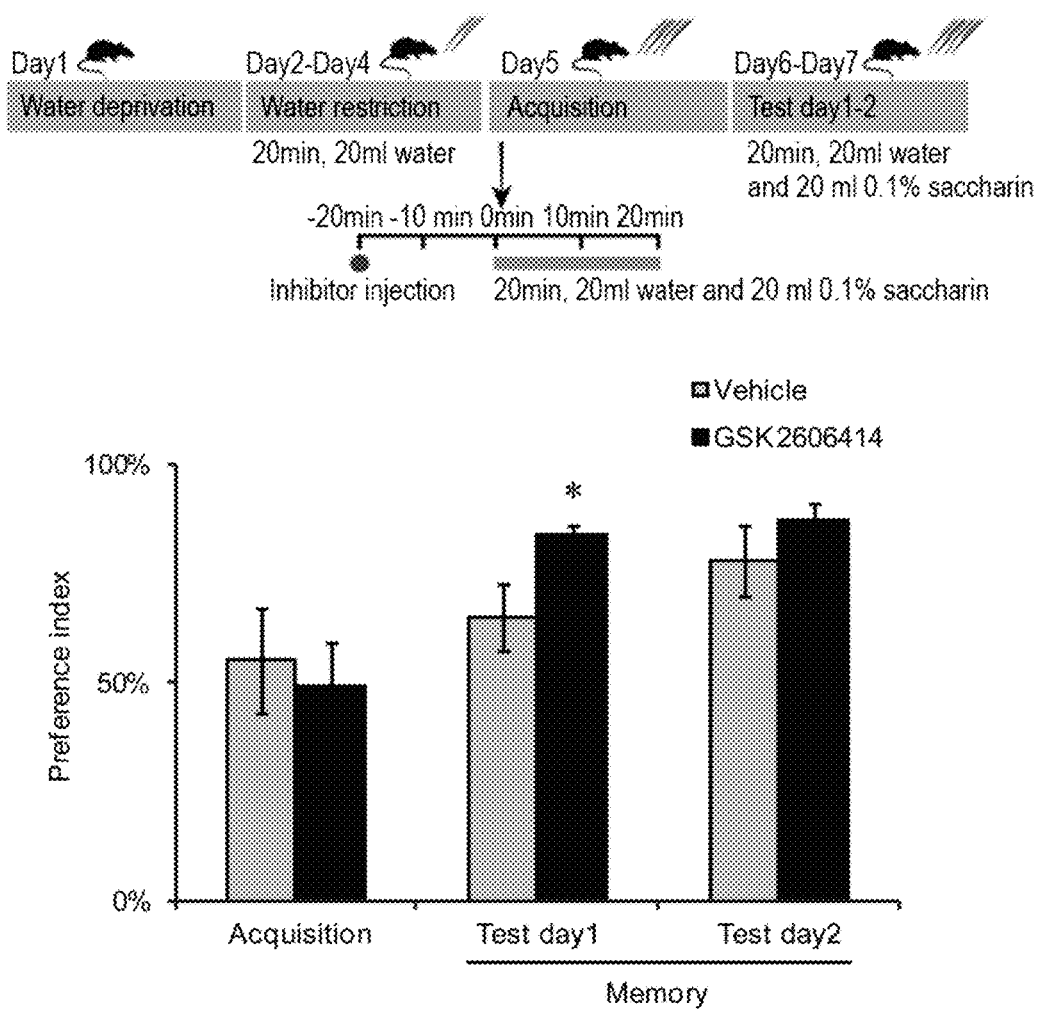
Figure 2:
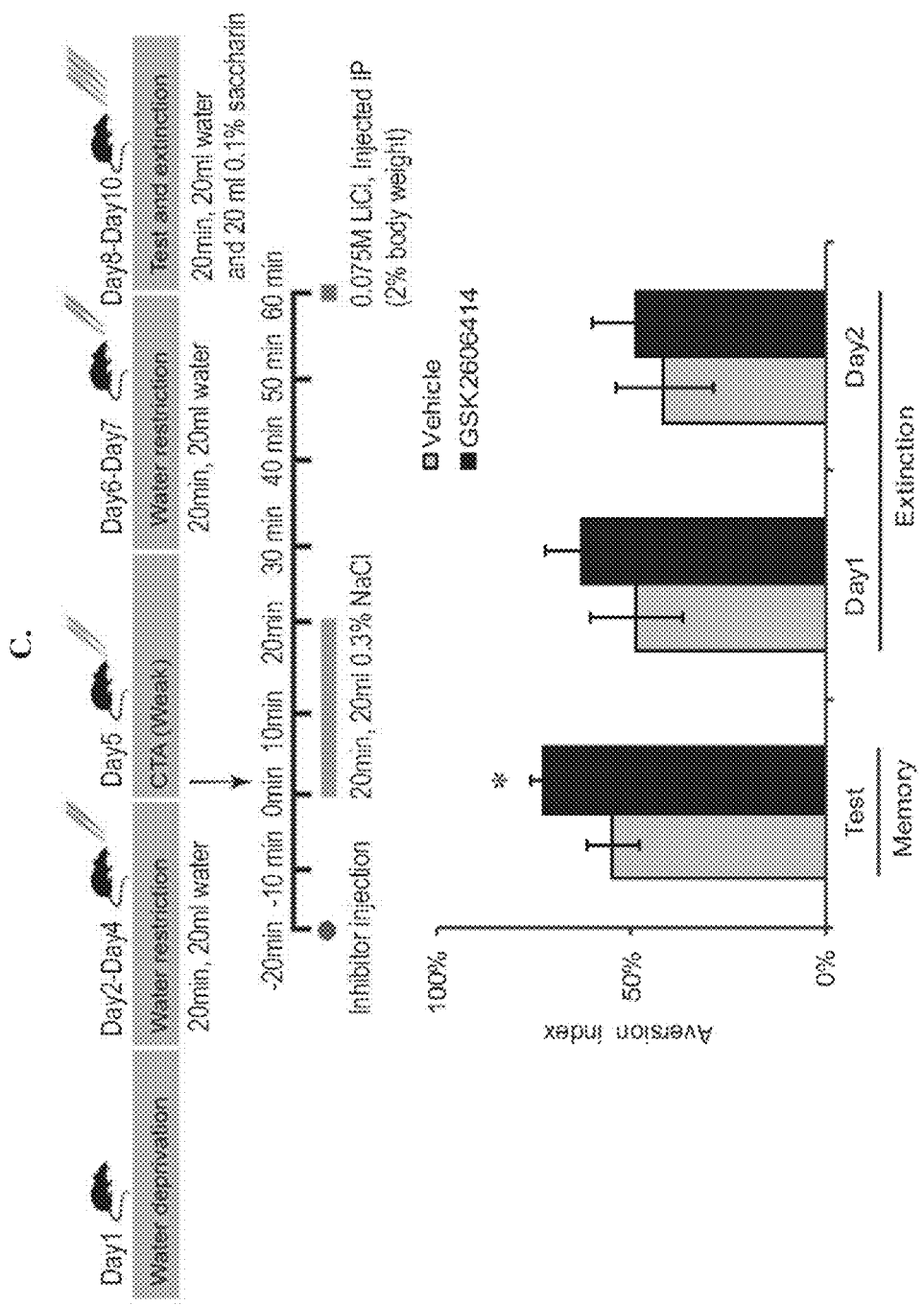
Figure 3:
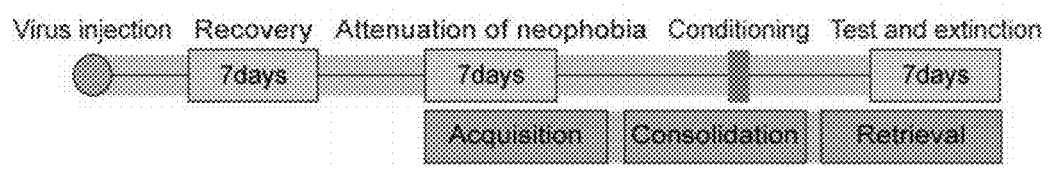
FIG. 3 shows that knockdown of PERK in the IC enhances behavioral plasticity. A. Schematic description of the experimental procedure. B. A representative slice with neuronal nuclear staining (NeuN) co-localized with native GFP, indicating the virus injection site and proper expression. C. Novel taste (saccharin 0.1%) learning is enhanced in PERK shRNA lentivirus-injected rats as expressed by the increase in preference index (PERK shRNA lentivirus, n=21; SCR controls, n=21). Results were analyzed using Friedman's test, followed by post hoc analysis using Wilcoxon signed-rank tests with a Bonferroni correction applied (p=0.005 for test day 1, and p=0.001 for test day 2. Data are mean±SEM). D. CTA memory is enhanced in PERK shRNA lentivirus injected rats (n=21) compared with scrambled sequence shRNA lentivirus-injected controls (n=21). Extinction of CTA was improved in PERK shRNA lentivirus-injected rats, as demonstrated by the reduction in aversion index. Memory day was analyzed using t-test (*p=0.0003). Extinction of CTA was analyzed with repeated measures ANOVA (***#p=0.001 for day 1 extinction and 0.0001 for day 2 extinction. Data are mean±SEM). Top diagrams are schematic description of the behavioral procedure, blue pipettes indicate water, red pipettes indicate saccharin, and yellow pipettes indicate 0.3% NaCl. E. Immunoblot analysis of the changes in PERK and p-eIF2α levels following virus injection to the IC demonstrates significant reduction in PERK levels (left, n=12, p=0.02), and significant reduction in p-eIF2α levels (right, n=17, p=0.01).
Figure 3:
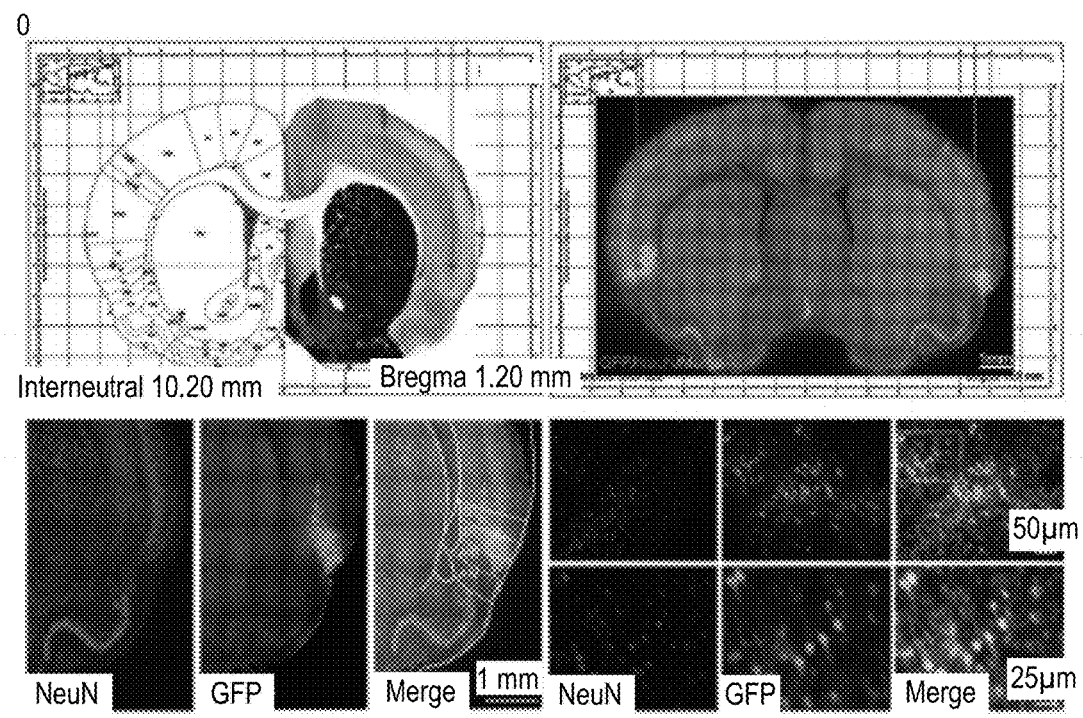
Figure 3:
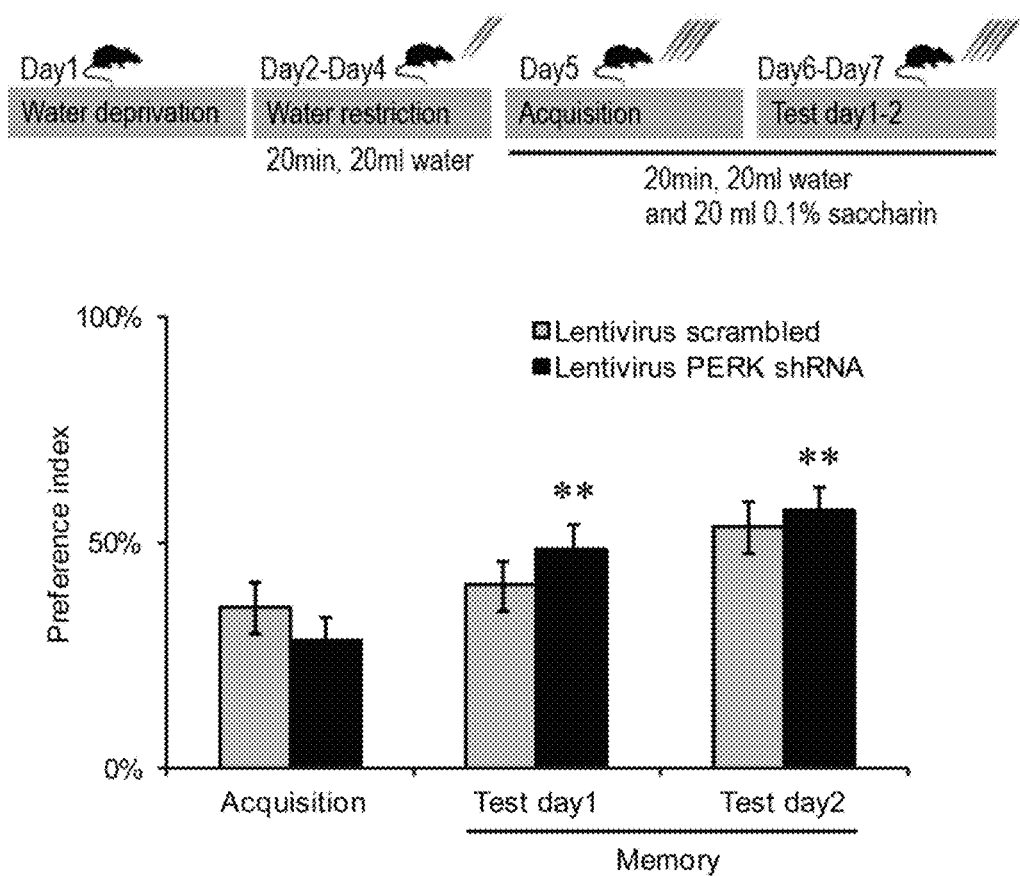
Figure 3:
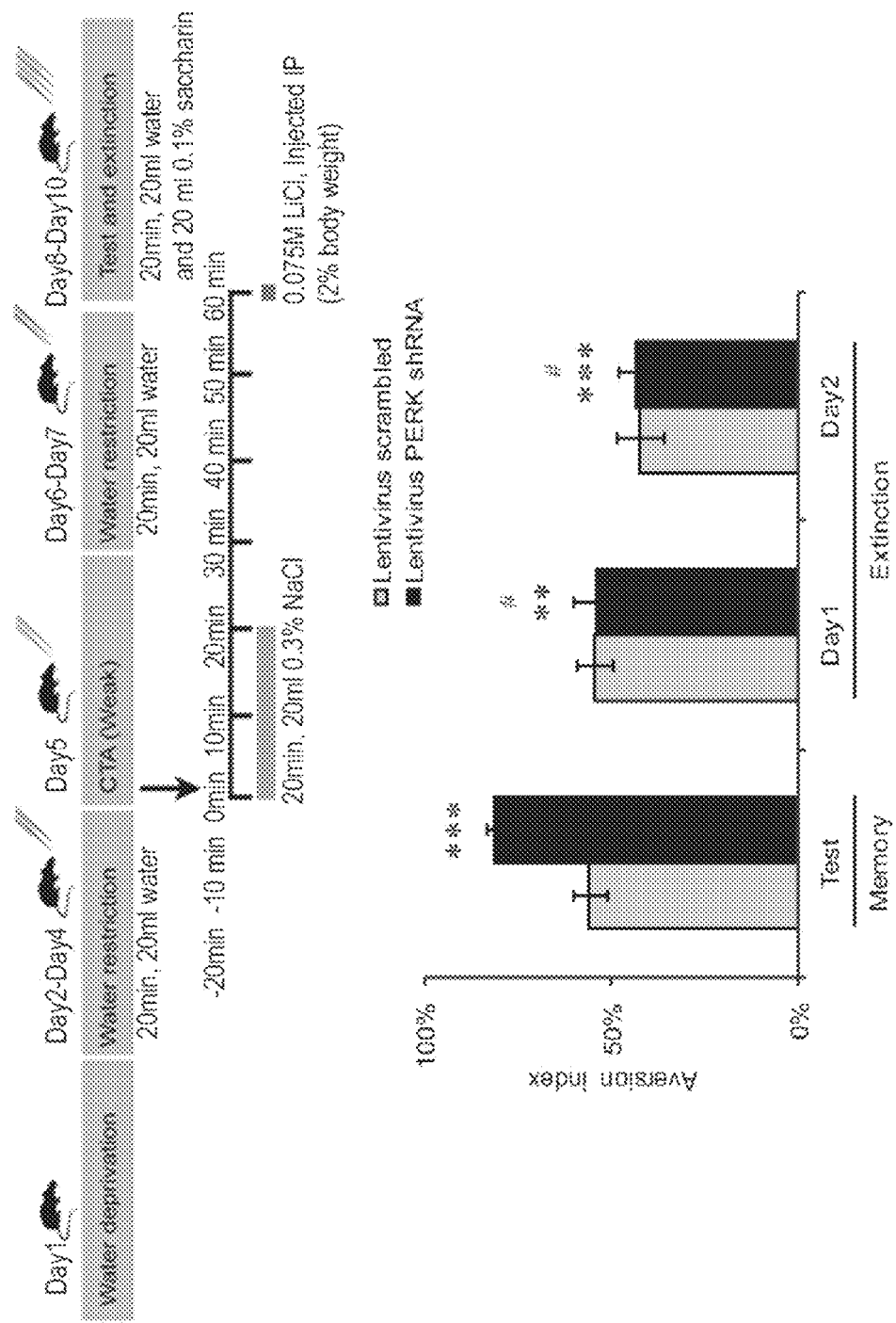
Figure 3:
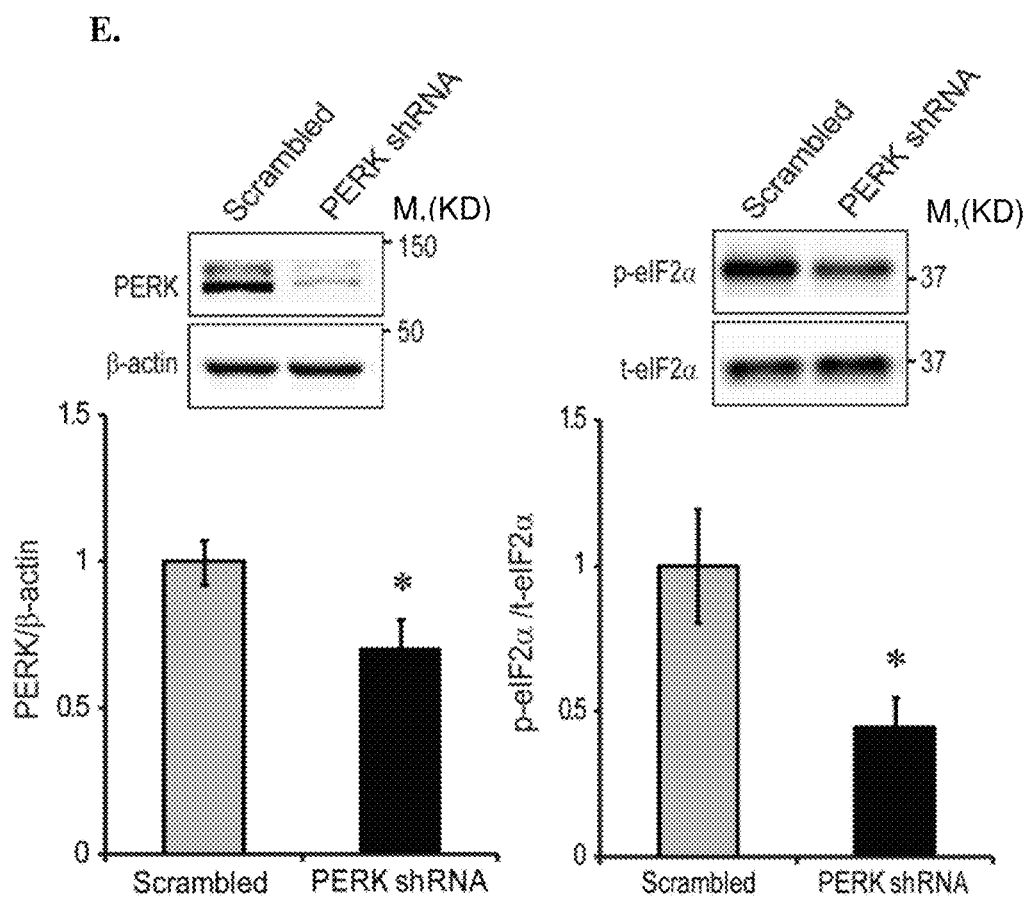
Figure 4:
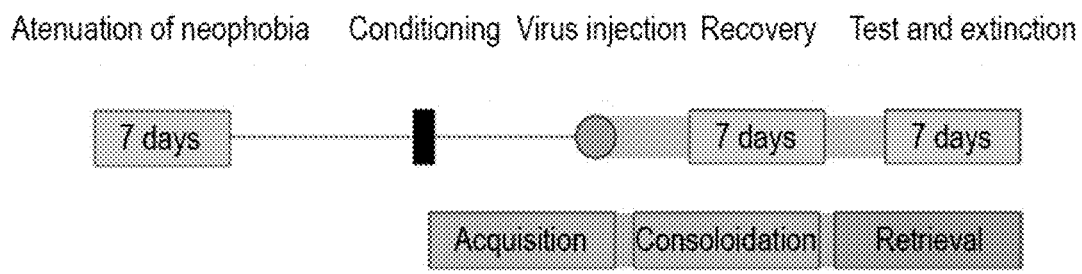
FIG. 4 shows that PERK knockdown enhances memory at the consolidation phase, but does not affect retrieval. A. A schematic description of the experimental procedure. B. CTA was performed 2 days prior to virus injection and PERK knockdown. Memory test and extinction assessment were performed 1 week following injection. There are no differences in memory between scrambled shRNA lentivirus- and PERK shRNA lentivirus-injected (n=8 per group), and there is a trend for improved extinction. Top diagram represents a schematic description of the behavioral procedure.
Figure 4:
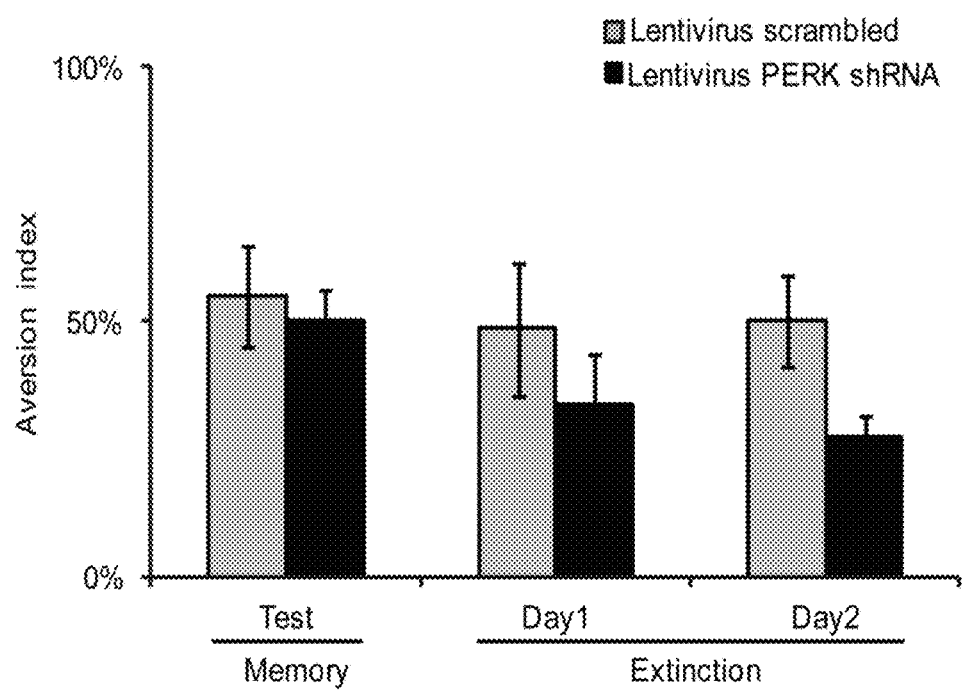

The present invention is thus based on the finding that under basal conditions PERK is the predominant kinase to determine p-eIF2α levels (FIG. 1), and that inhibition of PERK activity (using GSK2606414; referred to herein as compound 6) (Axten et al., 2012) and PERK knockdown, i.e. reduction in the amount of PERK, (using a specific shRNA lentivirus) in the insular cortex (IC) results in enhanced taste memory in both positive and negative forms of taste learning, namely incidental taste learning and CTA, respectively (FIGS. 2, 3). Moreover, PERK knockdown not only enhances memory but also results in improved CTA extinction, which indicates improved behavioral plasticity (FIG. 3). In addition, the enhanced memory resulted from improved learning, as retrieval was not affected (FIG. 4). It is noted that the improvement in these cognitive functions were observed in normal young animals having no cognitive deficiency as well as in normal aged animals showing signs of age-dependent cognitive dysfunction. Thus, there is no requirement for an a priori elevated level of PERK-activity or phosphorylated eIF2α in the IC and/or CA1 areas in an individual having normal cognitive function, e.g. as compared with the average PERK-activity or phosphorylated eIF2α level in these brain areas in a normal aged-matched population, for this individual to be responsive to treatment that lowers PERK activity. It is sufficient that the level of PERK or phosphorylated eIF2α in these brain areas in the individual having normal cognitive function who is treated with an agent that reduces PERK activity in the IC and/or CA1 areas is lower relative to the level in the same untreated individual.

Figure 8:
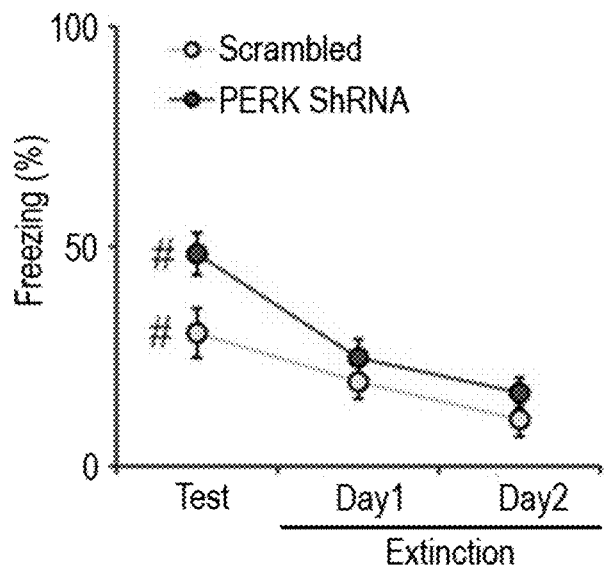
FIG. 8 shows that PERK shRNA reduces the total amount of PERK and p-eIF2 α levels in the CA1 region. (a) Cue extinction in PERK shRNA (ANOVA with repeated measures with a Greenhouse-Geisser correction, F (1.914, 19.14)=14.45, #p=0.0001) and scrambled (ANOVA with repeated measures, F (1.39, 13.902)=4.63, #p=0.039) AAV-injected animals. (b) Freezing during the trace interval after 48 hr (Independent-Sample T Test, t (20)=−2.69, *p=0.014), 72 hr (Independent-Sample T Test, t (22)=−0.512, p=0.147), and 96 hr (Independent-Sample T Test, t (22)=−1.146, p=0.736). Extinction for trace interval fear in PERK shRNA-treated animals (ANOVA with repeated measures with a Greenhouse-Geisser correction, F (1.83, 18.27)=5.34, #p=0.017) and scrambled controls (ANOVA with repeated measures with a Greenhouse-Geisser correction, F (1.5, 15.04)=4.49, #p=0.038). (c) Total PERK levels in the CA1 of PERK shRNA injected animals (Independent sample t-test, $t_{(14)}$=2.724, *p=0.016). (d) p-eIF2α levels in the CA1 following PERK knockdown (Independent sample t-test, $t_{(14)}$=2.28, *p=0.039) in the CA1 region. (e) Representative illustration of target area for PERK knockdown. (f) Structure of plasmid used to express either scrambled or PERK shRNA sequence.
Figure 8:
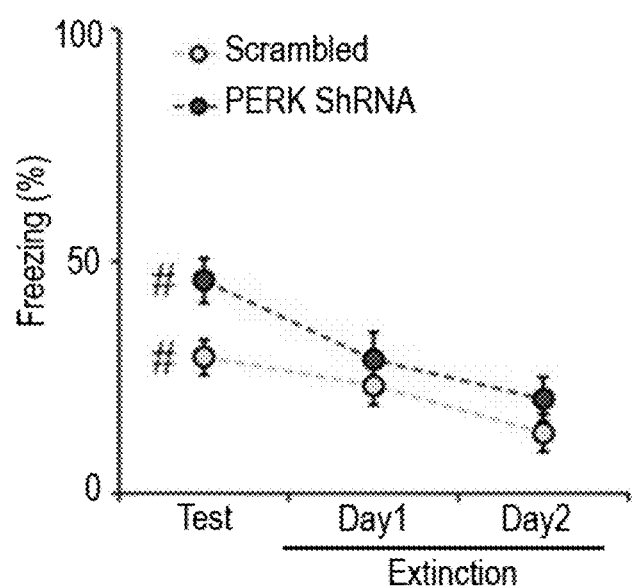
Figure 8:
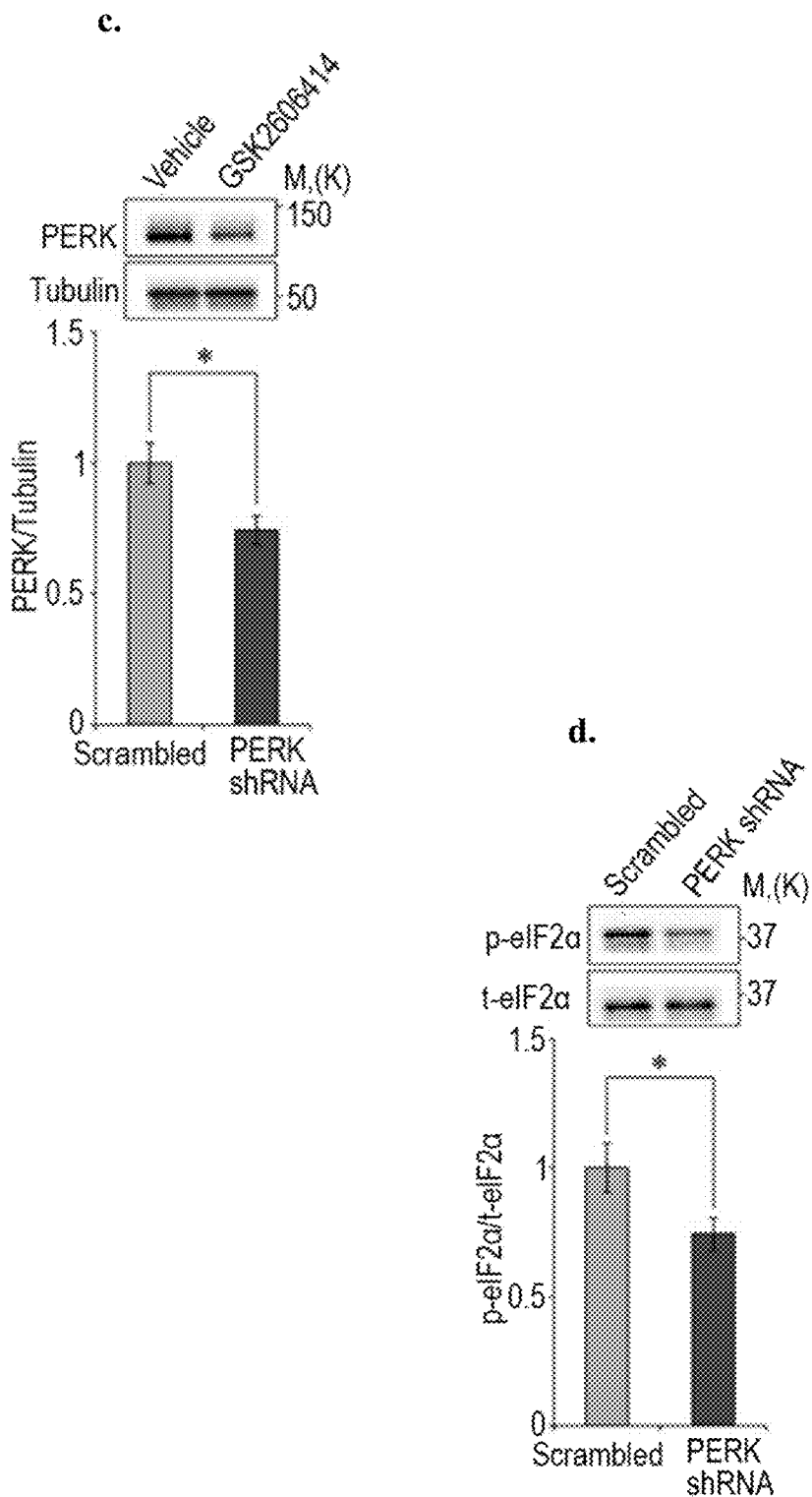
Figure 8:
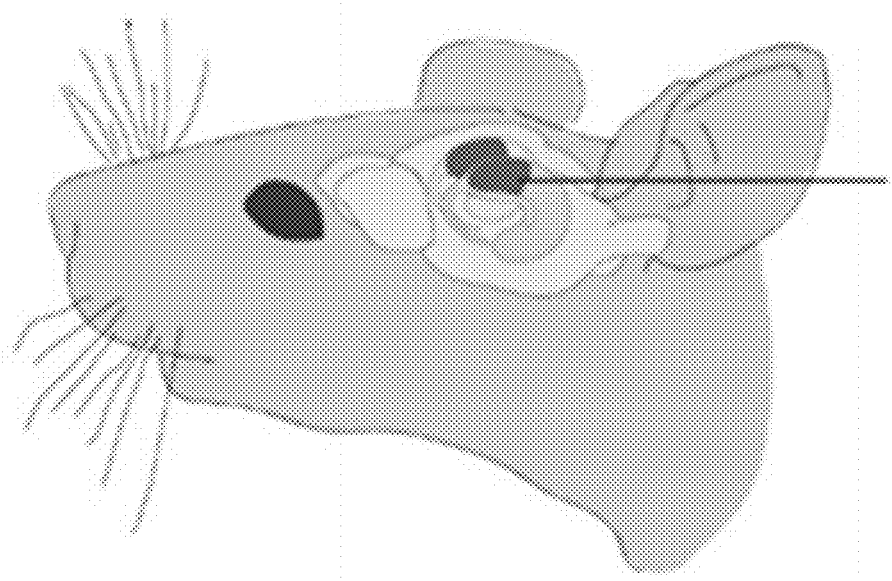
Figure 8:
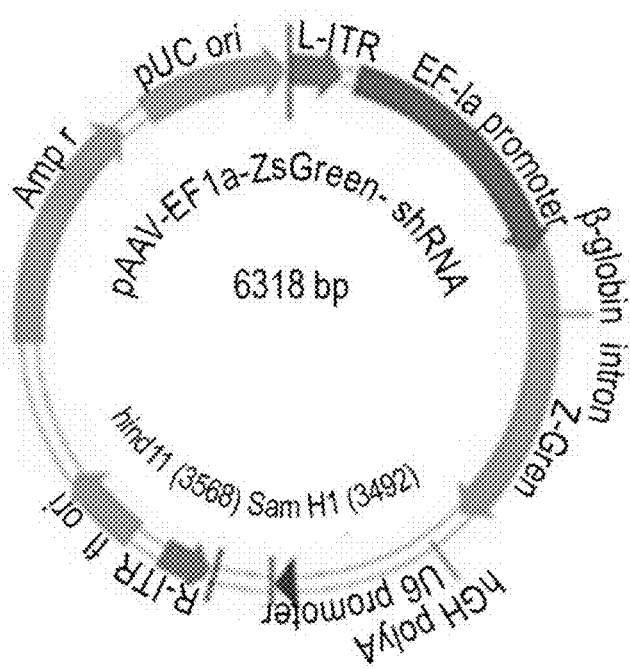
Figure 11:
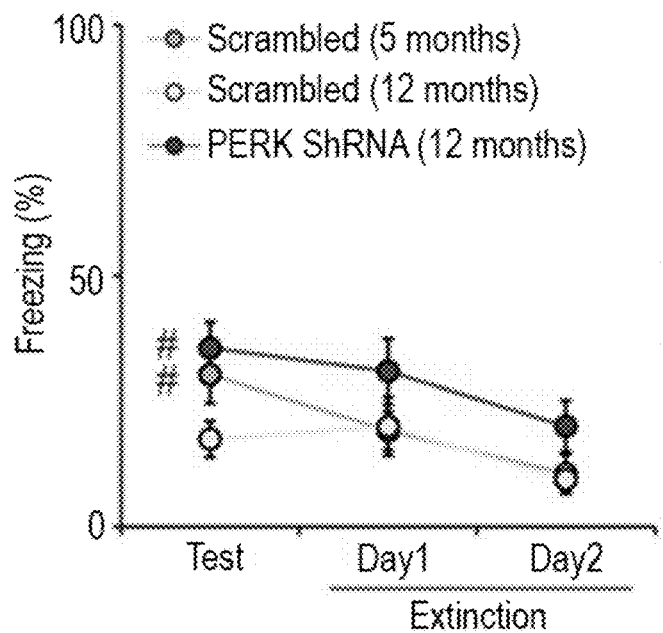
FIG. 11 shows that PERK knockdown in the aging brain changes AP characteristics. (a) Cue extinction in 5 month old scrambled control animals (ANOVA with repeated measures, F (1.39, 13.902)=4.63, #p=0.039), 12 month old PERK knockdown animals (#Friedman Test, $\chi^2$ (2)=7, p=0.030), and 12 month old scrambled control animals (ANOVA with repeated measures, F (1.179, 8.251)=3.962, p=0.077). (b) Trace extinction [#ANOVA with repeated measures (5 month scrambled, F (1.5, 15.04)=4.49, p=0.038), (12 month old PERK shRNA, F (1.69, 11.804)= 13.453, #p=0.001), (12 month old scrambled, F (1.40, 9.79)= 8.617, #p=0.011)]. (c) PERK mRNA relative quantity in 4 month old vs. 13 month old animals. (d) RMP in 12 month old scrambled and PERK shRNA AAV infected neurons (Tukey post-hoc test, *p=5.75×10$^{-7}$, *p=0.018 respectively). (e) Input resistance in scrambled and PERK shRNA groups in aging (Tukey post-hoc test, *p=0.011, *p=0.0073 respectively) vs. 5 month old scrambled control. (0 AP threshold in aged animals (Tukey post-hoc test, *p=0.0016, 12 month vs. 5 month old scrambled control animals), and following PERK knockdown (Tukey post-hoc test, *p=0.00012). (g) AP amplitude (Kruskal-Wallis H test, χ2 (2)=7.56, *p=0.023). Effect of age and PERK knockdown on AP amplitude (Kruskal-Wallis H test, p=0.02 and *p=0.017, respectively). (h) AP mid width (One-way ANOVA, $F_{(2,49)}$= 2.23, p=0.068).
Figure 11:
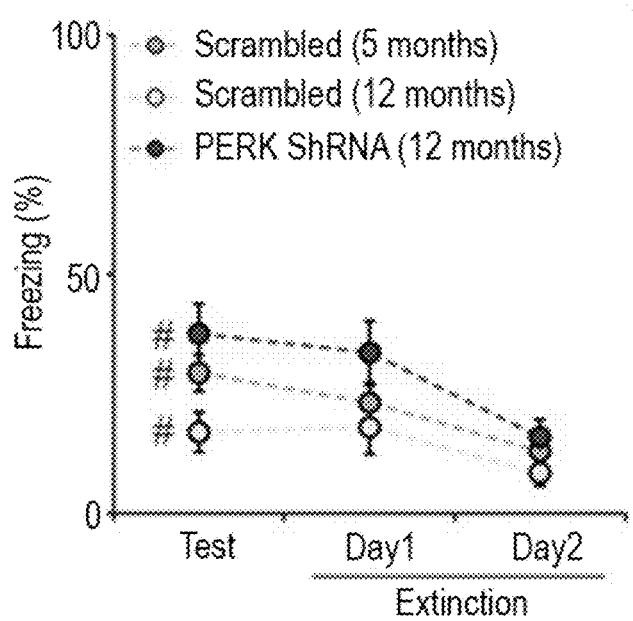
Figure 11:
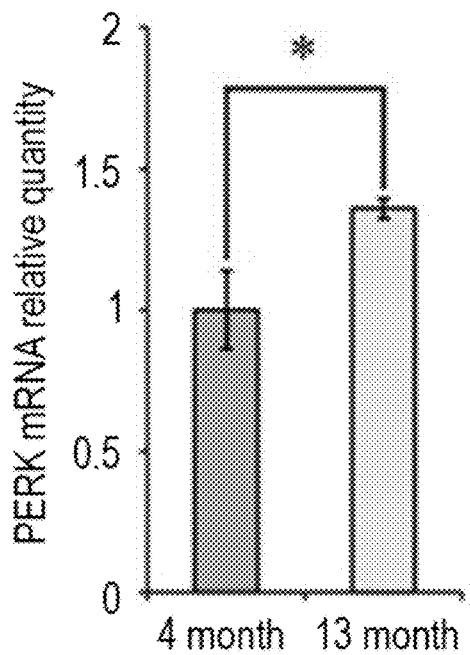
Figure 11:
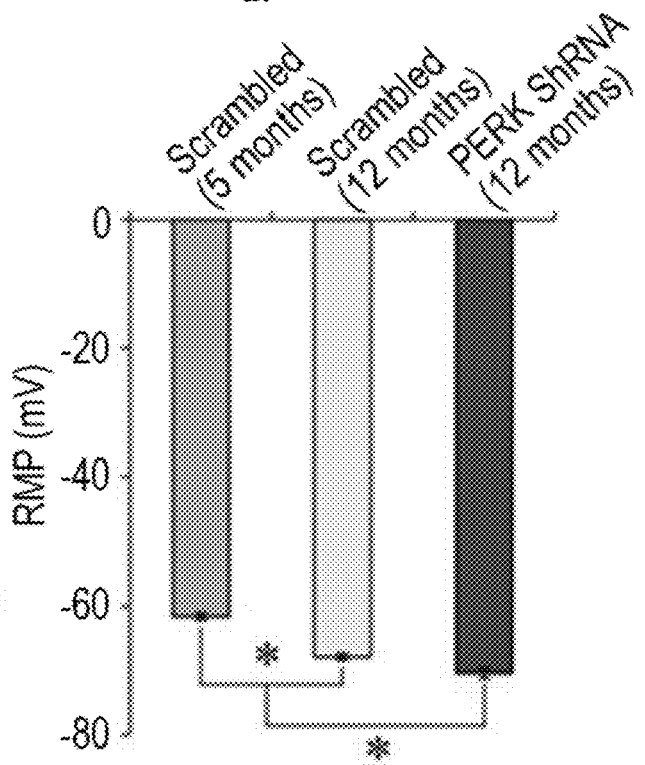
Figure 11:
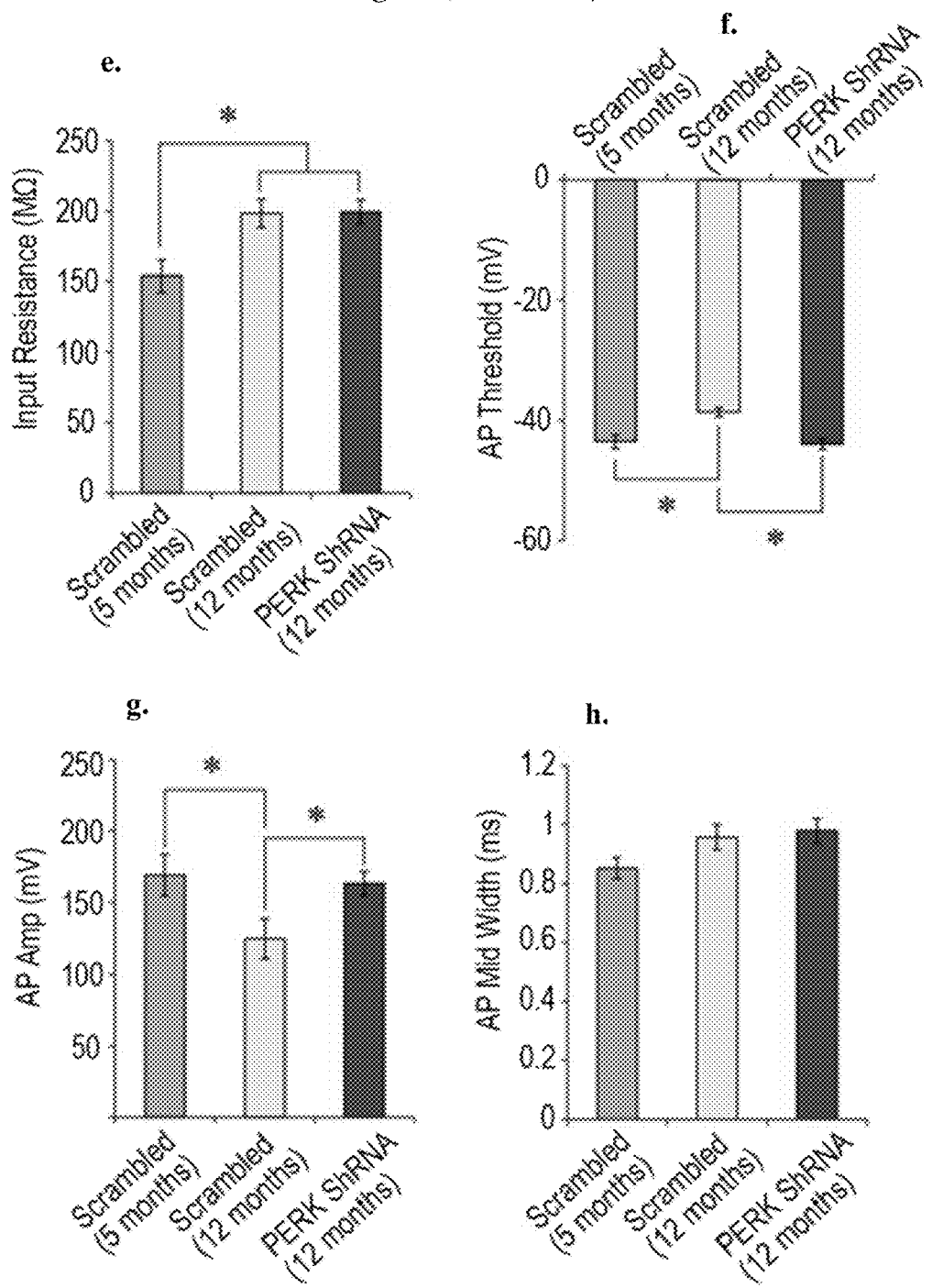
Figure 12:
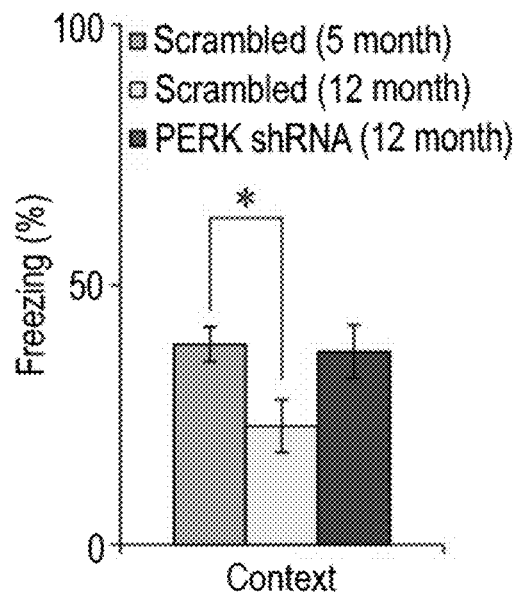
FIG. 12 shows that genetic reduction of PERK expression in the CA1 region alleviates memory deficits in aging animals and increases neuronal excitability of aged neurons beyond young neurons expressing scrambled controls. (a) Context memory is impaired in 12-month old animals injected with a scrambled lentivirus compared to 5-month old animals injected with the same vector. PERK knockdown in 12-month old animals restores context text memory, comparable to 5-month old injected with the scrambled vector (One-way ANOVA $F_{(2, 24)}$=3.728, *p=0.039, Tukey post-hoc test *p=0.043 scrambled (5 months); scrambled (12 months)). (b) Freezing during tone test is similar between the three groups. PERK knockdown increases trace freezing in 12 month old animals vs. 12 month old scrambled control, comparable with 5 month old animals treated with a scrambled vector (scrambled (5 months), One-way ANOVA, $F_{(2, 24)}$=4.24, *p=0.026, Tukey post-hoc test, *p=0.021). (c) Aging decreases AP frequency (12-month scrambled, n=18 vs. 5-month scrambled, n=13; Bonferroni post hoc, *p=0.04). PERK knockdown (n=21) reverses this reduction to levels comparable with 5-month old animals treated with a scrambled vector Bonferroni post hoc, *p=0.001; Two-way repeated measure ANOVA, $F_{(2,11)}$=26.526; *p=6.1× $10^{-5}$). (d) Aging increases mAHP (12-month scrambled, n=18 vs. 5-month scrambled, n=13 Tukey post hoc, *p=0.0048). PERK knockdown reduces mAHP in 12 month old animals (n=21) vs. 5 month and 12 month old scrambled controls (*Tukey post hoc, p=3.65×10'; * One-way ANOVA, $F_{(2,49)}$=66.59; p=1.06×$10^{-14}$).
Figure 12:
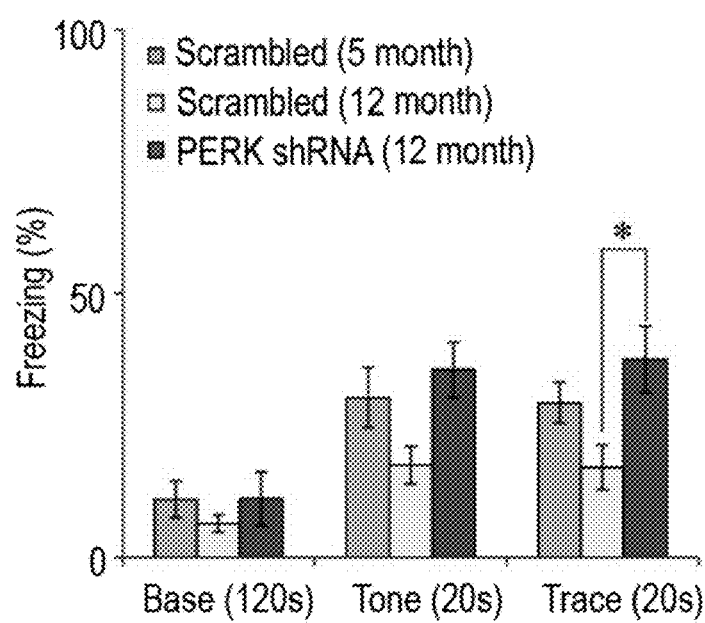
Figure 12:
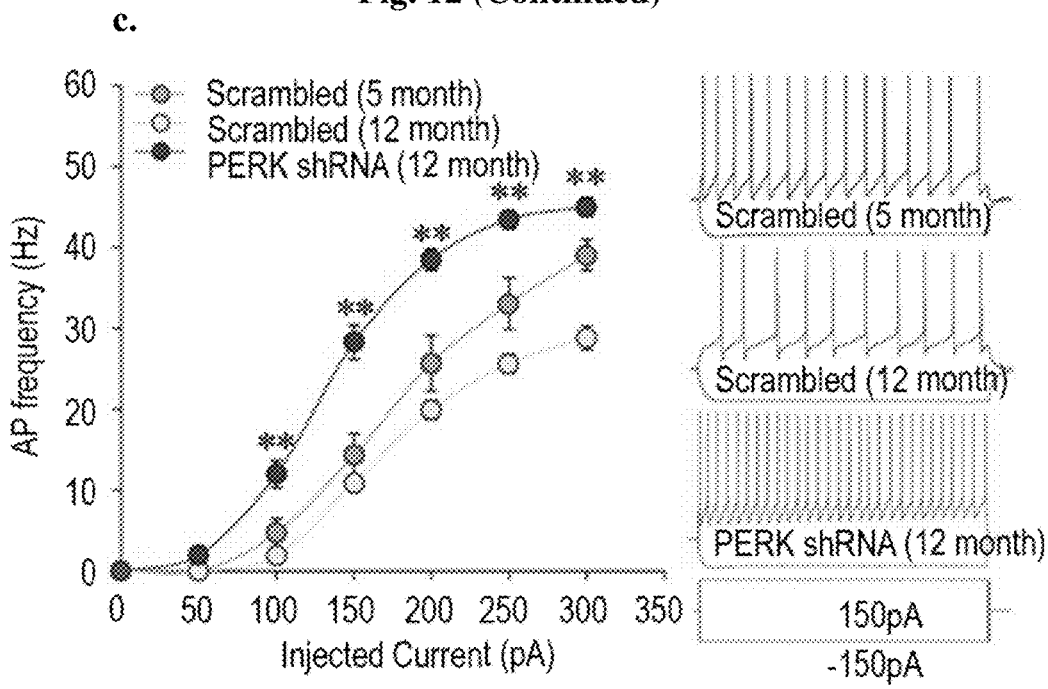
Figure 12:
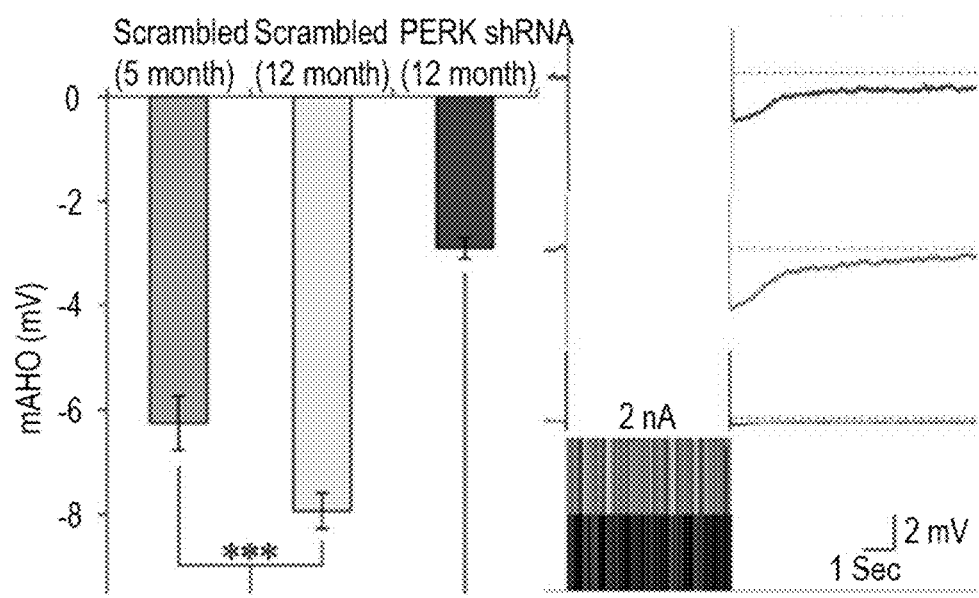

The phenotype achieved by genetically knocking down PERK in the CA1 region using PERK-specific shRNA was distinct from that of the PERK cKO mouse model under the CaMKII promoter, characterized by impaired hippocampal-dependent flexibility, but similar memory strength (Trinh et al., 2012; Trinh et al., 2014). The different phenotype observed in the present study suggests that the role of PERK in cognitive function depends on the brain area and cell type manipulated. In accordance with our hypothesis, the reduction in PERK activity or expression levels resulted in reduced p-eIF2α levels (FIG. 8). These results are in agreement with several reports by others and us, which link reduced p-eIF2α levels with enhanced memory (Costa-Mattioli, M. et al., 2007; Ounallah-Saad et al., 2014; Stern et al., 2013). Furthermore, we show here that PERK shRNA adeno-associated virus (AAV) rescues age-dependent deficits, as measured both on the behavioral level and on the physiological level (FIG. 12, FIG. 11), in line with the reported increase in hippocampal phosphorylation levels of eIF2α in aging in both rats and mice, observed at an earlier age in a model of AD (Segev et al., 2013).

Our data show that in young (5 month old) animals, pharmacological as well as genetic reduction of PERK activity or levels resulted in significantly reduced modulation in afterhyperpolarization (AHP), increased excitability, and improved cognitive performance. Moreover, genetic reduction of PERK expression in the CA1 region of the hippocampus in aging (12-month-old) mice rescued memory deterioration, reduced the mAHP, and increased action potential frequency. Thus, it has been found in accordance with the present invention that reducing PERK levels affect neuronal intrinsic excitability properties, and rescue cognitive deficits related to normal aging.

It is important to keep in mind that different parts of the human brain are responsible for different functions and different types of information. The taste memory is within the insular cortex whereas the spatial memory is within the hippocampus. Cognitive deterioration can occur at various levels of function, and it is therefore an important finding of the present invention that each type of function can be enhanced independently, i.e. cortex-dependent and hippocampus-dependent cognitive functions may both be improved by the methods of the present invention together or each one independently.

The findings disclosed herein can be extended to neurodegenerative diseases because the method of the present invention is not aimed at modifying specific disease mechanism, but acts upon the fundamental level of PERK and protein translation. A decrease in PERK activity leads to increased protein translation that in turn leads to improved cognitive function. Thus, even if a neurodegenerative disease has decimated many functioning neurons in a diseased brain, the remaining neurons in the IC and CA1 areas are amenable to reduction of their PERK activity and therefore can contribute to improvement in cognitive function.

In view of the above, in one aspect, the present invention provides a method for improving a cognitive function in a subject comprising administering to said subject an active agent reducing PKR-like endoplasmic reticulum kinase (PERK) activity. In certain embodiments the subject has age-related cognitive dysfunction or the subject has a disease, disorder, condition or injury characterized by cognitive impairment.

In certain embodiments, the subject is not an immune-deficient subject, i.e. a subject having a compromised immune system, for example a subject having an immune system characterized by a reduced level of functional T cells and B cells, lymphopenia, hypogammaglobulinemia, and a normal hematopoietic microenvironment.

In certain embodiments, the subject is not afflicted with priori disease.

In certain embodiments, the active agent is administered locally to the cerebral cortex or hippocampus of said subject or alternatively it may be administered systemically to said subject.

Local administration of the active agent may for example be facilitated by formulating it in the form of nanoparticles or by delivering it directly into the brain by intranasal administration, while systemic administration may be facilitated by formulating it for example as capsules having an outer layer comprising a brain-specific targeting moiety.

In certain embodiments, the active agent is a small molecule inhibitor of the formula (I):

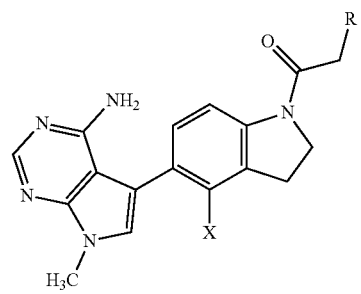

wherein

X is H or F; and

R is selected from 3-trifluoromethylphenyl, 2-pyridinyl, 3-pyridinyl, 4-pyridynyl, 2-methylpyridin-6-yl, 2-trifluoromethylpyridin-6-yl, 3-methylpyrazol-1-yl, 5-methylpyrazol-1-yl, or 3,5-dimethylpyrazol-1yl.

In certain embodiments X is H and R is 3-trifluoromethylphenyl (compound 1) or X is F and R is 2-methylpyridin-6-yl (compound 6), 2-trifluoromethylpyridin-6-yl (compound 8), or 3,5-dimethylpyrazol-1yl (compound 12), in particular compound 1 or 6.

Alternatively, the active agent is an isolated nucleic acid molecule that reduces the gene expression level of PERK, for example an shRNA or artificial siRNA molecule comprising a nucleic acid sequence being complementary to a sequence within a nucleic acid sequence encoding PERK, or a nucleic acid molecule encoding the shRNA or artificial siRNA molecule.

In certain embodiments, PERK is a human PERK, in particular a human PERK having an amino acid sequence as set forth in SEQ ID NO: 1.

The present invention further relates to an isolated nucleic acid molecule comprising a polynucleotide sequence being complementary to a sequence within a sequence encoding PERK that has an amino acid sequence that is at least 80%, at least 85%, at least 90%, or at least 95, 96, 97, 98, or 99% identical to the amino acid sequence of SEQ ID NO: 1.

In certain embodiments, the human PERK is encoded by a nucleic acid sequence herein identified as SEQ ID NO: 2.

In certain embodiments, the siRNA or shRNA molecule comprises a nucleic acid sequence being perfectly complementary to a sequence within the nucleic acid sequence encoding said PERK; for example it is being perfectly complementary to a sequence within SEQ ID NO: 2.

In order to enable therapeutic use of the nucleic acid molecule described herein above, it may be comprised within a vector, such as, but not limited to, a modified virus derived from a virus selected from the group consisting of a retrovirus, adenovirus, adeno-associated virus, pox virus, alphavirus, herpes virus and lentivirus. In particular, the vector is a modified lentivirus.

In some embodiments, the improvement of cognition obtained with the methods of the present invention comprises improvement of a cognitive function selected from learning, behavioral plasticity and/or long term memory. The cognition may be cortical or hippocampus dependent cognition.

The terms "cognition", "cognitive function" and "cognitive performance" are used herein interchangeably and are related to any mental process or state that involves but is not limited to learning, memory, creation of imagery, thinking, awareness, reasoning, spatial ability, speech and language skills, language acquisition and capacity for judgment attention. Cognition is formed in multiple areas of the brain such as hippocampus, cortex and other brain structures. However, it is assumed that long term memories are stored at least in part in the cortex and it is known that sensory information is acquired, consolidated and retrieved by a specific cortical structure, the gustatory cortex, which resides within the insular cortex.

In humans, cognitive function may be measured by any know method, for example and without limitation, by the clinical global impression of change scale (CIBIC-plus scale); the Mini Mental State Exam (MMSE); the Neuropsychiatric Inventory (NPI); the Clinical Dementia Rating Scale (CDR); the Cambridge Neuropsychological Test Automated Battery (CANTAB) or the Sandoz Clinical Assessment-Geriatric (SCAG). Cognitive function may also be measured indirectly using imaging techniques such as Positron Emission Tomography (PET), functional magnetic resonance imaging (fMRI), Single Photon Emission Computed Tomography (SPECT), or any other imaging technique that allows one to measure brain function.

An improvement of one or more of the processes affecting the cognition in a patient will signify an improvement of the cognitive function in said patient, thus in certain embodiments improving cognition comprises improving learning, plasticity, and/or long term memory. The terms "improving" and "enhancing" may be used interchangeably.

The term "learning" relates to acquiring or gaining new, or modifying and reinforcing, existing knowledge, behaviors, skills, values, or preferences.

The term "plasticity" relates to synaptic plasticity, brain plasticity or neuroplasticity associated with the ability of the brain to change with learning, and to change the already acquired memory. One measurable parameter reflecting plasticity is memory extinction.

The term "memory" relates to the process in which information is encoded, stored, and retrieved. Memory has three distinguishable categories: sensory memory, short-term memory, and long-term memory.

The term "long term memory" is the ability to keep information for a long or unlimited period of time. Long term memory comprises two major divisions: explicit memory (declarative memory) and implicit memory (non-declarative memory). Long term memory is achieved by memory consolidation which is a category of processes that stabilize a memory trace after its initial acquisition. Consolidation is distinguished into two specific processes, synaptic consolidation, which occurs within the first few hours after learning, and system consolidation, where hippocampus-dependent memories become independent of the hippocampus over a period of weeks to years.

In some embodiments, the subject has normal cognitive function. Alternatively, the subject has age-related cognitive dysfunction, e.g. mild cognitive impairment (MCI), or suffers from a disease, disorder, condition or injury characterized by cognitive impairment, such as a disease, disorder, condition or injury selected from mild cognitive impairment, Alzheimer's disease; Parkinson's disease; amnesia such as electric shock induced amnesia; dementia such as multi-infarct dementia or senile dementia; amyotrophic lateral sclerosis; a brain injury; cerebral senility; chronic peripheral neuropathy; a cognitive disability; a degenerative disorder associated with a learning and memory deficit; defective synaptic transmission; Down's Syndrome; dyslexia; Guillain-Barre syndrome; head trauma; stroke; cerebral ischemia; Huntington's disease; a learning disability; a memory deficiency; memory loss; a mental illness; mental retardation; memory or cognitive dysfunction; myasthenia gravis; a neuromuscular disorder; Pick's disease; a reduction in spatial memory retention; senility; Tourrett's syndrome; cardiac arrest; open heart surgery; chronic fatigue syndrome; autism; epileptic seizures; major depression or electroconvulsive therapy.

In certain embodiments, the method of the present invention comprises administering to the subject a modified lentivirus vector comprising a nucleic acid molecule encoding an shRNA molecule comprising a nucleic acid sequence being perfectly complementary to a sequence within SEQ ID NO: 2, wherein said subject has normal cognitive function or age-related cognitive dysfunction.

In another aspect, the present invention is directed to a vector comprising an active agent comprising a nucleic acid molecule that reduces the gene expression level of PERK as defined herein operably linked to a control element, such as a promoter and/or terminator. For example, the vector may be a modified virus derived from a virus selected from retrovirus, adenovirus, adeno-associated virus, pox virus, alphavirus, herpes virus, or lentivirus. In particular, the modified virus is a modified lentivirus.

In a further aspect, the present invention provides a pharmaceutical composition comprising an active agent or a vector as defined herein, and a pharmaceutically acceptable carrier.

In certain embodiments, the pharmaceutical composition comprises a vector comprising a nucleic acid molecule encoding an shRNA molecule as defined above comprising a sequence being complementary to a sequence within a nucleic acid sequence encoding said PERK.

In certain embodiments, the PERK is a human PERK, in particular a human PERK having an amino acid sequence as set forth in SEQ ID NO: 1.

In certain embodiments, the human PERK is encoded by a nucleic acid sequence herein identified as SEQ ID NO: 2.

In particular, the pharmaceutical composition of the present invention comprises a vector comprising a nucleic acid molecule encoding an shRNA molecule being perfectly complementary to a sequence within SEQ ID NO: 2.

The pharmaceutical composition may be formulated for intravenous, intra-brain (intracerebral), oral, intradermal, intramuscular, subcutaneous, transdermal, transmucosal, intranasal or intraocular administration, as well as for intraperitoneal, intrathecal and topical routes. Administration can be systemic or local. In certain embodiments, the pharmaceutical composition is formulated for intravenous, intra-brain (intracerebral) or nasal administration.

Pharmaceutical compositions for use in accordance with the present invention may be formulated in conventional manner using one or more physiologically acceptable carriers or excipients. The carrier(s) must be "acceptable" in the sense of being compatible with the other ingredients of the composition and not deleterious to the recipient thereof.

The following exemplification of carriers, modes of administration, dosage forms, etc., are listed as known possibilities from which the carriers, modes of administration, dosage forms, etc., may be selected for use with the present invention. Those of ordinary skill in the art will understand, however, that any given formulation and mode of administration selected should first be tested to determine that it achieves the desired results.

The term "carrier" refers to a diluent, adjuvant, excipient, or vehicle with which the active agent is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; and a glidant, such as colloidal silicon dioxide.

According to the present invention, any pharmaceutically acceptable salt of the active agent can be used. Examples of pharmaceutically acceptable salts include, without being limited to, the mesylate salt, the esylate salt, the tosylate salt, the sulfate salt, the sulfonate salt, the phosphate salt, the carboxylate salt, the maleate salt, the fumarate salt, the tartrate salt, the benzoate salt, the acetate salt, the hydrochloride salt, and the hydrobromide salt.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Preparations for oral administration may be suitably formulated to give controlled release of the active compound.

For buccal administration, the compositions may take the form of tablets or lozenges formulated in conventional manner.

The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

In an additional aspect, the present invention provides a method for improving cognition in a subject comprising administering compound 1 or compound 6 to the subject, in particular compound 6.

In yet another aspect, the present invention is directed to a method for improving cognition in a subject comprising administering to the subject a modified lentivirus vector comprising any one of the nucleic acid molecules described above encoding an shRNA molecule comprising a sequence being complementary to a sequence within a nucleic acid sequence encoding the PERK. In particular, the modified lentivirus vector used in the method of the present invention comprises a nucleic acid molecule encoding an shRNA molecule being perfectly complementary to a sequence within SEQ ID NO: 2. For example, the vector used in the method of the present invention has the nucleic acid sequence herein identified as SEQ ID NO: 3.

The term "treating" as used herein refers to means of obtaining a desired physiological effect. The effect may be therapeutic in terms of partially or completely curing a disease and/or symptoms attributed to the disease. The term refers to inhibiting the disease, i.e. arresting its development; or ameliorating the disease, i.e. causing regression of the disease.

As used herein, the terms "subject" or "individual" or "animal" or "patient" or "mammal," refers to any subject, particularly a mammalian subject, for whom diagnosis, prognosis, or therapy is desired, for example, a human.

For purposes of clarity, and in no way limiting the scope of the teachings, unless otherwise indicated, all numbers expressing quantities, percentages or proportions, and other numerical values recited herein, should be interpreted as being preceded in all instances by the term "about." Accordingly, the numerical parameters recited in the present specification are approximations that may vary depending on the desired outcome. For example, each numerical parameter may be construed in light of the number of reported significant digits and by applying ordinary rounding techniques.

The term "about" as used herein means that values of 10% or less above or below the indicated values are also included.

The invention will now be illustrated by the following non-limiting examples.

EXAMPLES

Material and Methods
Tissue Culture

NIH3T3 mouse fibroblasts were propagated in DMEM, adjusted to contain 1.5 g/l sodium bicarbonate, 0.1 mM non-essential amino acids, and 1 mM sodium pyruvate. All media were supplemented with 10% Fetal Bovine Serum (FBS), 2 mM L-glutamine, 10 units penicillin, 10 µg streptomycin/ml, and 30 µg/ml cefuroxime antibiotics. Cell lines were maintained at 37° C. with 5% $CO_2$ and subcultured twice weekly. Primary cultures of cortical neurons were prepared from the cortex of 1 day old neonatal mice or rats. Briefly, the dissected tissue was digested using trypsin and DNase in digestion solution (137 mM NaCl, 5 mM KCl, 7 mM $Na_2HPO_4$, 25 mM HEPES, pH 7.2), and was further mechanically dissociated using a silicon-coated Pasteur pipette with DNAse supplemented dissociation solution (12 mM $MgSO_4*7H_2O$ in HBSS). HBSS+FBS 20% were added to the supernatant, and centrifuged for 10 min at 1500×g, 4° C. The supernatant was aspirated and the pellet was resuspended in HBSS, this step was repeated twice, and the final pellet was resuspended in MEM-10% and cells were seeded on polyethyleneimine (PEI) coated plates. The cells were grown in MEM 10% for 1 week, and were later kept for 3 days in MEM-10% ARA-C (3 µM) to halt glial growth, and were then maintained for another in MEM-10% B27 (Gibco, according to manufacturer's instructions) medium to support neuronal growth, before viral infection.

Animals

Adult, male Wistar Hola rats, aged about 60 d, weighing 200-250 g (Harlan, Jerusalem) were used in all experiments in Examples 1 to 4. C57BL/6 mice (Harlan, Jerusalem) about 12-week-old, weighing 20-25 g were used in Examples 5 to 7, unless otherwise indicated. They were housed individually, on a 12/12-h light/dark cycle, and provided with water and standard rodent chow ad libitum.

Animals were handled according to approved protocols and animal welfare regulations of the University of Haifa Institutional Ethics Committee.

For the aging experiment, 8 month old mice were purchased from Harlan, and kept under the same conditions until the time of the experiment.

Infusion of Recombinant Lentivirus Harboring PERK shRNA to Adult Rat Insular Cortex For virus infusions, rats were first anesthetized with Ketamine (120 mg/kg) and Xylazine (6 mg/kg) and placed into a stereotactic frame (Steolting Europe, Dublin—Ireland) (Using a 32-gauge stainless steel injector attached to a stereotactic infusion pump, rats received 1 µl of lentivirus encoding PERK shRNA or lentivirus harboring a scrambled sequence over 10 min into the insular cortex (anteroposterior, +1.2 mm relative to bregma; lateral, ±5.5 mm; ventral, −6.0 mm) according to the atlas of Paxinos, G. & Watson, C. (2006). The injector was lets in place for 5 min before and after infusion to minimize fluid retraction. The rats were allowed at least 7 days to recover from the surgery before any behavior experiments were conducted.

Cannula Implantation in Rats and Microinfusion of PERK Inhibitor GSK2606414 (Compound 6)

The rats were cannulated as described in Barki-Harrington et al. (2009). Briefly, the rats were anesthetized by administration of equithesin (0.3 ml/100 g), comprising 2.12% (w/v) MgSO$_4$, 10% (v/v) ethanol, 39.1% (v/v) propyleneglycol, 0.98% (w/v) sodium pentobarbital, and 4.2% (w/v) chloral hydrate. They were restrained in a stereotactic frame (Steolting Europe, Dublin-Ireland) and stainless steel guide cannulae (23-gauge) were bilaterally implanted into the insular cortex, angled at (with reference to bregma), anteroposterior=+1.2 mm, lateral±5.5 mm, and ventral 5.0 mm (1 mm ahead of injecting cannula). Two skull screws were inserted into the skull, and acrylic dental cement was applied to secure the cannulae in position. A 28 gauge stylus was inserted into each guide cannula to prevent clogging. The rats were allowed a week in individual cages to recover from the surgery, before the experimental manipulation. PERK inhibitor GSK2606414 (Axten et al., 2012) was dissolved in DMSO and further diluted in saline to a final DMSO concentration of 0.5%. A total of 1 µl of 100 nM GSK2606414 or vehicle was infused bilaterally. For microinfusion, the stylus was removed from the guide cannula and a 28 gauge injection cannula was carefully inserted, to extend 1.0 mm beyond the tip of the guide cannula. The injection cannula was connected via PE20 tubing to a Hamilton syringe (Hamilton) driven by a CMA/100 microinjection pump (Carnegie Medicine), to provide an injection rate of 1 µl/min. After 1 min of infusion, the injection cannula was kept in the guide cannula for an additional minute to minimize dragging of infused solutes along the injection tract. Locations of cannula were verified in 30 µm coronal sections.

Stereotaxic Administration of PERK shRNA AAV

To perform stereotaxic viral injections into the brain, mice were anesthetized under 2% isoflurane using an anesthesia system (HME109, Highland Medical Equipment). The mice were then placed in a rodent stereotaxic apparatus (Kopf Stereotaxic Alignment System Model 1900) with continuous 1% isoflurane. A small incision was made in the head, the skin reflected, and the skull exposed to show the bregma and lambda, and desired injection sites. The following injection coordinates targeting dorsal hippocampal CA1 were used: −1.46 mm anteroposterior (AP), ±1 mm mediolateral (ML), −1.4 mm dorsoventral (DV) (all values given relative to bregma). A small drill hole was made in the skull over the injection site. A 50 µl Hamilton syringe with 32-gauge stainless steel needle, connected to a stereotacxic infusion pump was used to inject virus into the brain. A total of 1 µl of PERK shRNA AAV (pAAV-EF1a-ZsGreen-shRNA, $1 \times 10^{12}$ vg per ml, serotype 5) or scrambled sequence AAV was bilaterally injected into the brain at a rate of 50 nl/min. The injector was left in place for 5 min before and after infusion to minimize fluid retraction. Once the injection pipette was withdrawn, the mouse was removed from the stereotaxic apparatus, and the incision was closed with tissue adhesive (3M Vetbond, St. Paul, Minn.). The mice were allowed at least 4 weeks to recuperate and allow infected neurons to express high contents of AAV before any behavior experiments were conducted.

Cannula Implantation in Mice and Microinjection of PERK Inhibitor GSK2606414

Animals were anesthetized under 2% isoflurane using an isoflurane table top unit (HME109, Highland Medical Equipment). Under aseptic conditions, a rodent stereotaxic apparatus (Kopf Stereotaxic Alignment System Model 1900) with continuous 1% isoflurane anesthesia was used. For CA1 infusion cannula was implanted bilaterally into the CA1 region (from the bregma: −1.94 mm AP, ±1.0 mm ML, −1.0 mm DV). The implanted cannula was cemented on the skull. Each cannula was fitted with a 28 gauge dummy cannula that extended 0.1 mm beyond the tip of the guide cannula to prevent blockage of the guide cannula. After cannulation, mice were allowed to recover for 7 days before infusion of PERK inhibitor or vehicle and behavior. On conditioning day, randomly assigned mice were infused with 100 nM PERK inhibitor GSK2606414 (Axten et al., 2012) dissolved in dimethyl sulfoxide (DMSO) and further diluted in saline to a final DMSO concentration of 0.5%, via a 28-gauge infusion cannula connected by polyethylene (PE 20) tubing to a 10 µL Hamilton microsyringe (Hamilton Company). The infusion cannula protruded 0.25 mm beyond the guide cannula. For CA1 administration, infusion volume of 1 µl of 100 nM GSK2606414 or vehicle was delivered using a Harvard PHD2000 syringe pump (Harvard Apparatus) over the course of 1 min (at a rate of 1 µL/min). After infusion, the injection cannula was kept in the guide cannula for an additional minute to minimize dragging of infused solutes along the injection tract. Locations of cannula were verified in 30 µm coronal sections.

Lentivirus Production, Infection, and Expression.

Short hairpin RNA constructs directed against PERK/PKR/GCN2 were purchased from Sigma/OriGene (for PERK and PKR shutdown we used Sigma clones no.TRCN28772, TRCN 26988, respectively in pLKO.1-puro-CMVTurboGFP plasmids (SEQ ID NO: 3; the shRNA sequence complementary to a sequence of the PERK gene is highlighted), for GCN2 we used OriGene clone no.GI572502). The scrambled and GCN2 shRNA sequences were subcloned into the lentiviral plasmid pFUGW6 for coexpression of shRNA driven by U6 promoter, and EGFP driven by Ubiquitin promoter. Using Blast2Sequences, PERK mouse sequence was found to be highly homologous to PERK rat sequence, and the efficacy of PERK shRNA (clone TRCN28772) to shutdown PERK expression was the same in both mouse and rat primary cultures. Lentiviral particles were produced according to Lois et al. 2002. Briefly, lentiviral expression, packaging, and envelope plasmid vectors were cotransfected into the 293FT cell line (Invitrogen, Carlsbad, Calif., USA), and allowed to express and form viral particles for 48 h. The medium was collected and the viral particles were purified and concentrated by multiple centrifugation steps, dissolved in sterile PBS, aliquoted, and stored at −80° C. until further use. To confirm that shRNA expression attenuates kinase specific levels, we infected 3T3 cells and primary cultures by adding 5 MOI of the virus (stock titer was 10^9/ml transducing units (tu) into the culture medium over night. The medium was replaced the day after infection, and cells were allowed 1 week to achieve stable expression levels. The cells were harvested in sample buffer X2 (10% Glycerol, 2% SDS, 0.5M Tris-HCl), and immunoblot analysis was performed as described below. In vivo, lentivirus was injected into the insular cortex as described above, and allowed to express for 7 days. To test the effect on learning, we injected shRNA-expressing or control viruses harboring a scrambled sequence 7 days before CTA was performed. To test the effect on retrieval, CTA was performed first, and after 7 days the shRNA-expressing or control virus was injected. Aversion to the novel taste, 0.3% NaCl was measured as described below.

Preparation of Total Samples for Biochemical Analysis

At the end of the behavioral procedure, the brains were removed, and snap-frozen in liquid nitrogen. Gustatory cortex punches were made using a cryostat (Leica, Germany) according to injection coordinates and were homogenized by 30 strokes in a glass-Teflon homogenizer in a lysis buffer containing 10 mM HEPES, pH 7.4, 2 mM EDTA, 2 mM EGTA, 0.5 mM DTT, 1% phosphatase inhibitor cocktail (3-P0044, Sigma), and 1% protease inhibitor cocktail (p2714, Sigma). Protein content was determined with the BCA Protein Assay Kit (GE Healthcare). Appropriate volumes of 2×SDS sample buffer (10% glycerol, 5% β-mercaptoethanol, 4% SDS, 120 mM Tris-HCl, pH 6.8) were added to the homogenates, and samples were boiled for 5 min and stored at −80° C. till further analysis.

Western Blotting

Samples were prepared in SDS sample buffer, subjected to 7.5-10% SDS-PAGE and Western blot analysis. Each lane was loaded with equal amounts of protein (10 µg). After transfer to a nitrocellulose membrane, the blots were blocked for 1 h with 4% BSA in Tris-buffered saline plus 0.5% Tween 20 (TBST) at room temperature. They were then incubated overnight with the primary antibodies PKR (1:1000; Santa Cruz), eIF2α (1:1000; Cell Signaling Technology), p-(Ser51) eIF2α (1:1000; Invitrogen), GCN2, PERK, (both 1:1000; Cell Signaling Technology), β-actin (1:3000; Santa Cruz Biotechnology), and β-tubulin (1:30,000; Sigma). The blots were then subjected to three 5 min washing steps in TBST, after which they were incubated with the corresponding HRP-conjugated secondary antibodies: goat anti-rabbit (IgG), goat anti-mouse (IgG), or rabbit anti-goat (IgG) (1:10,000; Millipore Bioscience Research Reagents), for 1 h at room temperature followed by three 10 min washes with TBST. Immunodetection was performed with the enhanced chemiluminescence EZ-ECL Kit (Biological Industries). The immunoblots were quantified with a CCD camera and Quantity One software (Bio-Rad, USA). Each sample was measured relative to the background. Phosphorylation levels were calculated as the ratio between chemiluminescence values of the antibody directed against the phosphoproteins and those of the antibody directed against the phosphorylation state independent forms of the proteins.

RNA Extraction and Quantitative Real Time PCR.

RNA was extracted, from mouse hippocampus using TRI Reagent (Molecular Research Center INC), according to the manufacturers protocol. RNA concentration and purity were evaluated using Nanodrop (ThermoScientific, Nanodrop2000). High Capacity Reverse Transcription Kit (ABI, USA) was used according to the manufacturer's instructions for cDNA synthesis, in a total volume of 20 µl using 1 µg of RNA as template. The qRT-PCR reaction was performed in a total volume of 10 µl using the following TaqMan assays (Applied Biosystems, USA): PERK (Mm00438700_m1), HPRT (Mm00446968_m1). Reactions were carried out in accordance with the manufacturer's instructions. Real Time-PCR analysis was performed using the PCR System STEP-ONE plus (Applied Biosystems). Relative mRNA levels were calculated using the $\Delta\Delta C_t$ method, and the $2^{-\Delta\Delta Ct}$ formula. Statistical analysis were performed on dct values.

Electrophysiology

Tissue Preparation

Mice were sacrificed by cervical dislocation and three hundred micrometer coronal brain slices were cut with a Campden-1000 Vibrotome. Slices were cut in ice-cold cutting solution containing (in mM) 110 sucrose, 60 NaCl, 3 KCl, 1.25 $NaH_2PO_4$, 28 $NaHCO_3$, 0.5 $CaCl_2$, 7 $MgCl_2$, 5 glucose, and 0.6 ascorbate and recovered for 30 min at 37° C. in artificial cerebrospinal fluid (ACSF) containing (in mM) 125 NaCl, 2.5 KCl, 1.25 $NaH_2PO_4$, 25 $NaHCO_3$, 25 D-glucose, 2 $CaCl_2$, and 1 $MgCl_2$, followed by additional recovery for 30 min in room-temperature ACSF. After initial recovery, slices were placed in a submerged chamber and maintained at 34° C. in ACSF (2 ml/min). All solutions were constantly carboxygenated with 95% $O_2$+5% $CO_2$.

Intracellular Recording

Pyramidal cells were illuminated and visualized under infrared differential interference contrast microscope with a ×60 water-immersion objective mounted on a fixed-stage microscope (BX51-WI; Olympus), and the image was displayed on a video monitor using a charge-coupled device camera (Hamamatsu). Cells infected with PERK-shRNA- or scrambled sequence PERK shRNA (PERK-Scr)-containing AAV were identified by green fluorescence. Recordings were amplified by multiclamp 700B and digitized by Digidata 1440 (Molecular Devices). The recording electrode was pulled from a borosilicate glass pipette (3-5 MΩ) using an electrode puller (P-1000; Sutter Instruments) and filled with a K-gluconate-based internal solution containing (in mM) 120 K-gluconate, 20 KCl, 10 HEPES, 2 $MgCl_2$, 4 $Na_2ATP$, 0.5 TrisGTP, 14 phosphocreatine, osmolarity 290 mOsm, and pH 7.3. The recording glass pipettes were patched onto the soma region of pyramidal cells. Voltages for liquid junction potential (+10 mV) were not corrected online. All current-clamp recordings were low-pass filtered at 10 kHz and sampled at 50 kHz. Series resistance was compensated and only series resistance <20 MΩ was included in the data set. Pipette capacitance was ~99% compensated. The method for measuring active intrinsic properties was based on a modified version of Kaphzan H et al., 2013. For recordings with GSK2606414, 100 nM inhibitor was applied in the pipette solution, and recordings were performed as described above.

Recording Parameters

Resting membrane potential (RMP) was measured 5 min after the seal was ruptured. The I-V (current-voltage) relationship used to calculate number of action potentials obtained by injection of 1 s pulses (−150 to +300 pA in 50 pA increments).

Input resistance (Rin) was calculated from the voltage response to a hyperpolarizing current pulse (−150 pA). For measurements of a single AP, after initial assessment of the current, which was required to induce an action potential at 15 ms from the start of the current injection with large steps (50 pA), we injected a series of brief depolarizing currents for 10 ms in steps of 10 pA increments. The first action potential that appeared on the 5 ms time point was analyzed. A curve of dV/dt was created for that trace, and the 30 V/s point in the rising slope of the action potential was considered as threshold (Kaphzan et al., 2013).

AP amplitude was measured from the equipotential point of the threshold to the spike peak, while AP duration was measured at the point of half-amplitude of the spike. The mAHP (medium after-hyperpolarization) was measured using prolonged (3 s), high-amplitude (3 nA) somatic current injections to initiate time-locked action potential trains of 50 Hz frequency and duration (10-50 Hz, 1 or 3 s) in pyramidal cells. These action potential trains generated prolonged (~20 s) AHPs, the amplitudes and integrals of which increased with the number of action potentials in the spike train. AHP was measured from the equipotential point of the threshold to the anti-peak of the same spike (Gulledge et al., 2013).

Series resistance, input resistance, and membrane capacitance were monitored during the entire experiment. Changes in these parameters (which were monitored throughout the entire duration of the experiment) greater than 10% were criteria for exclusion of data. AU experimental analyses were performed in a blind manner; the identity of the mouse from which neurons were recorded (PERK shRNA or scrambled) was not known to the person conducting the experiments and measurements.

Behavioral Procedures
Attenuation of Neophobia (Novel Taste Learning).

The rats were separated into individual housing cages and underwent a 3-day water-restriction training session, in which once a day for 20 min, they were offered 20 ml of water from two pipettes, each containing 10 ml. On the fourth day, the control group received water and the experimental group was exposed to a novel taste (0.1% (w/v) sodium saccharin) (Rosenblum et al., 1993). After two successive days of water-restriction training, the rats were tested in a multiple choice test involving two pipettes of water and two of saccharin. The multiple choice test was repeated during 3 successive days. The behavioral data are presented in terms of preference index, expressed as a percentage, [ml saccharin/(ml water plus ml saccharin)]× 100, in which the quantities are those consumed during each test. The behavioral procedure is illustrated in the top part of FIGS. 2, 3, and 4.

Conditioned Taste Aversion (CTA).

CTA experiments were performed as described previously (Elkobi et al., 2008; Stern et al., 2013). Briefly, after a 3-day training to drink from pipettes as described above, on the fourth day, rats received either water or 0.3% NaCl (the conditioned stimulus; CS), and 40 min after termination of drinking both groups received the unconditioned stimulus (UCS) in the form of an intraperitoneal injection of the malaise-inducing agent LiCl (0.075 M, 1% of body weight). The rats then received water for two days, and then underwent a taste preference test that involved a 20-min exposure to a choice of water or 0.3% NaCl in different pipettes. The aversion index to the novel taste is defined as the amount of water consumed divided by the total fluid consumption, expressed as a percentage, [(water volume/(water+NaCl) volume]×100. The behavioral procedure is illustrated in the top part of FIGS. 2, 3, and 4.

Water T-maze Position Discrimination and Arm Reversal Procedure

The position discrimination and reversal learning task were conducted in a water T-maze pool. In position discrimination learning rats were required to learn left-right discrimination with the choice of one of the arms reinforced by escaping onto a platform, and for reversal learning the two reinforcement contingencies were switched so that the choice of the opposite arm was reinforced. At the start of each trial the rat was placed in the starting arm, facing the wall opposite the cross piece, and allowed to swim and choose between the two arms. If the rat chose the correct arm it was allowed to remain on the platform for 10 s after which it was removed from the maze to a holding cage for the 10-s inter-trial interval. If the wrong arm was chosen, the rat was confined to the arm for approximately 20 s and then removed from the maze to a holding cage for the duration of the inter-trial interval. Each rat was trained until it reached a criterion of five consecutive correct trials. After 24 h each rat was first tested on the position discrimination of the previous day in probe trial, in which the platform is removed from the maze. If the reinforced arm was chosen then the rat was trained for the reversal of that discrimination, i.e. the platform was moved to the opposite arm, if the non-reinforced arm was chosen, the rat was re-trained as on the previous day, and tested again 24 h later. The rat was then trained on the reversal of this discrimination, i.e., the platform was located in the opposite arm, until the criterion was met. Other than that, training continued exactly as on the previous day. The arm chosen on each trial and the number of trials to meet the criterion on the initial discrimination and reversal were recorded for each rat.

Trace Fear Conditioning

Model chambers measuring 25×25×25 cm internally (Panlab, Harvard Apparatus) were located inside a larger, insulated plastic cabinet that excluded external light and noise. For the trace fear conditioning protocol, mice were placed in a chamber (with light [20 W bulb] and a 16 bar metal grid floor) for 120 s, after which the mice received a 2.9 kHz tone, applied for 20 s at 80 dB (conditioned stimulus) and a 0.5 mA footshock applied for 2 s (unconditioned stimulus) 20 s following the end of the conditioned stimulus. This protocol was repeated 5 times, where each tone-shock presentation was separated by a 2-minute interval. After administration of the last shock, animals remained in the chamber for 2 minutes before they were taken back to the home cage. The chambers were cleaned with 10% ethanol between successive sets of mice. Animals from control and treatment groups were randomized between the 4 different chambers. For context test 24 h after conditioning, mice were placed in the conditioning chamber and kept in the cage for 300 s without tone or foot shock. For tone-trace test 48 h after conditioning, animals were put in chambers, but the grid floor was hidden with black plastic to create another context, and the animals were presented with the tones as in the conditioning day. Animal behavior was recorded, and the data were analyzed by Freeze Frame 3.0 software (Coulbourn Instruments). The indication for fear memory was percentage of time spent freezing. We used a Shapiro-Wilk test as numerical means of assessing normality, Independent sample t-test was used as a parametric test, and for non-parametric equivalent, Mann-Whitney U Test was used. Exclusion/Inclusion criteria: Cannula and injection site were determined blindly. Animals were serially numbered, and injection or cannulation site were determined. Animals with misplaced injections were excluded. The experimenter who determined injection or cannula site was blind to the treatment.

Statistical Analysis

Data are expressed as mean±SEM. For normally distributed data statistical significance was determined with repeated measures one way ANOVA. For post-hoc comparison the least significant difference (LSD) test was used with a level of p<0.05. For abnormally distributed data we used Friedman's test followed by post hoc analysis using Wilcoxon signed-rank tests with a Bonferroni correction applied, p<0.05 for statistically significant differences. Student's t-test was used to examine the differences between groups.

Experimenters were blinded to the group and treatment during testing and scoring. To decide about the sample size in our behavioral, electrophysiological, imaging and biochemical experiments we followed the standard sample sizes used in similar experiments in each of the relevant fields in the literature. Calculated statistical values are presented as means±S.E.M. Differences in mean values were assessed with appropriate ANOVA (one-way and repeated measures) followed by multiple comparisons. For comparisons between two groups, data were analyzed using Student's t-test. Differences between means were considered statistically significant if p<0.05.

Examples 1 to 4 Show the Effect of PERK Inhibition or Knockdown in the IC.

Example 1

PERK is the Main Kinase to Determine Basal Levels of p-eIF2α in Neurons

First, we hypothesized that local reduction in the expression of the different eIF2α kinases would reduce eIF2α phosphorylation in neurons. Towards that end, we generated viral vectors expressing shRNA sequences that can efficiently reduce the expression of three of the dominant eIF2α-regulating kinases in the brain (PERK, PKR, and GCN2, depicted in FIG. 1A). Target validation was performed in 3T3 cells, which were infected with viruses expressing 3 different shRNA cassettes for either one of the kinases or a control cassette harboring a scrambled sequence. The data presented are of the shRNA cassettes that could competently and specifically shut down kinase expression, compared to the control virus (PERK, GCN2, and PKR levels were reduced by 79%±18.1, 97%±19.3, and 57%±7.2, respectively; n=4, t(6)=−3.569, p=0.02 for PERK reduction; t(6)=−5.312, p=0.01 for GCN2 reduction; and t(6)=−2.596, p=0.04 for PKR reduction t-test; FIG. 1B). As an additional control for the specificity of each shRNA cassette, we examined its effect on the expression of the other kinases, and found that each shRNA cassette is indeed specific to its target, and does not affect the expression of the other kinases (data not shown).

Next, the effect of reduction in expression of each kinase on phosphorylation of eIF2α on Ser51 residue in 3T3 cells was tested (FIG. 1C). Of the three kinases, PERK knockdown resulted in the strongest reduction in p-eIF2α levels (63%±4.9, n=4, t(6)=5.196, p=0.007, t-test), whereas the knockdown of PKR or GCN2 resulted in a moderate non-significant reduction in p-eIF2α levels (35%±6.2, and 35%±19.1 respectively, p>0.05, n=4). Furthermore, the effect of the reduction of expression levels of each kinase on the phosphorylation of eIF2α was examined in primary neuronal culture, and similarly to the results in 3T3 cells, PERK knockdown, but not that of PKR or GCN2, resulted in a significant reduction in p-eIF2α levels (59%±7.5 reduction in p-eIF2α levels by PERK shRNA lentivirus, compared to scrambled shRNA lentivirus, p=0.03; t(8)=7.091, no effect in PKR or GCN2 knockdown, n=4-10; FIG. 1D).

Example 2

Local Inhibition of PERK in the IC Using GSK2606414 Reduces p-eIF2α Levels and Enhances Both Positive and Negative Forms of Taste Memory Novel taste learning induces a reduction in eIF2α phosphorylation in the insular cortex (IC) (Stern et al., 2013). We tested the hypothesis that local inhibition of the eIF2α kinase PERK in the IC would reduce p-eIF2α levels, and would mediate enhancement of taste memory. Stereotactic injection of PERK inhibitor GSK2606414 (1 μl, 100 nM; Axten et al., 2012) to the IC resulted in a significant reduction in p-eIF2α levels by 40% compared to vehicle (t(28)=−2.251, p=0.032, t-test, n=15 (each group)), data not shown; representative image indicating the guiding cannula placement and the injection site is shown in FIG. 2A). In addition to the reduction in p-eIF2α we observed a 30% reduction in ATF4 protein levels (data not shown, t(30)=2.217, n=16 in each group, p=0.034, t-test).

To test the effect of PERK inhibition on the behavioral level, PERK inhibitor (1 μl of GSK2606414, 100 nM) was injected to the IC 20 min prior to exposure to a novel taste, in either an incidental taste learning procedure (0.1% saccharin) or a conditioned taste aversion (CTA) procedure using 0.3% NaCl, coupled to 0.075 M LiCl i.p. injection, as described previously (Rosenblum et al 1993). Memory was assessed two days after learning.

In the incidental taste learning procedure, PERK inhibition resulted in better memory of the novel taste (0.1% saccharin) in the PERK inhibitor-injected group compared with the vehicle-injected group on test day1, as demonstrated by the higher elevation in the preference index (83%±2.2 vs. 64%±11.1, respectively; FIG. 2B, n=8 in each group, t(14)=2.505, p=0.04 t-test). In the CTA procedure, PERK inhibitor-injected animals had better memory (higher aversion) than vehicle-injected animals (72%±3.5 vs. 54%±6.5, n=8 in each group, t(14)=2.325, p=0.04 t-test). However, extinction of CTA was not affected by the single injection of PERK inhibitor during CTA (ANOVA repeated measures, FIG. 2C). Total drinking volumes were similar in both experimental groups throughout the behavioral procedure (data not shown).

Example 3

PERK Knockdown in the IC Decreases p-eIF2α, Enhances Positive and Negative Forms of Taste Memory, and Increases Behavioral Plasticity We next wanted to determine if knockdown of PERK expression levels would result in decreased p-eIF2α levels and enhanced memory using the viral vector tested in cells. Our hypothesis was that a prolonged reduction in PERK expression and p-eIF2α levels due to permanent expression of the shRNA cassette in a specific brain structure of the adult brain could result in different effects on behavior than those observed in the PERK conditional KO mice, where PERK is eliminated in the brain post weaning (Trinh et al., 2012). Therefore, the PERK shRNA lentivirus was stereotacticaly injected to the IC of adult rats, and its effects on taste memory were assessed using the novel taste learning and the CTA procedures 7 days following the injection (FIG. 3A). A representative image indicating virus injection site is shown in FIG. 3B.

In the novel taste learning procedure, analysis of memory in the PERK knockdown animals over two consecutive days revealed a major group effect compared to the scrambled shRNA lentivirus controls, and the preference index was markedly elevated with taste familiarization from 28%±5.1 on acquisition day to 48%±5.6 and 57%±5.1 on the two consecutive memory tests conducted (n=21 in each group, Z=−2.798, p=0.005, and Z=−3.285, p=0.001 for test days 1 and 2 respectively; Friedman test, followed by Wilcoxon signed-rank post hoc analysis, Bonferroni correction, FIG. 3C). PERK knockdown in the IC also enhanced CTA memory as manifested by the elevation in the aversion index compared to scrambled sequence lentivirus controls (81%±2.2 vs. 55.9%±4.7, n=21 in each group, t(40)=−4.880, p=0.0003, t-test). Interestingly, IC PERK knockdown not only enhanced CTA memory but also improved behavioral plasticity, as observed by the major group effect on CTA extinction in the consecutive two extinction days carried following the CTA test ((F(1.724, 34.486)=20.410, p=0.01, and 0.0001 for extinction days 1 and 2 respectively, ANOVA repeated measure, FIG. 3D). Another set of animals was further tested for general, IC-independent behavioral flexibility in the arm reversal task using the water T-maze. Whereas CTA was enhanced in the PERK shRNA-injected rats as observed before (85%±7.7 vs. 59%±8.7 in the control group, n=6 in each group, t (10)=2.250, p=0.048, t-test), both the scrambled and the PERK shRNA lentivirus injected animals performed similarly in the reversal task. Total drinking volumes were similar in both experimental groups throughout the behavioral procedure (data not shown).

The effect of PERK knockdown on p-eIF2α levels in the IC was determined by immunoblots from IC punches taken according to the coordinates of the injection site (n=17, FIG. 3A). In accordance with our hypothesis, PERK levels and p-eIF2α levels were significantly reduced in the IC punches made at the coordinates of the injection site, (FIG. 3E). The reduction in p-eIF2α levels was not only significant but also negatively correlated to the elevation in aversion index, indicative of improved memory (correlation value R=−0.55, n=14, p=0.04).

Example 4

PERK does not Affect Memory Retrieval

We next sought to determine whether the PERK-mediated effect of memory enhancement is the result of improved consolidation via the decrease in p-eIF2α levels, or results from better retrieval. Therefore, the PERK shRNA lentivirus was injected to the IC 2 days after performing the CTA (0.3% NaCl coupled to injection of 0.075M LiCl), and the memory test was performed 1 week following the virus injection (FIG. 4A). Our hypothesis was that if the effect is on the learning itself, then PERK knockdown after learning would have no effect on the memory, as the learning occurred prior to virus injection and to reduction in PERK expression.

Indeed, the PERK shRNA lentivirus-injected group had the same aversion (memory) as the scrambled shRNA lentivirus-injected group (50.3%±6 in PERK shRNA injected group vs. 54.9%±9.9 in scrambled shRNA lentivirus group), clearly demonstrating that PERK knockdown and the resulting reduction in p-eIF2α levels mediate memory enhancement via improving learning, but not retrieval (FIG. 4B). As a control experiment, we divided the animals into two groups prior to virus injection, and performed novel taste learning. Clearly, we had no differences in the preference index between the two groups of naïve animals, and total drinking volumes were similar in both experimental groups throughout the behavioral procedure (data not shown).

Examples 5 to 7 Show the Effect of PERK Inhibition or Knockdown in the Hippocampus.

Example 5

Figure 5:
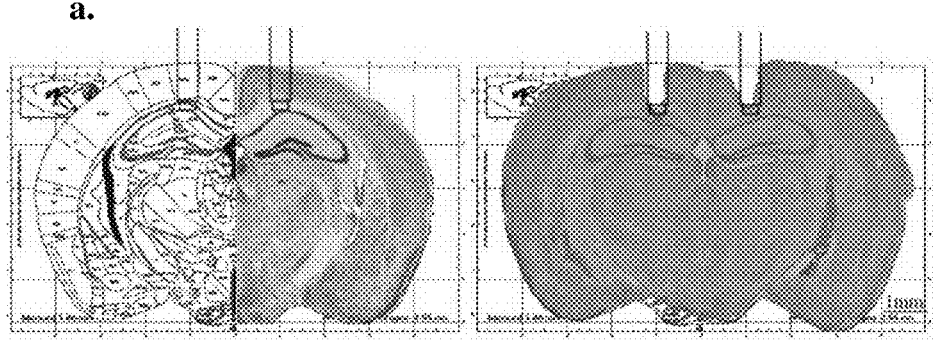
FIG. 5 shows that PERK inhibition (GSK2606414) in the CA1 enhances trace fear conditioning (TFC) memory and increases neuronal excitability. (a) Cannulation site to CA1 region. (b) Experimental design. (c) TFC protocol. (d) GSK2606414 has no effect on context memory (vehicle n=11; GSK2606414 n=13; Mann-Whitney U Test, U=58.5, p=0.451). (e) GSK2606414 enhances tone memory vehicle; GSK2606414 (*Mann-Whitney U Test, U=34, p=0.03). GSK2606414 enhances trace memory in the 20 s trace interval following tone presentation vehicle; GSK2606414 (Independent sample t-test, t (21.086)=−2.672, *p=0.014. (f) GSK2606414 increases the firing index in treated neurons (n=21) vs. vehicle controls (n=19) (Two-way repeated measure ANOVA, $F_{(1, 18)}$=41.24; *p=4.8×10$^{-6}$). (g) GSK2606414 reduces mAHP in treated neurons n=21) vs. vehicle controls (n=19), (Independent sample t-test, $t_{(31.401)}$=−4.255, *p=0.00017).
Figure 5:
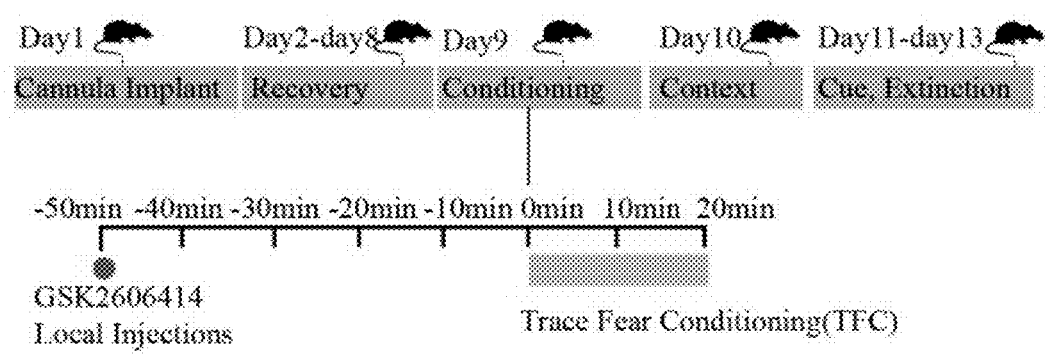
Figure 5:
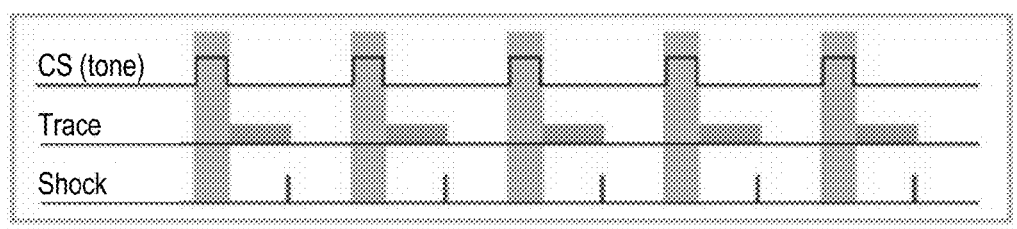
Figure 5:
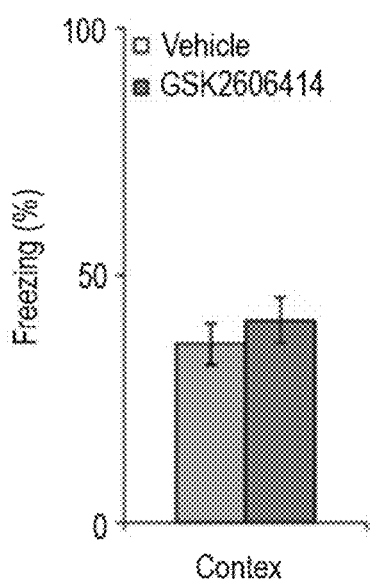
Figure 5:
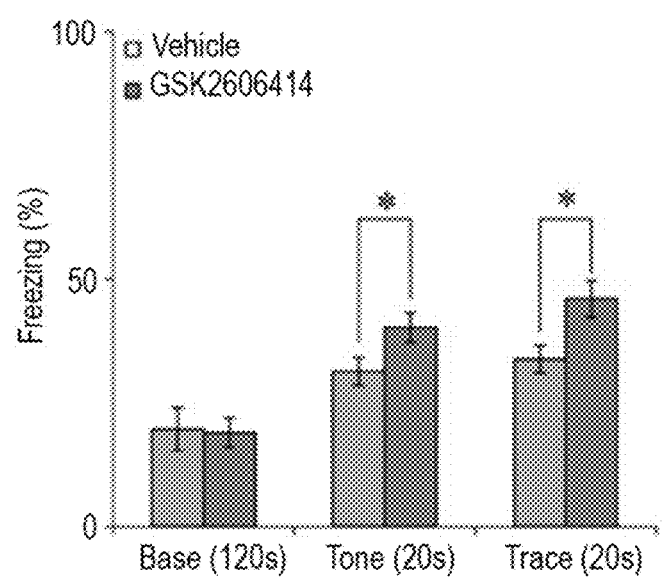
Figure 5:
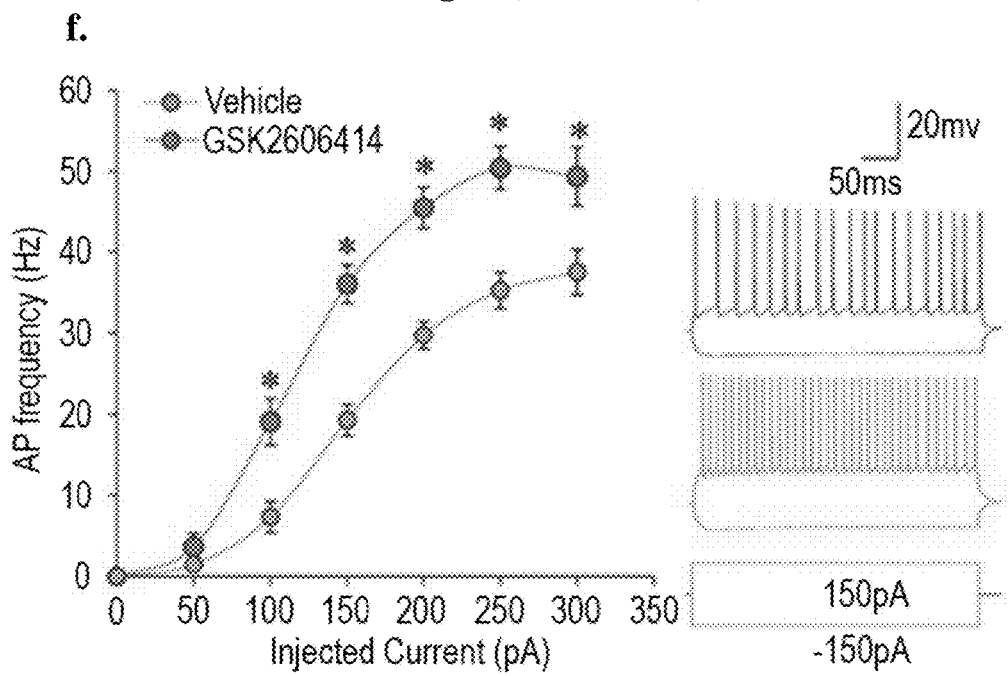
Figure 5:
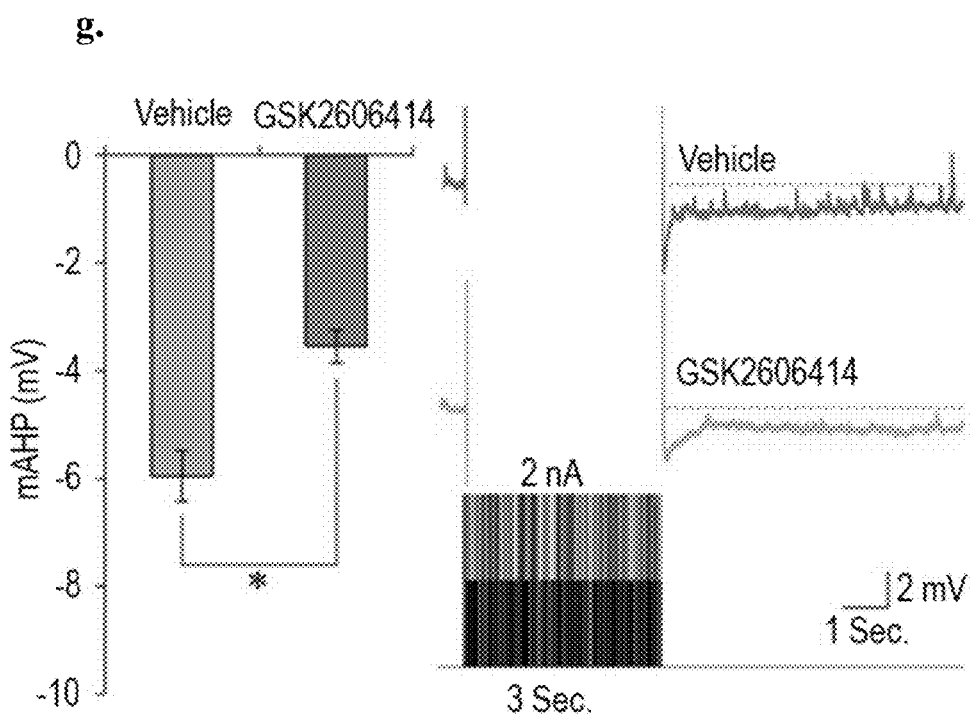
Figure 6:
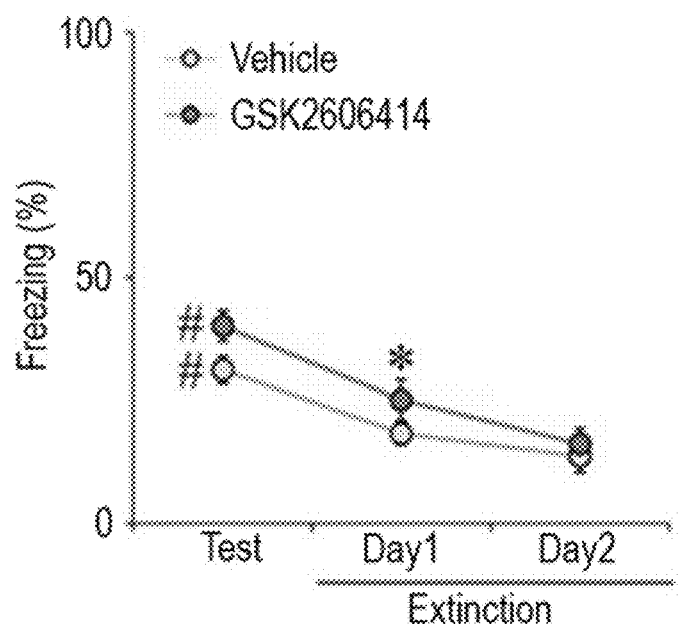
FIG. 6 shows that GSK2606414 reduces p-eIF2α levels, increases AP characteristics, with normal extinction. (a) Cue extinction in GSK2606414 (F (1.906, 22.87)=19.924, #p=1.22×10$^{-5}$) and vehicle (Friedman Test, $\chi^2$ (2)=15.273, #p=0.0005) treated animals. (b) Trace extinction in GSK2606414 (ANOVA with repeated measures, F (1.973, 23.675)=37.264, #p=5.28×10$^{-8}$) and vehicle (Friedman Test, $\chi^2$ (2)=6.61, #p=0.037) treated animals. (c) Resting membrane potential (Independent sample t-test, $t_{(33.487)}$=1.482, p=0.148). (d) Input resistance in GSK2606414 treated neurons vs. vehicle controls (Independent sample t-test, $t_{(37.682)}$=−1.22, p=0.23. (e) Action potential threshold in GSK2606414 treated neurons n=21) vs. vehicle controls (n=19), Mann-Whitney U Test, U=119.5, *p=0.03. (f) Action potential amplitude in GSK2606414 treated neurons (n=21) vs. vehicle controls (n=19), Independent-Sample t-test, $t_{(33.538)}$=−2.279, *p=0.029. (g) Action potential mid width in GSK2606414 treated neurons (n=21) vs. vehicle controls (n=19), Mann-Whitney U Test, U=108.5, *p=0.014. (h) Total PERK protein levels in CA1 punches after GSK2606414 infusion (Independent sample t-test, $t_{(14)}$=−0.832, p=0.419). (i) p-eIF2α in adult mice following GSK2606414 infusion into the CA1 region (Independent sample t-test, $t_{(14)}$=2.235, *p=0.042).
Figure 6:
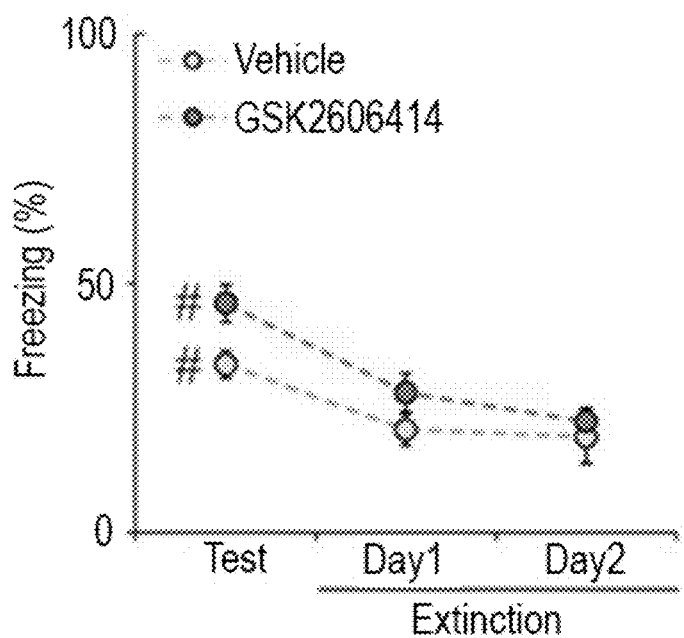
Figure 6:
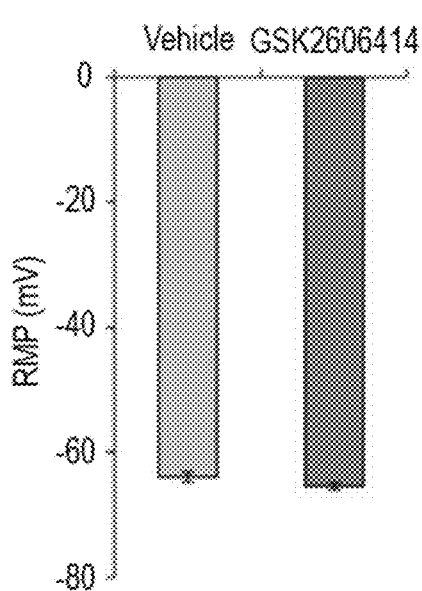
Figure 6:
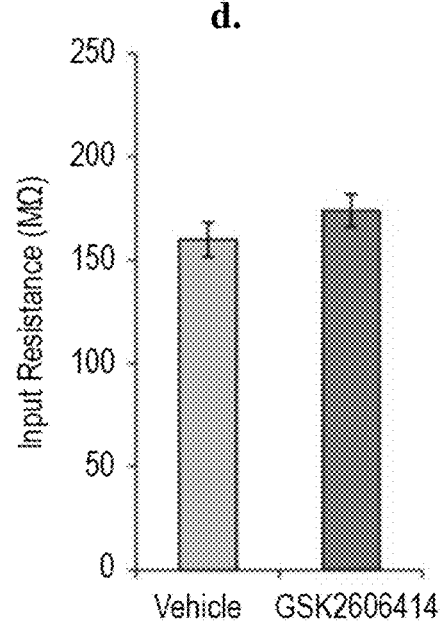
Figure 6:
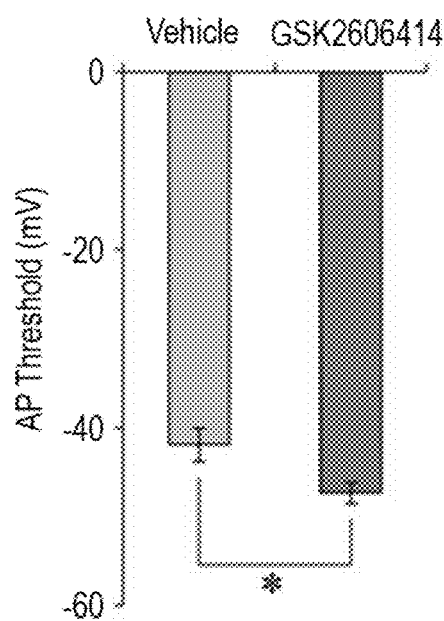
Figure 6:
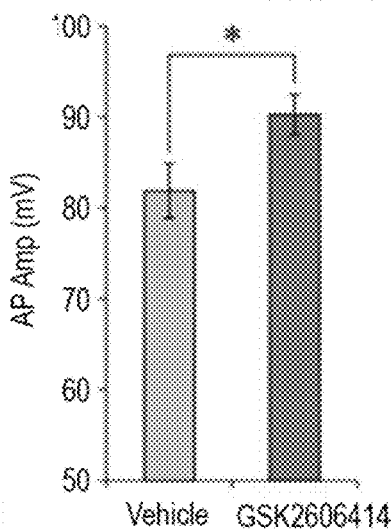
Figure 6:
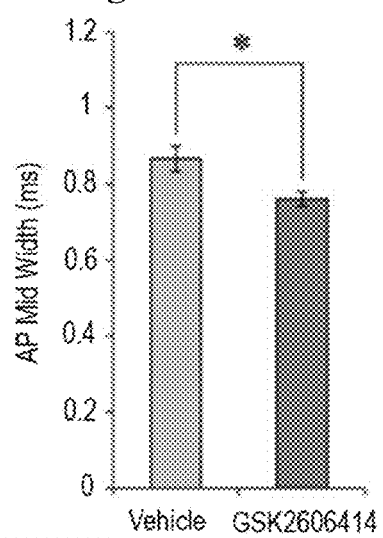
Figure 6:
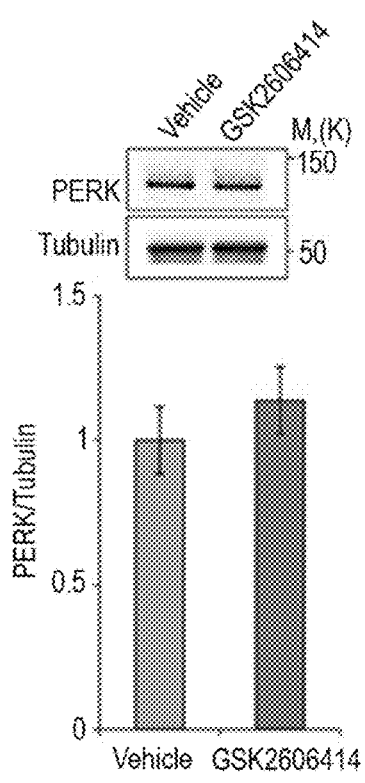
Figure 6:
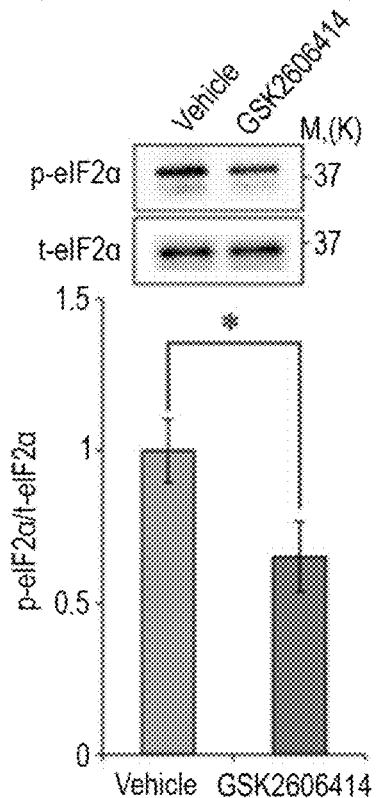

PERK Inhibition in the CA1 Region Enhances Hippocampal Memory and Neuronal Excitability In Examples 1 to 4, we have shown that cortex-specific reduction of PERK activity or expression enhances memory and behavioral flexibility *(Ounallah-Saad et al., 2014). Here, we first tested whether a similar phenomenon would be observed in the adult hippocampus, a brain structure necessary for different cognitive functions in human and rodents. Towards that aim, we reduced PERK activity in the adult hippocampus by bilaterally infusing a PERK-specific inhibitor (GSK2606414, 100 nM) to the CA1 region (FIG. 5a) 50 min. prior to the acquisition phase (FIG. 5b) of the trace fear conditioning paradigm (FIG. 5c). Long-term memory was tested 24 h after conditioning by re-exposing the animals to the training context. The tone-trace memory was tested 48 h following conditioning by putting the animals in a new context and presenting the tone from the training day. In the tone-trace test 48 h after conditioning, PERK inhibition resulted in enhanced freezing during tone presentation as well as in the trace interval following the tone compared with vehicle-treated animals (FIG. 5e). However, context memory was not altered, as demonstrated by a similar freezing percentage in both groups (FIG. 5d). In addition, reduction of PERK activity at the time of conditioning had no effect on extinction (FIG. 6a,b).

In order to test possible neuronal mechanisms underlying the cognitive enhancement observed by reduction in PERK activity, we examined intrinsic neuronal properties using whole cell patch clamp recording from pyramidal CA1 neurons following PERK inhibition. PERK inhibition (GSK2606414, 100 nM) in acute mouse-derived hippocampal slices resulted in increased neuronal excitability, reflected in increased action potential (AP) frequency as a function of increased current steps (FIG. 5f). Moreover, PERK inhibition caused a significantly reduced mAHP, further contributing to the increased neuronal excitability (FIG. 5g). The effect of PERK inhibitor GSK2606414 on neuronal passive properties was examined by adding the inhibitor to the pipette solution. Neither resting membrane potential (RMP) nor input resistance was changed (FIG. 6c,d). However, PERK inhibition hyperpolarized the AP threshold and produced longer and wider AP (FIG. 6e,f,g). On the biochemical level, PERK inhibition had no effect on total PERK levels (FIG. 6h), but resulted in significant reduction in p-eIF2α levels (FIG. 6i).

Example 6

Figure 7:
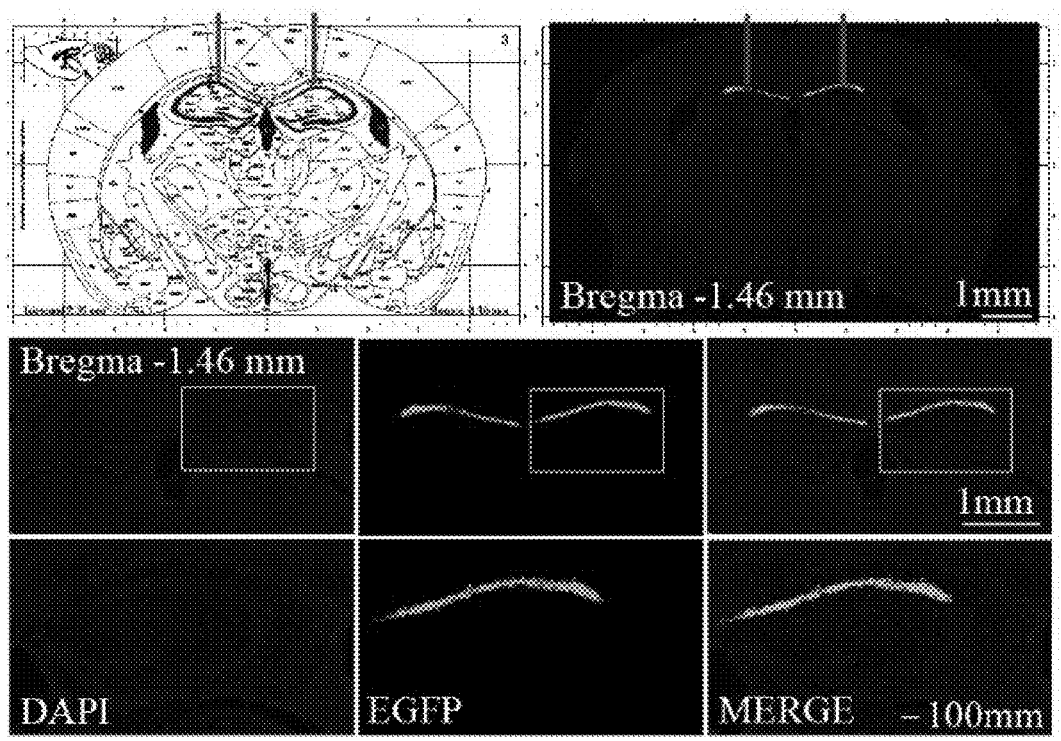
FIG. 7 shows that genetic reduction of PERK expression in the CA1 enhances trace fear conditioning memory. (a) Immunohistochemistry for EGFP reporter demonstrates that PERK shRNA AAV expression is restricted to the CA1 region of the hippocampus. (b) Context memory is similar in animals injected into the CA1 regions of the hippocampus with PERK shRNA or scrambled control. (c) PERK reduction enhances tone (Independent sample t-test, for tone: $t_{(20)}$=−2.436, *p=0.024) and trace (Independent sample t-test, for trace: $t_{(20)}$=−2.69, *p=0.014) memory in animals injected into the CA1 with PERK shRNA compared with scrambled control. Data presented are mean freezing percent±SEM.
Figure 7:
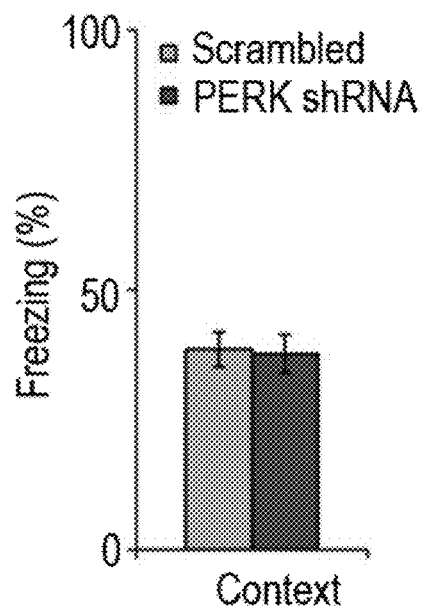
Figure 7:
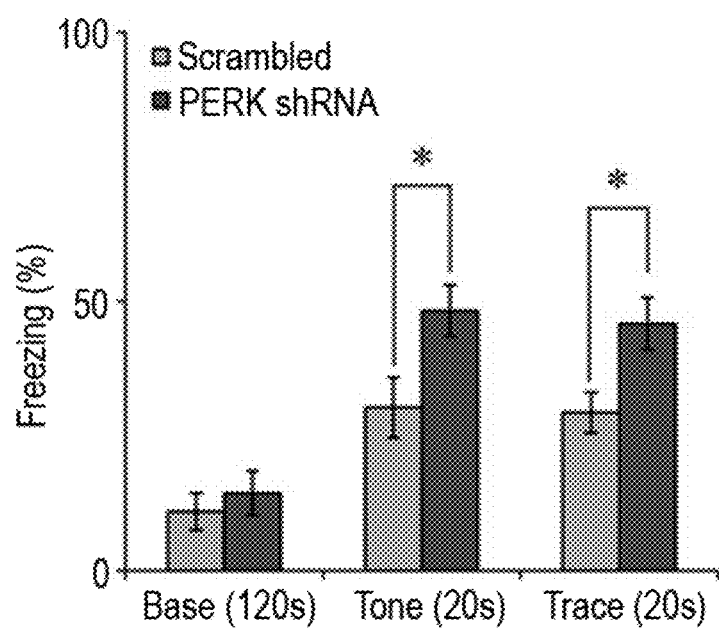

Reduction in CA1 PERK Levels Enhances Hippocampal-dependent Memory and Neuronal Excitability To examine whether genetic reduction of PERK expression levels yields similar results to those obtained with pharmacological inhibition of its activity, we bilaterally injected an adeno-associated virus (AAV) expressing PERK-specific shRNA into the CA1 region of the hippocampus (FIG. 7a, FIG. 8e,f). The effect on hippocampal-dependent learning was examined using the trace fear conditioning paradigm as described in FIG. 5. Indeed, the cognitive enhancement observed following genetically reducing PERK levels was similar to that observed following CA1-specific inhibition of PERK activity: while tone and trace memory were significantly enhanced in the animals injected with PERK shRNA AAV compared to control animals injected with scrambled (SCR) shRNA AAV (FIG. 7c), context memory was unaffected (FIG. 7b). The extinction of tone and trace memory in animals treated with PERK shRNA was normal (FIG. 8a,b). On the biochemical level, both PERK expression levels and p-eIF2α levels were reduced in CA1 punches from PERK shRNA AAV-injected animals in comparison to SCR AAV-injected animals (FIG. 8c,d).

Figure 9:
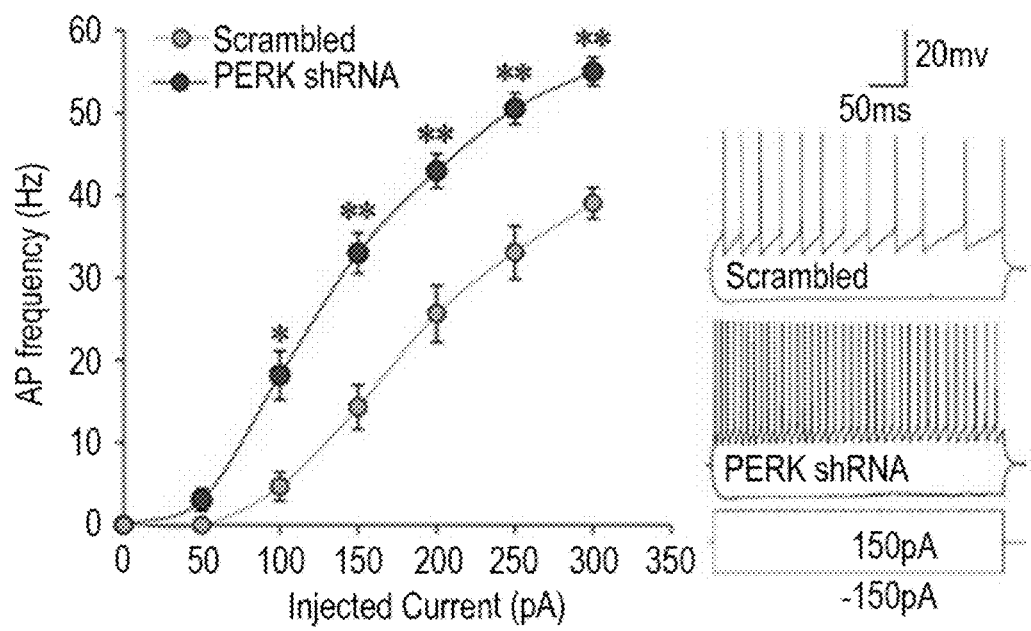
FIG. 9 shows that genetic reduction of PERK expression in the CA1 increased neuronal excitability. (a) AP frequency was increased in PERK shRNA AAV infected neurons (n=14) vs. scrambled AAV infected control neurons (n=13) (Two-way repeated measure ANOVA, $F_{(1,12)}$=25.45; *p=0.00029). (b) mAHP was smaller in PERK shRNA AAV infected neurons n=14) vs. scrambled AAV control neurons (n=13), Independent sample t-test, $t_{(25)}$=−5.71, *p=6×10$^{-6}$. Data presented are mean freezing percent±SEM.
Figure 9:
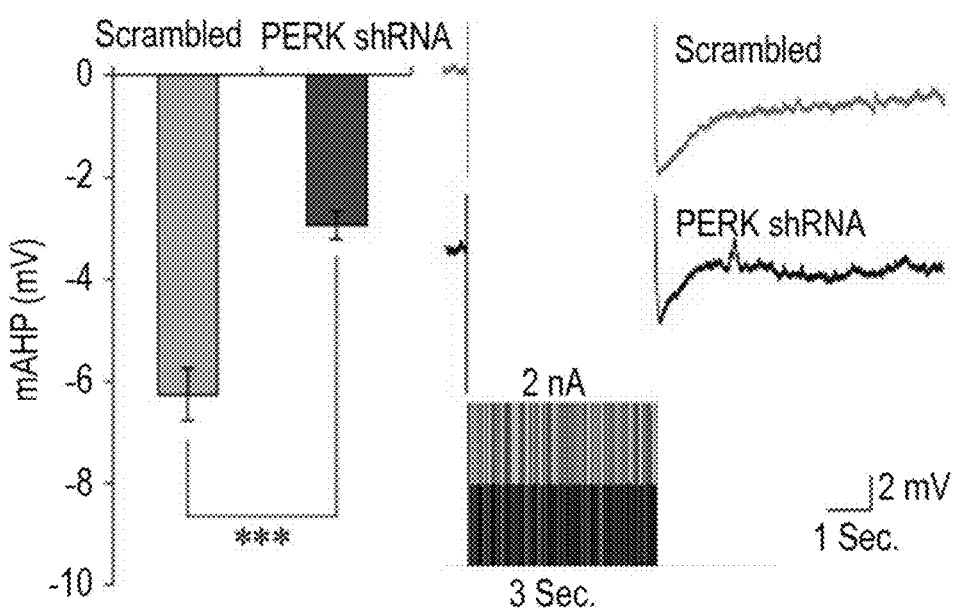
Figure 10:
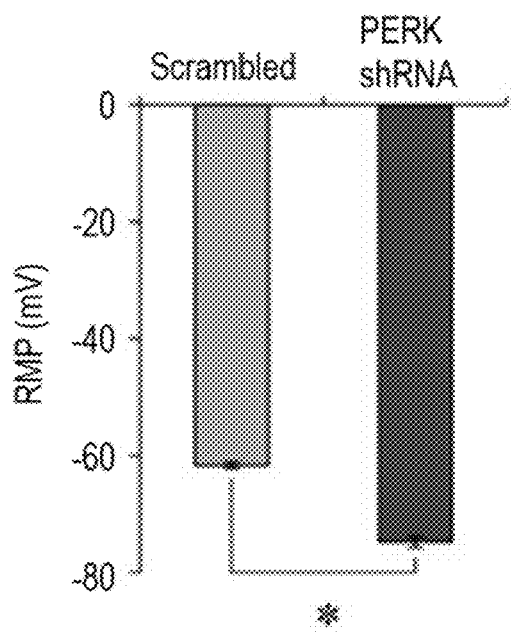
FIG. 10 shows that PERK reduction alters passive neuronal properties and AP characteristics. Intrinsic properties tested PERK shRNA infected neurons: (a) RMP (Independent sample t-test $t_{(25)}$=−11.45, *p=2.6×10$^{-11}$). (b) Input resistance (Independent sample t-test, $t_{(25)}$=−0.50, p>0.05). (c) AP threshold (Independent sample t-test, $t_{(25)}$=3.19, *p=0.0038). (d) AP amplitude (Independent sample t-test, $t_{(25)}$=−1.16, p=0.256). (e) AP mid width (Mann-Whitney U Test, U=79, p>0.05).
Figure 10:
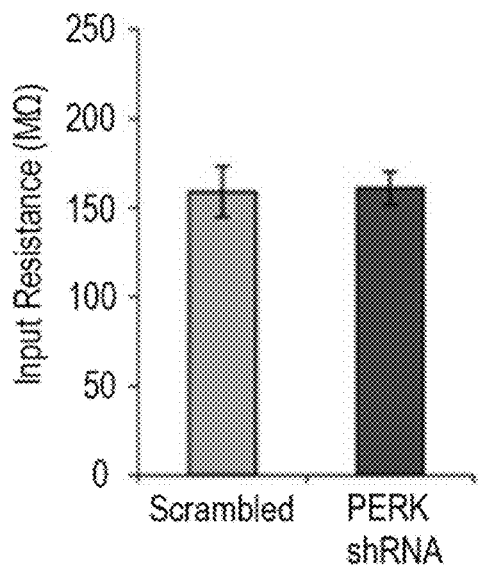
Figure 10:
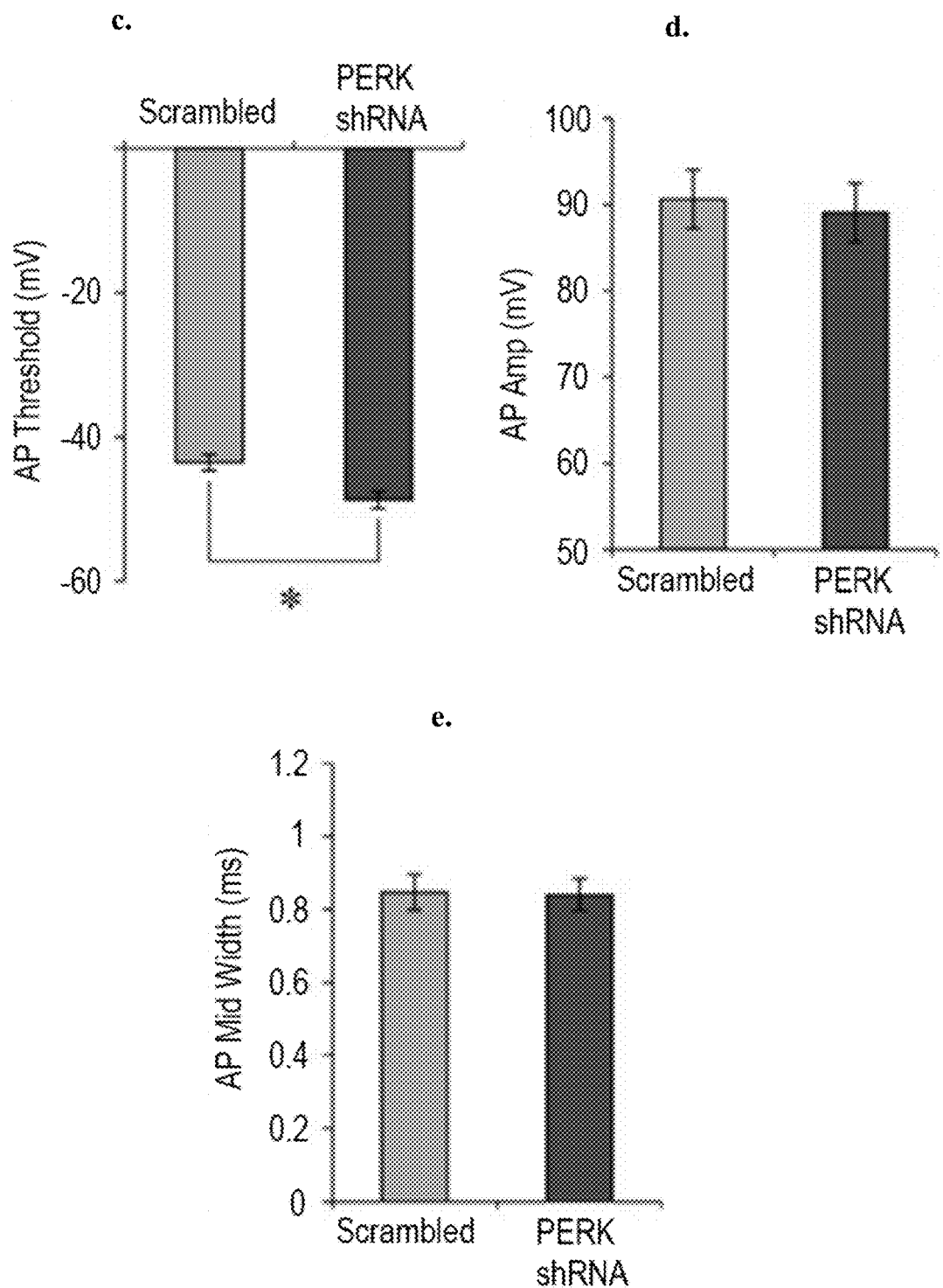

The changes in intrinsic properties were similar to those observed with the PERK inhibitor. The reduction of PERK expression levels in the CA1 region resulted in increased neuronal excitability (FIG. 9). Action potential (AP) frequency was significantly higher in neurons infected with PERK shRNA AAV compared to scrambled AAV in response to injection of increased current steps (FIG. 9a). In addition, infection of neurons with PERK shRNA AAV resulted in significant reduction in mAHP compared to neurons infected with SCR AAV, with a mean difference of 3.3 mV (FIG. 9b). Additionally, the passive properties of neurons infected with PERK shRNA were examined. Interestingly, in contrast to transient inhibition of PERK with GSK2606414, permanent reduction in PERK expression levels resulted in a more hyperpolarized resting membrane potential (RMP) and no effect on AP amplitude and AP mid width compared to the neurons infected with SCR AAV (FIG. 10a,d,e), and similarly to PERK inhibition, PERK reduction had no effect on input resistance and hyperpolarized the AP threshold (FIG. 10b,c).

Example 7

PERK Reduction in the CA1 Region of the Hippocampus Reverses Memory Deterioration and Decreased Neuronal Excitability Associated with Age Taken together, our results above demonstrate that reduced PERK expression levels or activity improves hippocampal-dependent memory and increases neuronal excitability. Since PERK mRNA levels are increased in aged mice (FIG. 11c), we next wished to examine if PERK knockdown in hippocampus of older (12-month) mice would have a beneficial effect on behavioral performance. To test this hypothesis, PERK shRNA AAV or SCR AAV was bilaterally injected into the CA1 region of the hippocampus of 10-month-old mice, and behavioral performance was assessed at the age of 12 months. In addition, 3-month-old mice were bilaterally injected with SCR AAV into the CA1 region of the hippocampus, and assessed for behavioral performance at the age of 5 months, thus enabling the assessment of the effect of age. Context memory as measured in the trace fear conditioning paradigm was impaired in 12-month-old animals injected with SCR AAV compared to 5-month-old animals injected with the same vector (FIG. 12a). However, administration of PERK shRNA AAV to 12-month-old animals prevented this age-induced memory decline, resulting in context memory performance similar to 5-month-old animals injected with SCR AAV (FIG. 12a). A similar rescue was observed in the tone-trace memory test, where 12-month-old animals injected with PERK shRNA AAV performed at least as well as 5-month-old animals injected with SCR AAV, overcoming the age-induced memory impairment (FIG. 12b). Extinction was normal in both 12-month-old animals injected with PERK shRNA and with SCR control (FIG. 11a,b).

On the physiological level, AP frequency in infected neurons derived from 12-month-old animals injected with SCR AAV was lower than in infected neurons from 5-month-old animals treated with the same vector (FIG. 12c), reflecting normal physiological changes that accompany aging, as previously reported (Kumar and Foster, 2007; Gant and Thibault, 2009). However, this aging-induced decrease in AP frequency was prevented in infected neurons derived from 12-month-old animals treated with PERK shRNA AAV, and AP frequency was even higher in these animals compared to 5-month-old animals treated with SCR AAV (FIG. 12c). Furthermore, the effect of normal aging on neuronal excitability was reflected in the mAHP that was significantly increased in neurons derived from 12-month-old animals treated with SCR AAV compared with neurons derived from 5 month old animals treated with the same vector (FIG. 12d). However, treatment with PERK shRNA AAV not only reversed this increase in 12-month-old animals but also resulted in significantly smaller mAHP than in the 5-month-old animals treated with SCR AAV (FIG. 12d).

When assessing passive properties, RMP in neurons from 12-month-old animals infected with either PERK shRNA AAV or SCR AAV was of similar levels, and more hyperpolarized compared to neurons derived from 5-month-old animals treated with SCR AAV (PERK shRNA vs. SCR, FIG. 11d). Input resistance was not different between neurons derived from SCR and PERK shRNA infected 12-month-old animals, but was higher in the 12-month-old groups compared to the neurons derived from the 5-month-old animals infected with SCR AAV (FIG. 11e). Moreover, a ~5 mV depolarization in AP threshold in neurons from the 12-month-old animals infected with SCR AAV compared to the 5-month-old animals treated with the same vector was completely rescued in 12-month-old animals treated with PERK shRNA AAV (FIG. 11f). These findings coincide with a similar rescue of ~8 mV AP amplitude reduction in the 12-month-old mice treated with PERK shRNA AAV (FIG. 11g), while no significant alteration of AP mid with was observed (FIG. 11h). These results suggest that reducing PERK levels by treatment with PERK shRNA AAV increase cellular excitability in mechanisms additional to mAHP reduction (FIG. 12d,e). Taken together, our findings show that reducing PERK expression in the CA1 region prevents age-related memory deterioration, possibly by rescuing the decrease in age-related neuronal excitability.

REFERENCES

Axten J M et al (2012) Discovery of 7-methyl-5-(1-{[3-(trifluoromethyl)phenyl]acetyl}-2,3-dihydro-1H-indol-5-yl)-7H-pyrrolo[2,3-d]pyrimidin-4-amine (GSK2606414), a potent and selective first-in-class inhibitor of protein kinase R (PKR)-like endoplasmic reticulum kinase (PERK). J Med Chem 55.7193-7207.

Barki-Harrington L, Elkobi A, Tzabary T, Rosenblum K (2009) Tyrosine phosphorylation of the 2B subunit of the NMDA receptor is necessary for taste memory formation. J Neurosci 29.9219-9226.

Costa-Mattioli M, Gobert D, Stern E, Gamache K, Colina R, Cuello C, Sossin W, Kaufman R, Pelletier J, Rosenblum K, Krnjevic K, Lacaille J C, Nader K, Sonenberg N (2007) eIF2alpha phosphorylation bidirectionally regulates the switch from short- to long-term synaptic plasticity and memory. Cell 129.195-206.

Disterhoft, J. F. & Oh, M. M. Alterations in intrinsic neuronal excitability during normal aging. *Aging Cell.* 6, 327-336 (2007).

Disterhoft, J. F. & Oh, M. M. Pharmacological and molecular enhancement of learning in aging and Alzheimer's disease. *J. Physiol. Paris* 99, 180-192 (2006).

Elkobi A, Ehrlich I, Belelovsky K, Barki-Harrington L, Rosenblum K (2008) ERK-dependent PSD-95 induction in the gustatory cortex is necessary for taste learning, but not retrieval. Nat Neurosci 11.1149-1151.

Gal-Ben-Ari S, Kenney J W, Ounalla-Saad H, Taha E, David O, Levitan D, Gildish I, Panj a D, Pai B, Wibrand K, Simpson T I, Proud C G, Bramham C R, Armstrong J D, Rosenblum K (2012) Consolidation and translation regulation. Learn Mem 19.410-422.

Gant, J. C. & Thibault, O. Action potential throughput in aged rat hippocampal neurons: regulation by selective forms of hyperpolarization. *Neurobiol. Aging* 30, 2053-2064 (2009).

Gulledge, A. T. et al. A sodium-pump-mediated afterhyperpolarization in pyramidal neurons. *J. Neurosci.* 33, 13025-13041 (2013).

Kaphzan, H. et al. Genetic reduction of the alpha1 subunit of Na/K-ATPase corrects multiple hippocampal phenotypes in Angelman syndrome. *Cell. Rep.* 4, 405-412 (2013).

Kumar, A. & Foster, T. C. in *Brain Aging: Models, Methods, and Mechanisms* (ed Riddle, D. R.) (Taylor & Francis Group, LLC, Boca Raton (Fla.), 2007).

Lois C, Hong E J, Pease S, Brown E J, Baltimore D (2002) Germline transmission and tissue-specific expression of transgenes delivered by lentiviral vectors. Science 295.868-872.

Ma T, Trinh M A, Wexler A J, Bourbon C, Gatti E, Pierre P, Cavener D R, Klann E (2013) Suppression of eIF2alpha kinases alleviates alzheimer's disease-related plasticity and memory deficits. Nat Neurosci 16.1299-1305.

Moreno J A, Radford H, Peretti D, Steinert J R, Verity N, Martin M G, Halliday M, Morgan J, Dinsdale D, Ortori C A, Barrett D A, Tsaytler P, Bertolotti A, Willis A E, Bushell M, Mallucci G R (2012) Sustained translational repression by eIF2alpha-P mediates prion neurodegeneration. Nature 485.507-511.

Moreno, J. A. et al. Oral treatment targeting the unfolded protein response prevents neurodegeneration and clinical disease in prion-infected mice. *Sci. Transl. Med.* 5, 206ra138 (2013).

Oh, M. M., Oliveira, F. A. & Disterhoft, J. F. Learning and aging related changes in intrinsic neuronal excitability. *Front. Aging Neurosci.* 2, 2 (2010).

Paxinos, G. & Watson, C. (2006) The rat brain in stereotaxic coordinates, 6th ed. Elsevier.

Radford, H., Moreno, J. A., Verity, N., Halliday, M. & Mallucci, G. R. PERK inhibition prevents tau-mediated neurodegeneration in a mouse model of frontotemporal dementia. *Acta Neuropathol.* 130, 633-642 (2015).

Rosenblum K, Meiri N, Dudai Y (1993) Taste memory. The role of protein synthesis in gustatory cortex. Behav Neural Biol 59.49-56.

Segev, Y., Michaelson, D. M. & Rosenblum, K. ApoE epsilon4 is associated with eIF2alpha phosphorylation and impaired learning in young mice. *Neurobiol. Aging* 34, 863-872 (2013).

Stern E, Chinnakkaruppan A, David O, Sonenberg N, Rosenblum K (2013) Blocking the eIF2alpha kinase (PKR) enhances positive and negative forms of cortex-dependent taste memory. J Neurosci 33.2517-2525.

Trinh M A, Kaphzan H, Wek R C, Pierre P, Cavener D R, Klann E (2012) Brain-specific disruption of the eIF2alpha kinase PERK decreases ATF4 expression and impairs behavioral flexibility. Cell Rep 1.676-688.

Trinh M A, Ma T, Kaphzan H, Bhattacharya A, Antion M D, Cavener D R, Hoeffer C A, Klann E (2014). The eIF2α kinase PERK limits the expression of hippocampal metabotropic glutamate receptor-dependent long-term depression. Learn Mem 21.298-304.

The invention claimed is:

1. A method for improving a cognitive function in a subject having age-related cognitive dysfunction, said method comprising administering to said subject an active agent reducing PKR-like endoplasmic reticulum kinase (PERK) activity.

2. The method of claim 1, wherein said active agent is administered locally to the cerebral cortex or hippocampus of said subject.

3. The method of claim 1, wherein said active agent is a small molecule inhibitor of the formula (I):

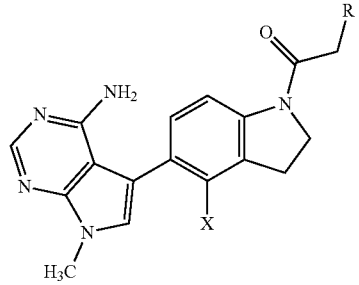

wherein
X is H or F; and
R is selected from 3-trifluoromethylphenyl, 2-pyridinyl, 3-pyridinyl, 4-pyridynyl, 2-methylpyridin-6-yl, 2-trifluoromethylpyridin-6-yl, 3-methylpyrazol-1-yl, 5-methylpyrazol-1-yl, or 3,5-dimethylpyrazol-1yl.

4. The method of claim 3, wherein X is H and R is 3-trifluoromethylphenyl (compound 1) or X is F and R is 2-methylpyridin-6-yl (compound 6), 2-trifluoromethylpyridin-6-yl (compound 8), or 3,5-dimethylpyrazol-1yl (compound 12).

5. The method of claim 1, wherein said active agent is a nucleic acid molecule that reduces the gene expression level of PERK.

6. The method of claim 5, wherein said nucleic acid molecule is an shRNA or artificial siRNA molecule comprising a nucleic acid sequence being complementary to a sequence within a nucleic acid sequence encoding said PERK, or a nucleic acid molecule encoding said shRNA or artificial siRNA molecule.

7. The method of claim 6, wherein said PERK is a human PERK.

8. The method of claim 7, wherein said PERK is encoded by a nucleic acid sequence herein identified as SEQ ID NO: 2.

9. The method of claim 7, wherein said siRNA or shRNA molecule comprises a nucleic acid sequence being perfectly complementary to a sequence within the nucleic acid sequence encoding said PERK.

10. The method of claim 5, wherein said nucleic acid molecule is comprised within a vector.

11. The method of claim 10, wherein said vector is a modified virus derived from a virus selected from the group consisting of a retrovirus, adenovirus, adeno-associated virus, pox virus, alphavirus, herpes virus and lentivirus.

12. The method of claim 11, wherein said vector is a modified adeno-associated virus.

13. The method of claim 1, wherein said cognitive function is selected from the group consisting of learning, behavioral plasticity and long term memory or a combination thereof.

14. The method of claim 1, wherein said cognitive function is a cortical or hippocampus dependent cognitive function.

15. The method of claim 1, wherein said age-related cognitive dysfunction is mild cognitive impairment.

16. The method of claim 1 comprising administering to said subject a modified adeno-associated virus vector comprising a nucleic acid molecule encoding an shRNA molecule comprising a nucleic acid sequence being perfectly complementary to a sequence within SEQ ID NO: 2.

17. The method of claim 16, wherein said age-related cognitive dysfunction is mild cognitive impairment.

* * * * *

UNITED STATES PATENT AND TRADEMARK OFFICE
CERTIFICATE OF CORRECTION

PATENT NO. : 10,246,712 B2
APPLICATION NO. : 15/335466
DATED : April 2, 2019
INVENTOR(S) : Rosenblum et al.

Page 1 of 2

It is certified that error appears in the above-identified patent and that said Letters Patent is hereby corrected as shown below:

In the Drawings

Drawing Sheet 11 of 30, (Fig. 4), change "Atenuation" to --Attenuation--.

Drawing Sheet 11 of 30, (Fig. 4), change "Consoloidation" to --Consolidation--.

Drawing Sheet 13 of 30, (Fig. 5), change "Contex" to --Context--.

In the Specification

Column 2, Line 19, change "sterotaxically" to --stereotaxically--.

Column 3, Line 59, change "p-eIf2 α" to --p-eIf2α--.

Column 5, Line 19, change "$p=3.65×10'$;" to --$p=3.65×10^{-8}$;--.

Column 8, Line 19, change "-1yl." to -- -1-yl.--.

Column 8, Line 24, change "-1yl" to -- -1-yl--.

Column 10, Line 2, change "Tourrett's" to --Tourette's--.

Column 13, Line 19, change "(Steolting" to --(Stoelting--.

Column 13, Line 38, change "(Steolting" to --(Stoelting--.

Column 14, Line 10, change "stereotacxic" to --stereotaxic--.

Column 14, Line 61, change "no.GI572502)." to --no. GI572502).--.

Signed and Sealed this
Twenty-sixth Day of May, 2020

Andrei Iancu
*Director of the United States Patent and Trademark Office*

Column 16, Line 26, change "Vibrotome." to --Vibratome.--.

Column 21, Lines 2-3, change "stereotacticaly" to --stereotactically--.

In the Claims

Column 43, Line 48, Claim 3, change "-1yl." to -- -1-yl.--.

Column 43, Line 52, Claim 4, change "-1yl." to -- -1-yl.--.